(12) United States Patent
Nawana et al.

(10) Patent No.: US 12,048,543 B2
(45) Date of Patent: Jul. 30, 2024

(54) DERMAL PATCH FOR COLLECTING A PHYSIOLOGICAL SAMPLE WITH REMOVABLE VIAL

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 17/991,284

(22) Filed: Nov. 21, 2022

(65) Prior Publication Data

US 2023/0147491 A1    May 11, 2023

Related U.S. Application Data

(63) Continuation-in-part of application No. 17/971,142, filed on Oct. 21, 2022, and a continuation-in-part of
(Continued)

(51) Int. Cl.
*A61B 5/00* (2006.01)
*A61B 5/15* (2006.01)
*A61B 5/151* (2006.01)

(52) U.S. Cl.
CPC .. *A61B 5/150969* (2013.01); *A61B 5/150099* (2013.01); *A61B 5/150351* (2013.01); *A61B 5/150702* (2013.01); *A61B 5/150748* (2013.01); *A61B 5/150755* (2013.01); *A61B 5/150786* (2013.01); *A61B 5/15113* (2013.01)

(58) Field of Classification Search
CPC ........ A61B 5/150969; A61B 5/150099; A61B 5/150351; A61B 5/150702; A61B 5/150748; A61B 5/150755; A61B 5/150786; A61B 5/15113
See application file for complete search history.

(56) References Cited

U.S. PATENT DOCUMENTS 5,015,228 A    5/1991    Columbus et al.
5,338,308 A    8/1994    Wilk
(Continued)

FOREIGN PATENT DOCUMENTS

AU    2006283345 A1    3/2007
AU    2016266112 A1    12/2016
(Continued)

OTHER PUBLICATIONS

International Search Report and Written Opinion for PCT/US2022/046384 mailed Jan. 5, 2023.
(Continued)

*Primary Examiner* — May A Abouelela
(74) *Attorney, Agent, or Firm* — Potomac Law Group, PLLC; John J. Penny, Jr.

(57) ABSTRACT

A device for collecting a physiological sample from a subject includes a lancet and a cartridge configured to couple to the lancet. The needle is configured to puncture the subject's skin. The lancet is configured to automatically deploy the needle when coupled to the lancet which allows the needle to puncture the subject's skin and draw a physiological sample. The device further includes a vial disposed within the cartridge. The vial is configured to receive the drawn physiological sample.

14 Claims, 74 Drawing Sheets

Related U.S. Application Data application No. 17/521,466, filed on Nov. 8, 2021, now Pat. No. 11,510,602.

(56) References Cited

U.S. PATENT DOCUMENTS

| | | |
|---|---|---|
| 5,441,490 A | 8/1995 | Svedman |
| 5,527,288 A | 6/1996 | Gross et al. |
| 5,602,037 A | 2/1997 | Ostgaard et al. |
| 5,636,640 A * | 6/1997 | Staehlin ............ A61B 5/150419 600/577 |
| 5,680,872 A * | 10/1997 | Sesekura ............ A61B 5/15111 600/583 |
| 5,848,991 A | 12/1998 | Gross et al. |
| 5,997,501 A | 12/1999 | Gross et al. |
| 6,234,980 B1 * | 5/2001 | Bell ................ A61B 5/150305 604/314 |
| 6,315,985 B1 | 11/2001 | Wu et al. |
| 6,454,140 B1 | 9/2002 | Jinks |
| 6,500,150 B1 | 12/2002 | Gross et al. |
| 6,506,168 B1 * | 1/2003 | Fathallah ......... A61B 5/150022 600/578 |
| 6,524,284 B1 | 2/2003 | Marshall |
| 6,610,273 B2 | 8/2003 | Wu et al. |
| 6,623,457 B1 | 9/2003 | Rosenberg |
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Lastovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 | 12/2009 | Wall |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 * | 8/2014 | Brancazio ........ A61B 5/150022 600/583 |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 * | 7/2016 | Fletcher ............ A61B 5/15101 |
| 9,380,973 B2 * | 7/2016 | Fletcher .................. A61M 1/36 |
| 9,468,404 B2 | 10/2016 | Hayden |
| 9,480,428 B2 | 11/2016 | Colin et al. |
| 9,504,813 B2 | 11/2016 | Buss |
| 9,522,225 B2 * | 12/2016 | Chong ............ A61M 5/14248 |
| 9,549,700 B2 * | 1/2017 | Fletcher .................. G01N 1/34 |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |
| 9,724,462 B2 | 8/2017 | Rotem |
| 9,730,624 B2 | 8/2017 | Gonzalez-Zugasti et al. |
| 9,770,578 B2 | 9/2017 | Chowdhury |

(56) References Cited

U.S. PATENT DOCUMENTS

| | | | |
|---|---|---|---|
| 9,775,551 B2 | 10/2017 | Bernstein et al. | |
| 9,782,574 B2 | 10/2017 | Simmers | |
| 9,789,249 B2 | 10/2017 | Frederickson et al. | |
| 9,789,299 B2 | 10/2017 | Simmers | |
| 9,844,631 B2 | 12/2017 | Bureau | |
| 9,849,270 B2 | 12/2017 | Stockholm | |
| D808,515 S | 1/2018 | Atkin et al. | |
| 9,861,580 B2 | 1/2018 | Mueting et al. | |
| 9,861,801 B2 | 1/2018 | Baker et al. | |
| 9,872,975 B2 | 1/2018 | Burton et al. | |
| 9,884,151 B2 | 2/2018 | Sullivan et al. | |
| 9,895,520 B2 | 2/2018 | Burton et al. | |
| 9,956,170 B2 | 5/2018 | Cantor et al. | |
| 9,968,767 B1 | 5/2018 | Hasan et al. | |
| 9,987,629 B2 | 6/2018 | Berthier et al. | |
| 9,993,189 B2 | 6/2018 | Phan et al. | |
| 10,004,887 B2 | 6/2018 | Gross et al. | |
| 10,010,676 B2 | 7/2018 | Bureau | |
| 10,010,706 B2 | 7/2018 | Gonzalez et al. | |
| 10,010,707 B2 | 7/2018 | Colburn et al. | |
| 10,016,315 B2 * | 7/2018 | Letourneau | A61F 13/15 |
| 10,029,845 B2 | 7/2018 | Jinks | |
| 10,035,008 B2 | 7/2018 | Brandwein et al. | |
| 10,076,649 B2 | 9/2018 | Gilbert et al. | |
| 10,080,843 B2 | 9/2018 | Bureau | |
| 10,080,846 B2 | 9/2018 | Sonderegger et al. | |
| 10,099,043 B2 | 10/2018 | Berry et al. | |
| 10,105,524 B2 | 10/2018 | Meyer et al. | |
| 10,111,807 B2 | 10/2018 | Baker et al. | |
| D834,704 S | 11/2018 | Atkin et al. | |
| 10,154,957 B2 | 12/2018 | Zhang et al. | |
| 10,155,334 B2 | 12/2018 | Rendon | |
| 10,183,156 B2 | 1/2019 | Ross et al. | |
| 10,188,335 B2 | 1/2019 | Haghgooie et al. | |
| D840,020 S | 2/2019 | Howgill | |
| 10,201,691 B2 | 2/2019 | Berry et al. | |
| 10,232,157 B2 | 3/2019 | Berry et al. | |
| 10,232,160 B2 | 3/2019 | Baker et al. | |
| 10,248,765 B1 * | 4/2019 | Holmes | A61B 5/150022 |
| 10,265,484 B2 | 4/2019 | Stuart et al. | |
| 10,272,214 B2 | 4/2019 | Child et al. | |
| 10,300,260 B2 | 5/2019 | Wirtanen et al. | |
| 10,307,578 B2 | 6/2019 | Frederickson et al. | |
| 10,315,021 B2 | 6/2019 | Frederickson et al. | |
| 10,327,990 B2 | 6/2019 | Egeland et al. | |
| 10,328,248 B2 | 6/2019 | Baker et al. | |
| 10,335,560 B2 | 7/2019 | Stein et al. | |
| 10,335,562 B2 | 7/2019 | Jinks et al. | |
| 10,335,563 B2 | 7/2019 | Brewer et al. | |
| 10,357,610 B2 | 7/2019 | Sonderegger | |
| 10,384,047 B2 | 8/2019 | Simmers | |
| 10,391,290 B2 | 8/2019 | Burton et al. | |
| 10,398,885 B2 | 9/2019 | Frits et al. | |
| 10,406,339 B2 | 9/2019 | Simmers | |
| 10,410,838 B2 | 9/2019 | Hanson et al. | |
| 10,426,390 B2 | 10/2019 | Berthier et al. | |
| 10,426,739 B2 | 10/2019 | Knutson | |
| 10,478,346 B2 | 11/2019 | Knutson | |
| 10,492,716 B2 | 12/2019 | Berthier et al. | |
| 10,507,286 B2 | 12/2019 | Egeland et al. | |
| 10,518,071 B2 | 12/2019 | Kulkarni | |
| D872,853 S | 1/2020 | Stuart et al. | |
| 10,525,463 B2 | 1/2020 | Kelly et al. | |
| 10,542,922 B2 | 1/2020 | Sia et al. | |
| 10,543,310 B2 | 1/2020 | Bernstein et al. | |
| 10,549,079 B2 | 2/2020 | Burton et al. | |
| 10,568,937 B2 | 2/2020 | Hattersley et al. | |
| D878,544 S | 3/2020 | Stuart et al. | |
| 10,576,257 B2 | 3/2020 | Berry et al. | |
| 10,596,333 B2 | 3/2020 | Howgill | |
| 10,598,583 B1 * | 3/2020 | Peeters | A61B 5/150099 |
| 10,638,963 B2 | 5/2020 | Beyerlein et al. | |
| 10,646,703 B2 | 5/2020 | Chowdhury | |
| 10,653,349 B2 | 5/2020 | Delamarche et al. | |
| 10,695,289 B2 | 6/2020 | Brown et al. | |
| 10,695,547 B2 | 6/2020 | Burton et al. | |
| 10,716,926 B2 | 7/2020 | Burton et al. | |
| 10,729,842 B2 | 8/2020 | Hooven et al. | |
| 10,772,550 B2 | 9/2020 | Aceti et al. | |
| 10,779,757 B2 | 9/2020 | Berthier et al. | |
| 10,799,166 B2 | 10/2020 | Gonzalez-Zugasti et al. | |
| 10,835,163 B2 | 11/2020 | Haghgooie et al. | |
| 10,881,342 B2 | 1/2021 | Kelly et al. | |
| 10,888,259 B2 | 1/2021 | Jordan et al. | |
| 10,926,030 B2 * | 2/2021 | Lanigan | H01Q 1/273 |
| 10,932,710 B2 | 3/2021 | Jordan et al. | |
| 10,939,860 B2 | 3/2021 | Levinson et al. | |
| 10,940,085 B2 | 3/2021 | Baker et al. | |
| 10,953,211 B2 | 3/2021 | Ross et al. | |
| 11,020,548 B2 | 6/2021 | Stuart et al. | |
| 11,033,212 B2 | 6/2021 | Berthier et al. | |
| 11,040,183 B2 | 6/2021 | Baker et al. | |
| 11,103,685 B2 | 8/2021 | Gonzalez et al. | |
| 11,110,234 B2 | 9/2021 | Richardson et al. | |
| 11,116,953 B2 | 9/2021 | Kobayashi et al. | |
| 11,147,955 B2 | 10/2021 | Gross et al. | |
| 11,177,029 B2 | 11/2021 | Levinson et al. | |
| 11,197,625 B1 | 12/2021 | Schleicher et al. | |
| 11,202,895 B2 | 12/2021 | Davis et al. | |
| 11,207,477 B2 | 12/2021 | Hodson | |
| 11,247,033 B2 | 2/2022 | Baker et al. | |
| 11,253,179 B2 | 2/2022 | Bernstein et al. | |
| 11,266,337 B2 | 3/2022 | Jackson et al. | |
| 11,273,272 B2 | 3/2022 | Stuart et al. | |
| 11,291,989 B2 | 4/2022 | Morrison | |
| 11,298,060 B2 | 4/2022 | Jordan et al. | |
| 11,298,478 B2 | 4/2022 | Stuart et al. | |
| 11,304,632 B2 | 4/2022 | Mou et al. | |
| 11,344,684 B2 | 5/2022 | Richardson et al. | |
| 11,395,614 B2 | 7/2022 | Berthier et al. | |
| 11,452,474 B1 | 9/2022 | Nawana et al. | |
| 11,458,289 B2 | 10/2022 | Moeckly et al. | |
| 11,497,712 B2 | 11/2022 | Stein et al. | |
| 11,497,866 B2 | 11/2022 | Howgill | |
| 11,510,602 B1 | 11/2022 | Nawana et al. | |
| 2002/0077584 A1 * | 6/2002 | Lin | A61B 5/150984 |
| | | | 604/21 |
| 2002/0193740 A1 | 12/2002 | Alchas et al. | |
| 2004/0002121 A1 * | 1/2004 | Regan | A61B 5/150343 |
| | | | 435/7.2 |
| 2004/0010207 A1 | 1/2004 | Flaherty et al. | |
| 2004/0059256 A1 * | 3/2004 | Perez | A61B 5/15113 |
| | | | 600/583 |
| 2004/0059366 A1 * | 3/2004 | Sato | A61B 5/150068 |
| | | | 606/182 |
| 2004/0106904 A1 | 6/2004 | Gonnelli et al. | |
| 2004/0162467 A1 * | 8/2004 | Cook | A61B 5/150351 |
| | | | 600/309 |
| 2005/0106713 A1 | 5/2005 | Phan et al. | |
| 2005/0118388 A1 | 6/2005 | Kingsford | |
| 2006/0047243 A1 | 3/2006 | Rosenberg | |
| 2006/0068490 A1 | 3/2006 | Tang et al. | |
| 2006/0142651 A1 | 6/2006 | Brister et al. | |
| 2006/0271084 A1 * | 11/2006 | Schraga | A61B 5/14532 |
| | | | 600/573 |
| 2007/0004989 A1 | 1/2007 | Dhillon | |
| 2007/0191696 A1 * | 8/2007 | Mischler | G01N 21/552 |
| | | | 600/347 |
| 2008/0003274 A1 | 1/2008 | Kaiser | |
| 2008/0287864 A1 | 11/2008 | Rosenberg | |
| 2009/0012472 A1 | 1/2009 | Ahm et al. | |
| 2009/0036826 A1 | 2/2009 | Sage, Jr. et al. | |
| 2009/0099427 A1 | 4/2009 | Jina et al. | |
| 2009/0112125 A1 | 4/2009 | Tamir | |
| 2009/0198215 A1 * | 8/2009 | Chong | A61M 5/1413 |
| | | | 604/506 |
| 2009/0259176 A1 | 10/2009 | Yairi | |
| 2010/0198107 A1 * | 8/2010 | Groll | A61B 5/15113 |
| | | | 600/583 |
| 2010/0249560 A1 | 9/2010 | Levinson et al. | |
| 2010/0256524 A1 | 10/2010 | Levinson et al. | |
| 2010/0269837 A1 | 10/2010 | Levinson et al. | |
| 2010/0272652 A1 | 10/2010 | Levinson | |

(56) References Cited

U.S. PATENT DOCUMENTS

| | | |
|---|---|---|
| 2011/0009847 A1 | 1/2011 | Levinson et al. |
| 2011/0060280 A1 | 3/2011 | Caffey et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1* | 6/2011 | Pesach ............. A61B 5/150267 600/345 |
| 2011/0172508 A1 | 7/2011 | Chickering, III et al. |
| 2011/0172510 A1 | 7/2011 | Chickering, III et al. |
| 2011/0198221 A1 | 8/2011 | Angelescu |
| 2011/0213335 A1 | 9/2011 | Burton et al. |
| 2011/0245635 A1* | 10/2011 | Fujiwara ............. A61B 5/15117 600/573 |
| 2011/0257497 A1 | 10/2011 | Tamada et al. |
| 2011/0288389 A9 | 11/2011 | Levinson et al. |
| 2012/0016308 A1* | 1/2012 | Schott ............. A61B 5/150984 604/173 |
| 2012/0041338 A1 | 2/2012 | Chickering, III et al. |
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1* | 5/2012 | Brancazio ......... A61B 5/150022 600/576 |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1* | 11/2012 | Haghgooie ....... A61B 5/150213 210/321.62 |
| 2012/0277629 A1* | 11/2012 | Bernstein ......... A61B 5/150022 600/578 |
| 2012/0277696 A1 | 11/2012 | Gonzalez-Zugasti et al. |
| 2012/0277697 A1* | 11/2012 | Haghgooie ......... A61B 5/14514 604/327 |
| 2013/0018279 A1* | 1/2013 | Plante .............. A61B 5/150755 600/583 |
| 2013/0158468 A1* | 6/2013 | Bernstein ................ A61M 1/38 604/173 |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1 | 10/2013 | Angelescu |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1* | 10/2014 | Gelfand ............ A61B 5/150221 600/583 |
| 2014/0309555 A1* | 10/2014 | Gelfand ............ A61B 5/150748 600/583 |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1* | 7/2016 | Matsunami ....... A61B 5/150732 |
| 2016/0256095 A1* | 9/2016 | Krasnow ........... A61B 5/150076 |
| 2016/0262676 A1 | 9/2016 | Haghgooie et al. |
| 2016/0315123 A1 | 10/2016 | Kim et al. |
| 2016/0324506 A1* | 11/2016 | Tariyal ............. A61B 5/150755 |
| 2016/0354589 A1 | 12/2016 | Kobayashi et al. |
| 2016/0361006 A1* | 12/2016 | Bullington ............ B01L 3/0217 |
| 2017/0001192 A1 | 1/2017 | Kelly et al. |
| 2017/0014822 A1 | 1/2017 | Ker |
| 2017/0021067 A1* | 1/2017 | Todd ................. A61B 5/150099 |
| 2017/0021117 A1 | 1/2017 | Howgill |
| 2017/0035337 A1* | 2/2017 | Wilkinson ........ A61B 5/150267 |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1* | 5/2017 | Holmes ................ G01N 33/491 |
| 2017/0127991 A1 | 5/2017 | Bernstein et al. |
| 2017/0173288 A1 | 6/2017 | Stam et al. |
| 2017/0197029 A1* | 7/2017 | Cindrich ........... A61M 5/16804 |
| 2017/0224912 A1* | 8/2017 | Yodfat .............. A61M 5/14248 |
| 2017/0231543 A1 | 8/2017 | Cunningham et al. |
| 2017/0290977 A1 | 10/2017 | Schauderna |
| 2018/0001021 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1* | 3/2018 | Moga ................ A61B 5/150343 |
| 2018/0103884 A1* | 4/2018 | Delamarche ..... A61B 5/150221 |
| 2018/0126058 A1 | 5/2018 | David et al. |
| 2018/0132515 A1 | 5/2018 | Lawrence et al. |
| 2018/0132774 A1 | 5/2018 | Gonzalez-Zugasti et al. |
| 2018/0242890 A1* | 8/2018 | Chickering, III ........................... A61B 5/150221 |
| 2018/0243543 A1 | 8/2018 | Baek et al. |
| 2018/0296148 A1* | 10/2018 | Gelfand .............. A61M 1/3406 |
| 2018/0344631 A1 | 12/2018 | Zhang et al. |
| 2018/0369512 A1 | 12/2018 | Blatchford et al. |
| 2019/0000365 A1* | 1/2019 | Beyerlein ............ G01N 33/487 |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1* | 5/2019 | Diebold ........... A61B 5/150022 600/575 |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1* | 3/2020 | Berthier ............ A61B 5/15117 |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1* | 8/2020 | Ivosevic .......... A61B 5/150755 |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1* | 12/2021 | Weidemaier ..... A61B 5/150755 |

(56) References Cited

U.S. PATENT DOCUMENTS

| | | | |
|---|---|---|---|
| 2022/0031211 A1* | 2/2022 | Yakhnich | A61B 5/150068 |
| 2022/0058895 A1 | 2/2022 | Han | |
| 2022/0062607 A1 | 3/2022 | Davis et al. | |
| 2022/0071534 A9 | 3/2022 | Gonzalez-Zugasti et al. | |
| 2022/0133192 A1 | 5/2022 | Brancazio | |
| 2022/0134072 A1 | 5/2022 | Kosel et al. | |
| 2022/0215921 A1 | 7/2022 | Levinson et al. | |
| 2022/0218251 A1 | 7/2022 | Jackson et al. | |
| 2022/0233117 A1* | 7/2022 | Lee | A61B 5/150389 |
| 2022/0249818 A1 | 8/2022 | Chickering, III et al. | |
| 2022/0257158 A1 | 8/2022 | Haghgooie et al. | |
| 2022/0287642 A1 | 9/2022 | Chickering, III et al. | |
| 2022/0313128 A1 | 10/2022 | Bernstein et al. | |
| 2022/0330860 A1 | 10/2022 | Nawana | |
| 2022/0361784 A1 | 11/2022 | Jordan et al. | |
| 2023/0109881 A1 | 4/2023 | Nawana et al. | |

FOREIGN PATENT DOCUMENTS

| | | |
|---|---|---|
| CN | 101296752 A | 10/2008 |
| EP | 0931507 A1 | 7/1999 |
| EP | 1769735 A1 | 4/2007 |
| EP | 2493537 A2 | 9/2012 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| JP | 2004024164 A | 1/2004 |
| KR | 101857300 B1 | 5/2018 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |

(56) References Cited

FOREIGN PATENT DOCUMENTS

| | | |
|---|---|---|
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016018892 A1 | 2/2016 |
| WO | 2016081843 A1 | 5/2016 |
| WO | 2016099986 A1 | 6/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion for PCT/US2022/048913 mailed Feb. 21, 2023.

International Search Report and Written Opinion for PCT/US22/029829 mailed Nov. 23, 2022.

International Search Report and Written Opinion, PCT/US2022/048913, dated Feb. 21, 2023, 16 pages.

English machine translation of JP-2004024164-A, patents.google.com, 8 pages.

International Search Report and Written Opinion, PCT/US2022/029829, dated Nov. 23, 2022, 16 pages.

International Search Report and Written Opinion, PCT/US2022/046384, dated Jan. 5, 2023, 12 pages.

International Search Report and Written Opinion, PCT/US2022/024607, dated Aug. 4, 2022, 17 pages.

Taiwan Office Action, TW111142334, dated May 18, 2023, 15 pages.

U.S. Appl. No. 17/719,881, filed Apr. 13, 2022, Self-Contained Dermal Patch for Detection of Physiological Analytes.

U.S. Appl. No. 17/412,205, filed Aug. 25, 2021, Dermal Patch System.

U.S. Appl. No. 17/747,544, filed May 18, 2022, Self-Contained Dermal Patch for Blood Analysis.

U.S. Appl. No. 17/412,213, filed Aug. 25, 2021, Dual Lever Dermal Patch System.

U.S. Appl. No. 17/903,802, filed Sep. 6, 2022, Dual Lever Dermal Patch System.

U.S. Appl. No. 17/500,873, filed Oct. 13, 2021, Mono Dose Dermal Patch for Pharmaceutical Delivery.

U.S. Appl. No. 17/521,466, filed Nov. 8, 2021, Dermal Patch for Collecting a Physiological Sample.

U.S. Appl. No. 17/994,454, filed Nov. 28, 2022, Dermal Patch for Collecting a Physiological Sample.

U.S. Appl. No. 18/090,026, filed Dec. 28, 2022, Dermal Patch for Collecting a Physiological Sample.

U.S. Appl. No. 18/411,442, filed Jan. 12, 2024, Dermal Patch for Collecting a Physiological Sample.

U.S. Appl. No. 17/971,142, filed Oct. 21, 2022, Dermal Patch for Collecting a Physiological Sample.

U.S. Appl. No. 18/090,063, filed Dec. 28, 2022, Dermal Patch with a Diagnostic Test Strip.

U.S. Appl. No. 18/090,107, filed Dec. 28, 2022, Dermal Patch for Delivering a Pharmaceutical.

(56) References Cited

OTHER PUBLICATIONS

International Preliminary Report on Patentability for International Application No. PCT/US2022/029829 dated Nov. 21, 2023.
International Preliminary Report on Patentability for International Application No. PCT/US2022/024607 dated Oct. 12, 2023.
Taiwan Office Action for Taiwanese Patent Application No. TW111142334 issued Dec. 12, 2023.
Written Opinion for International Application No. PCT/US2022/024607 issued Oct. 12, 2023.

* cited by examiner

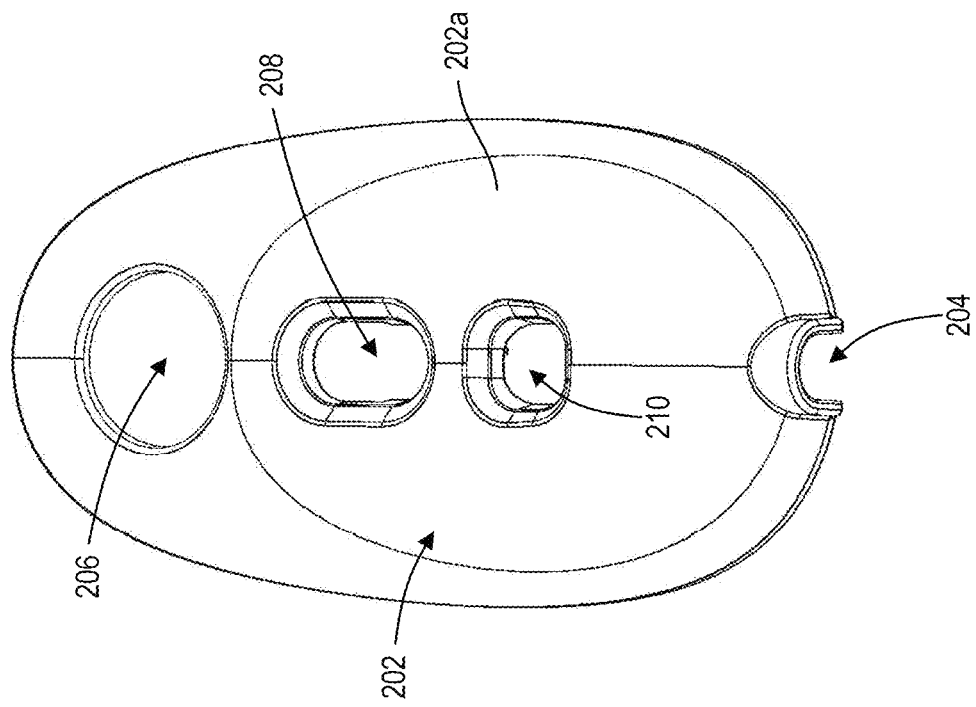
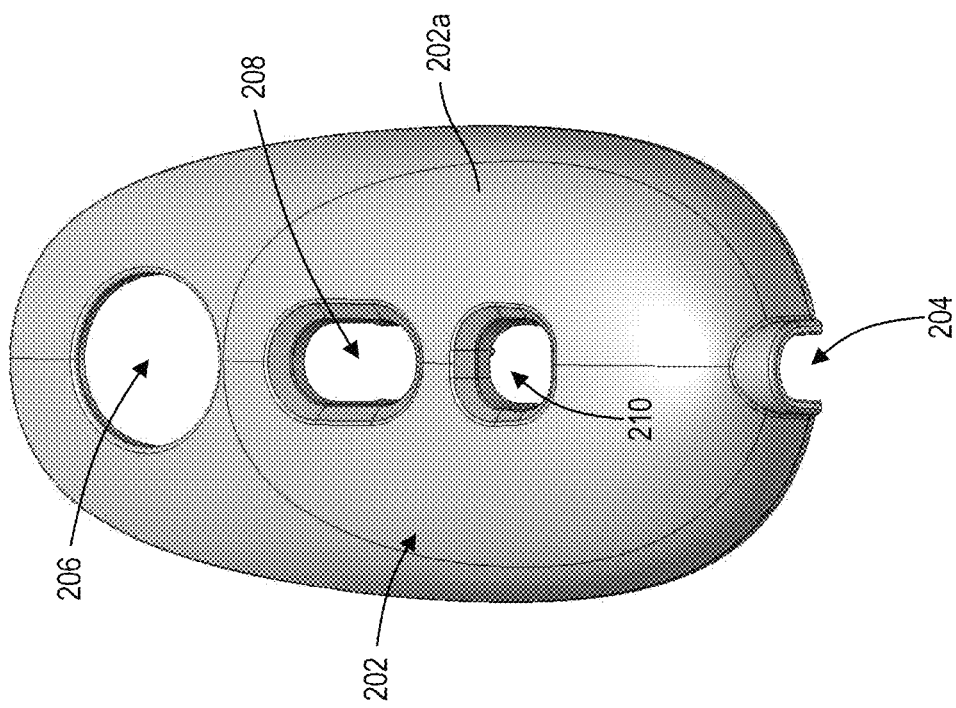

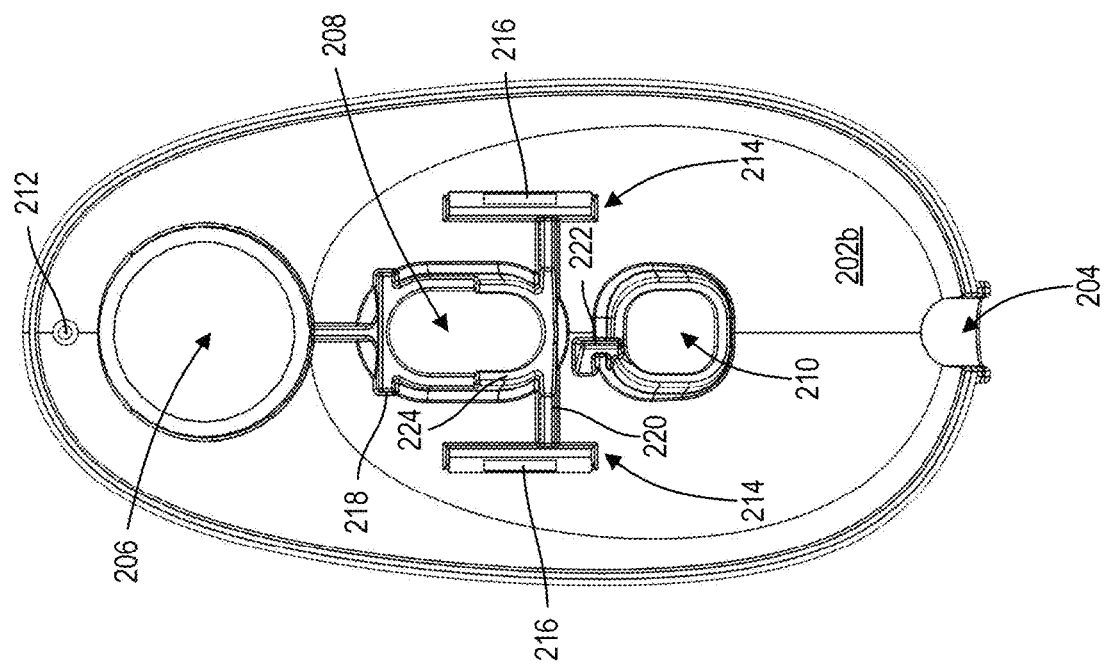
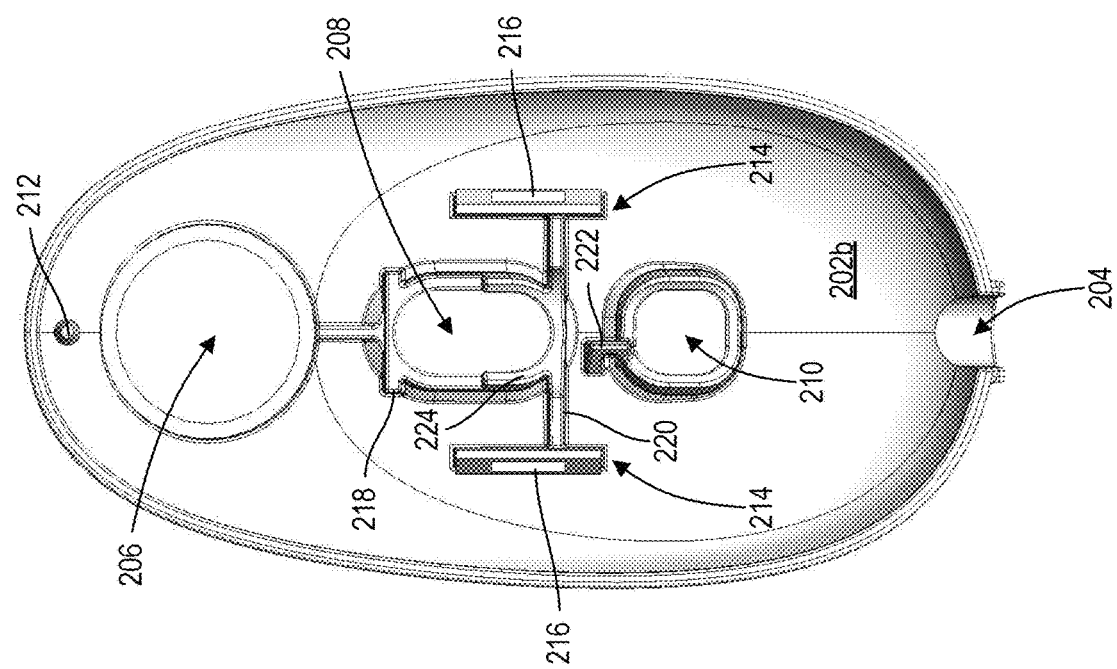

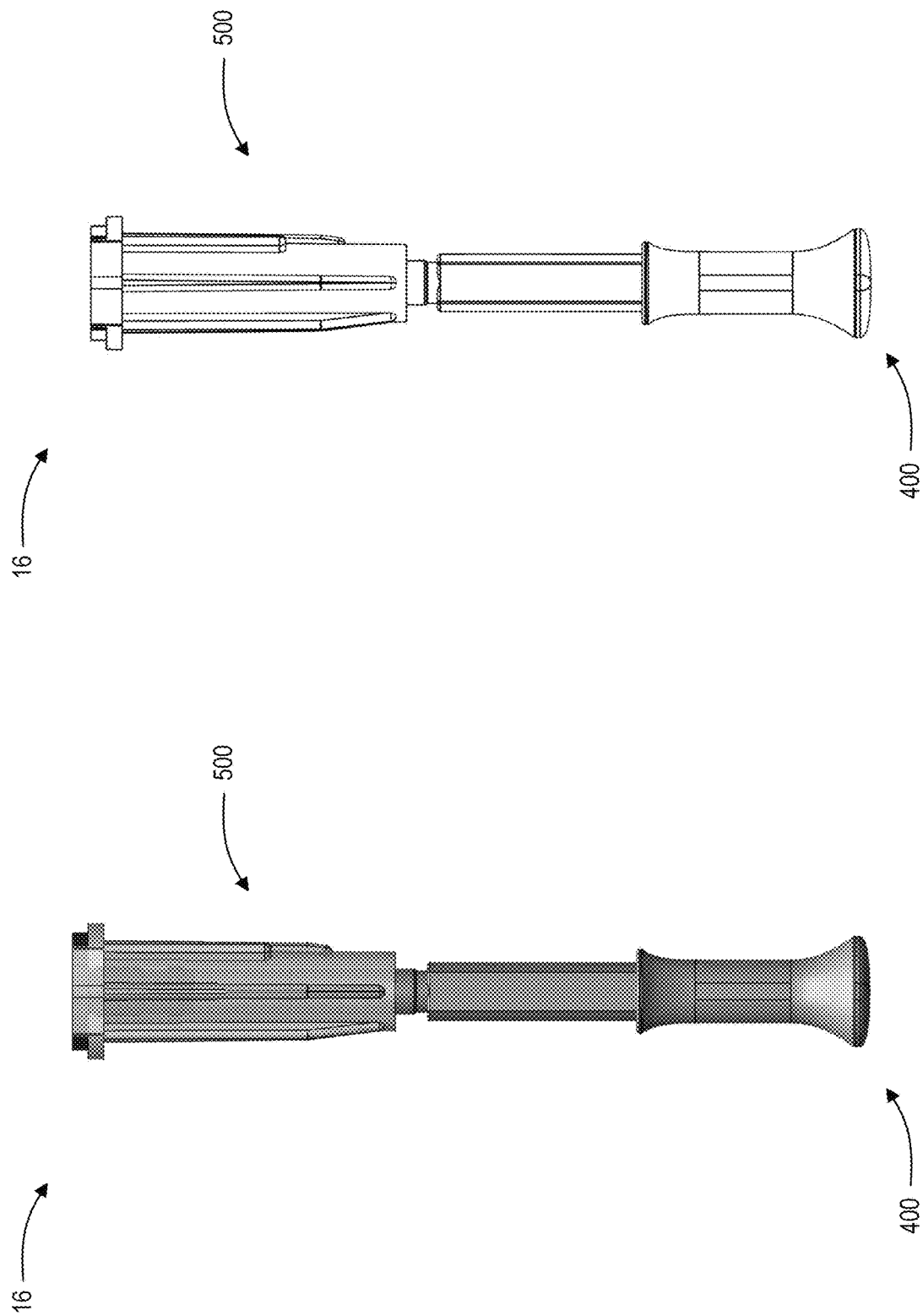

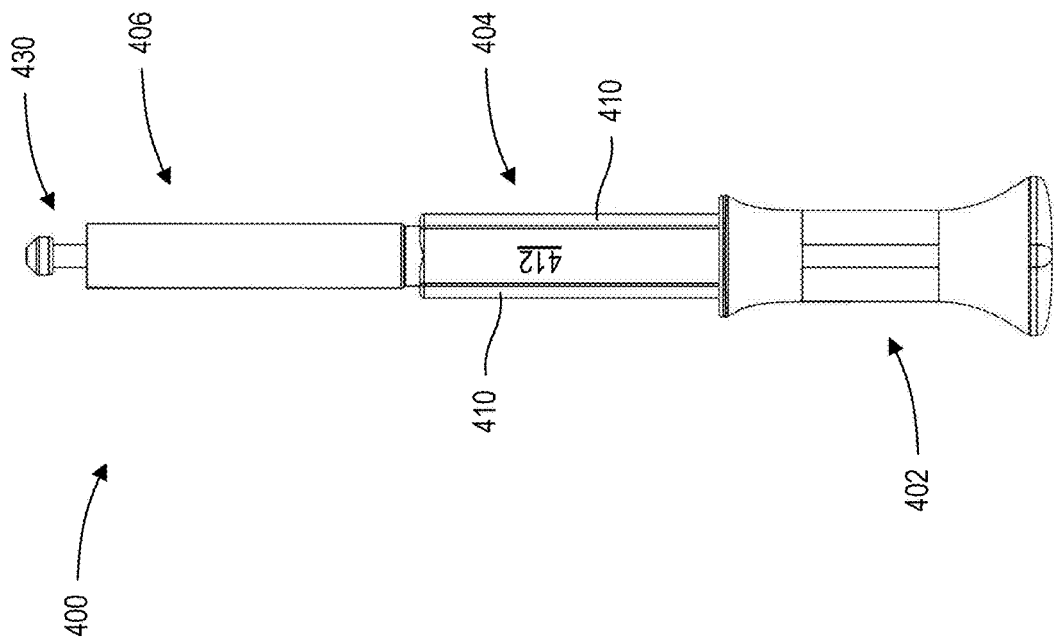
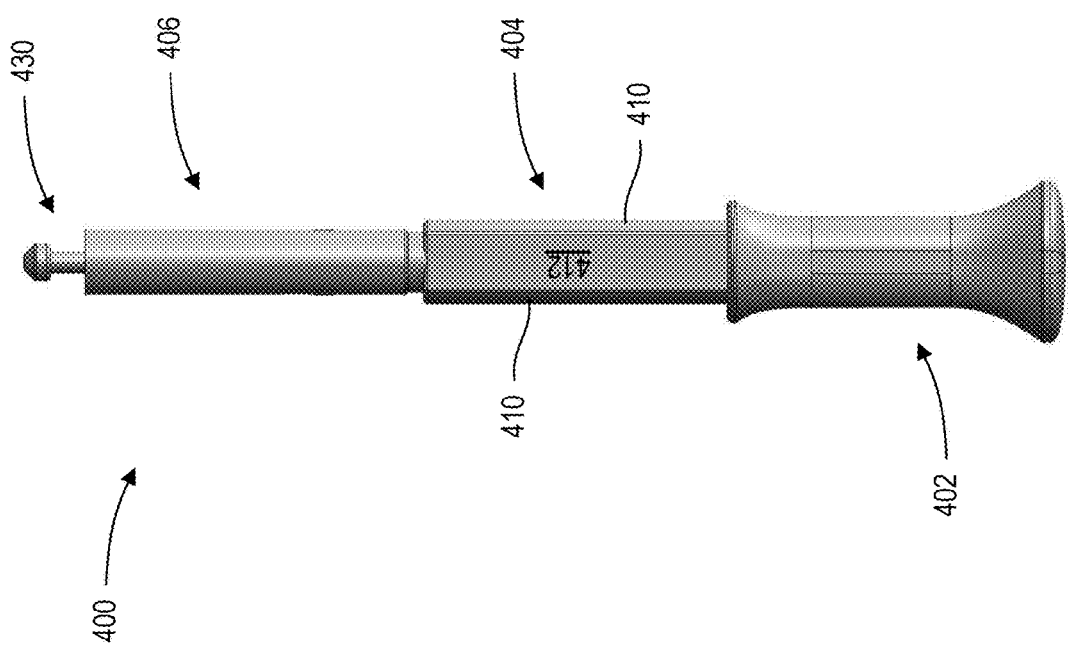
Fig. 29A
Fig. 29B

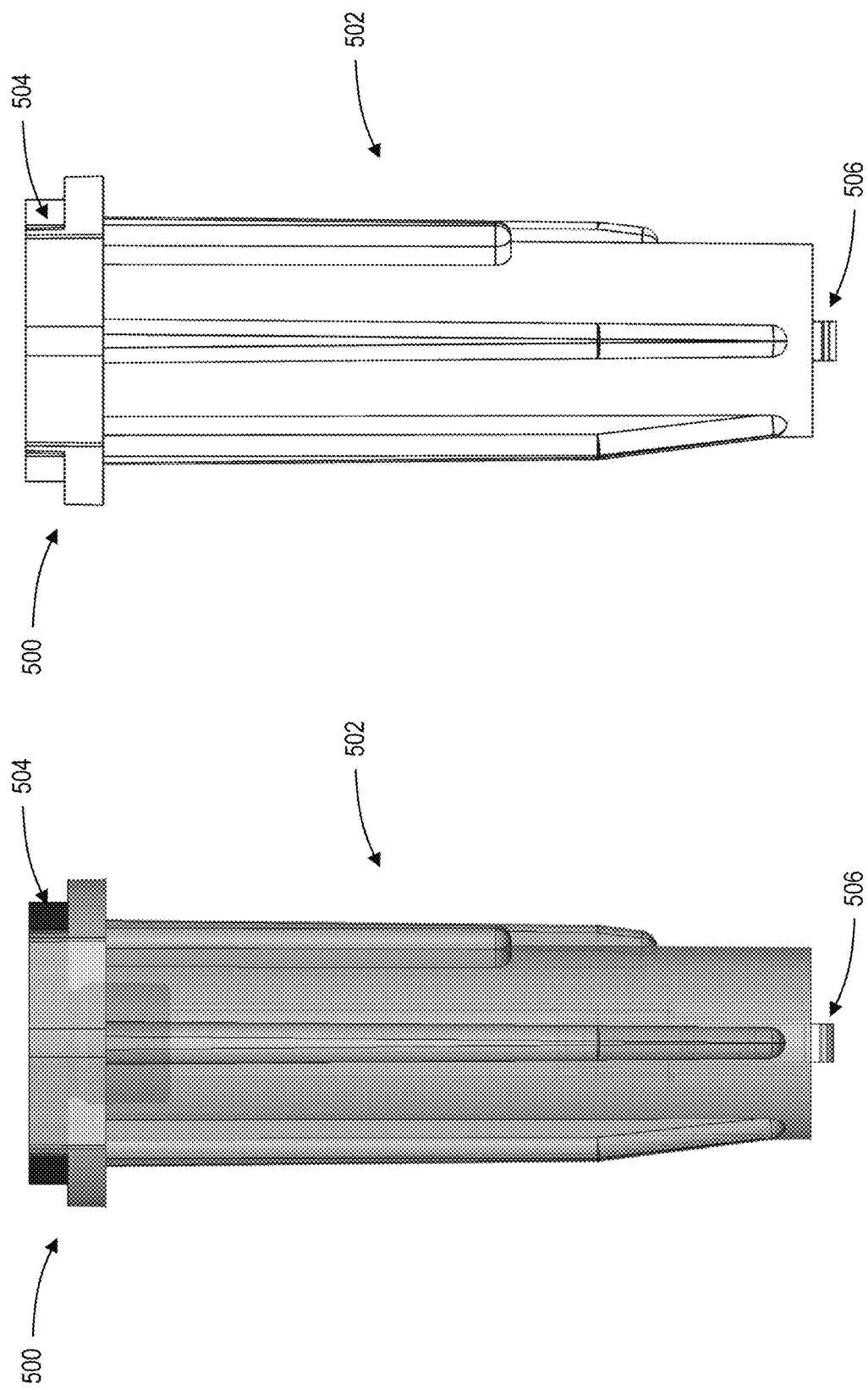

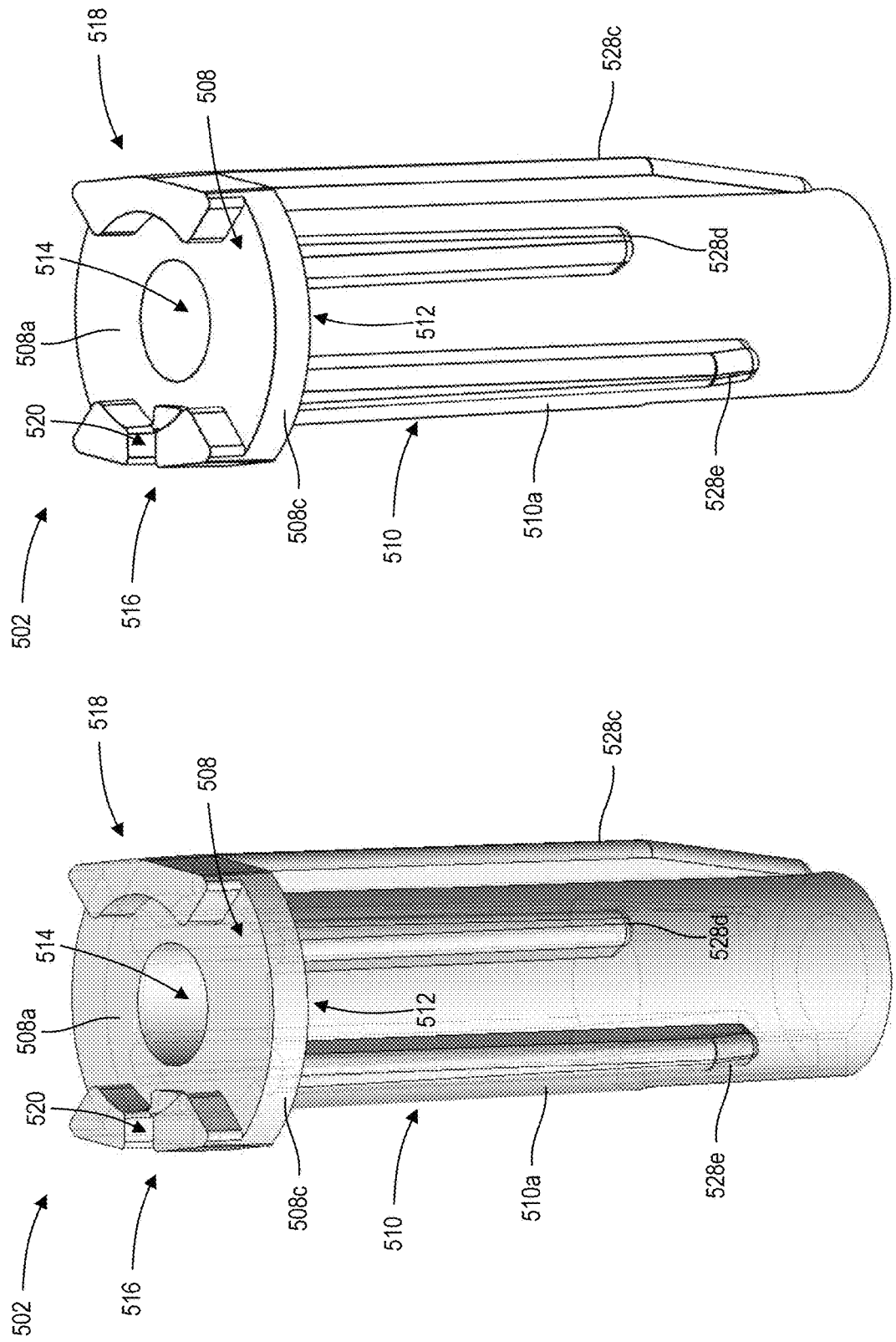

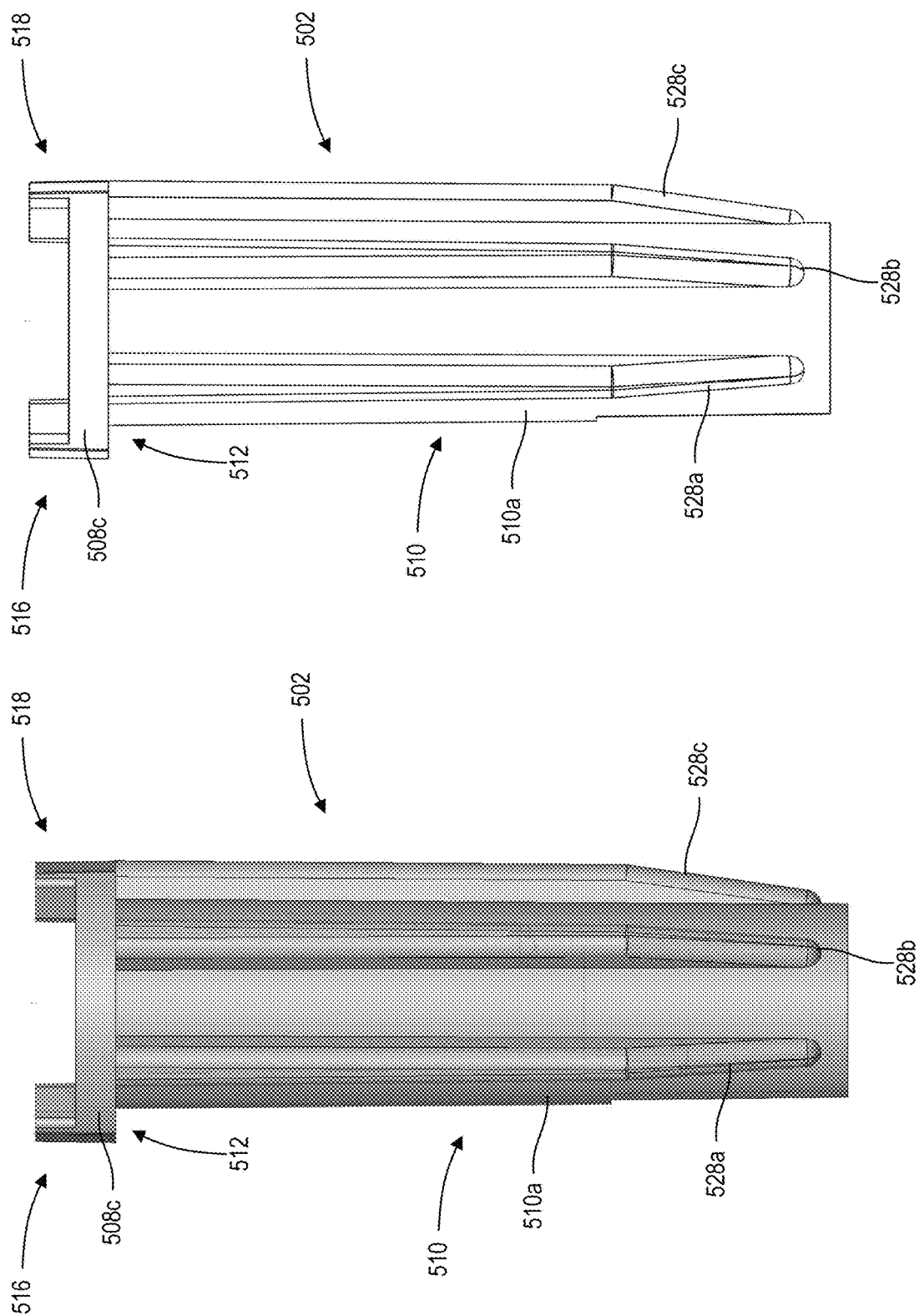

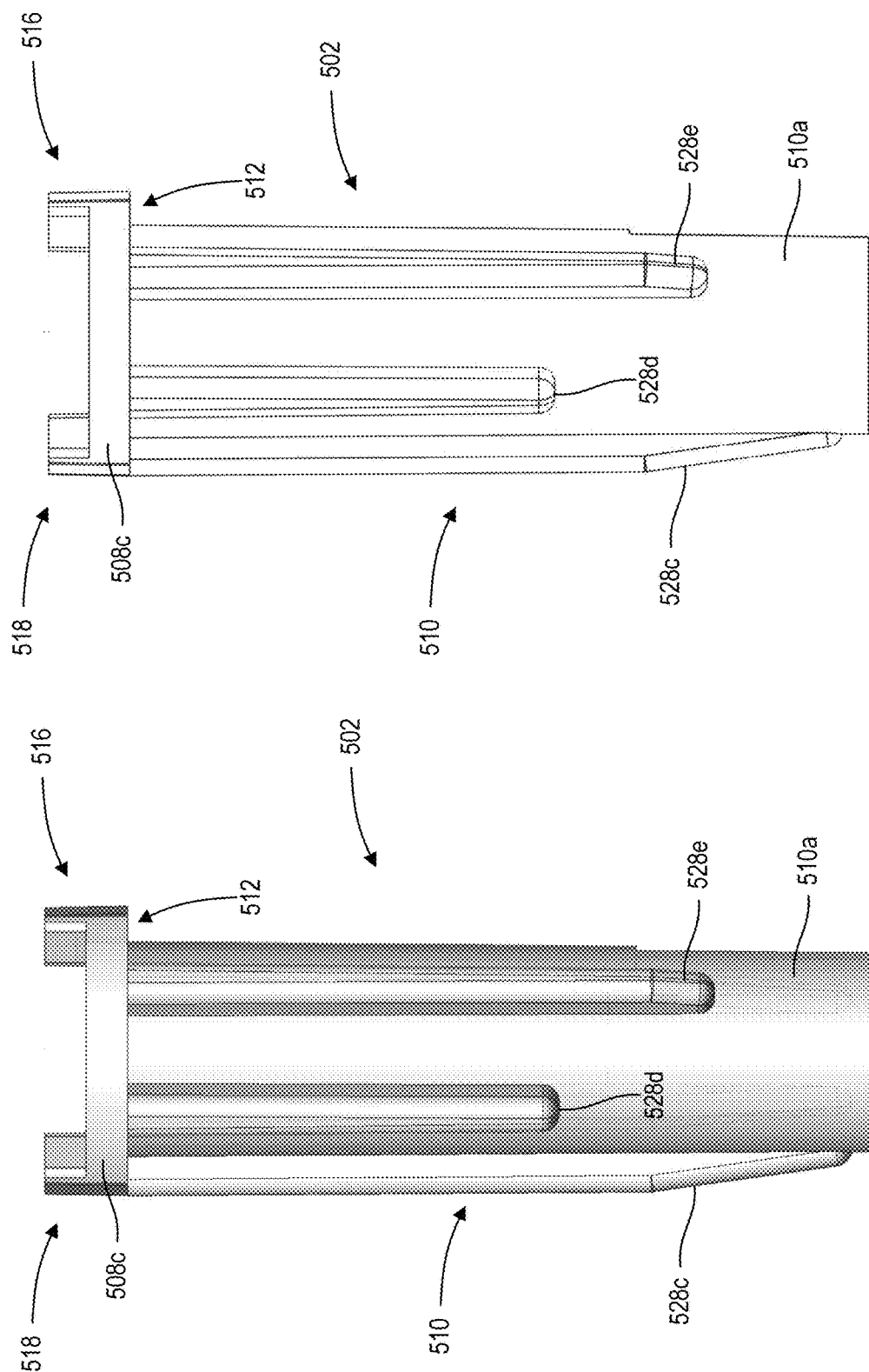

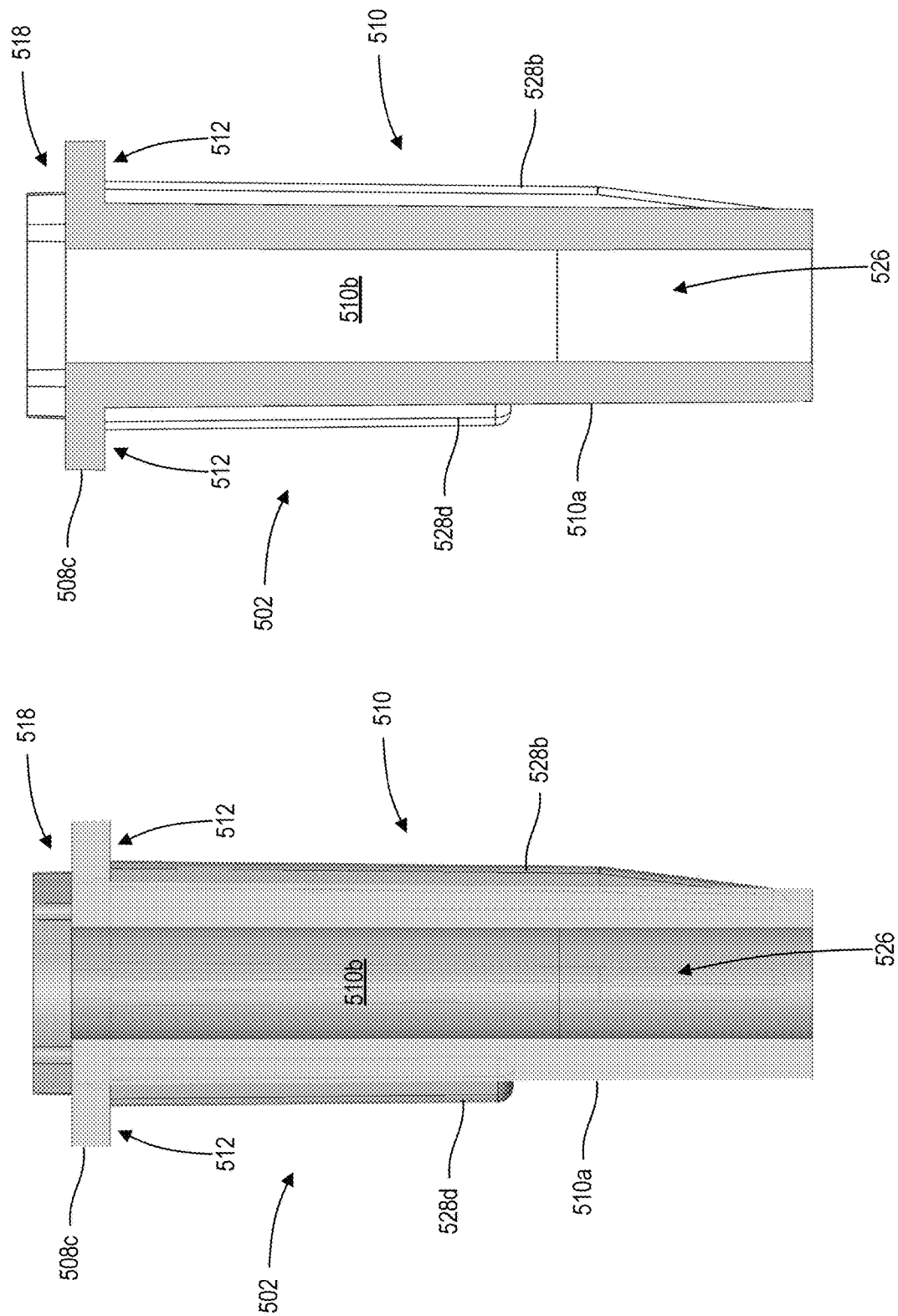

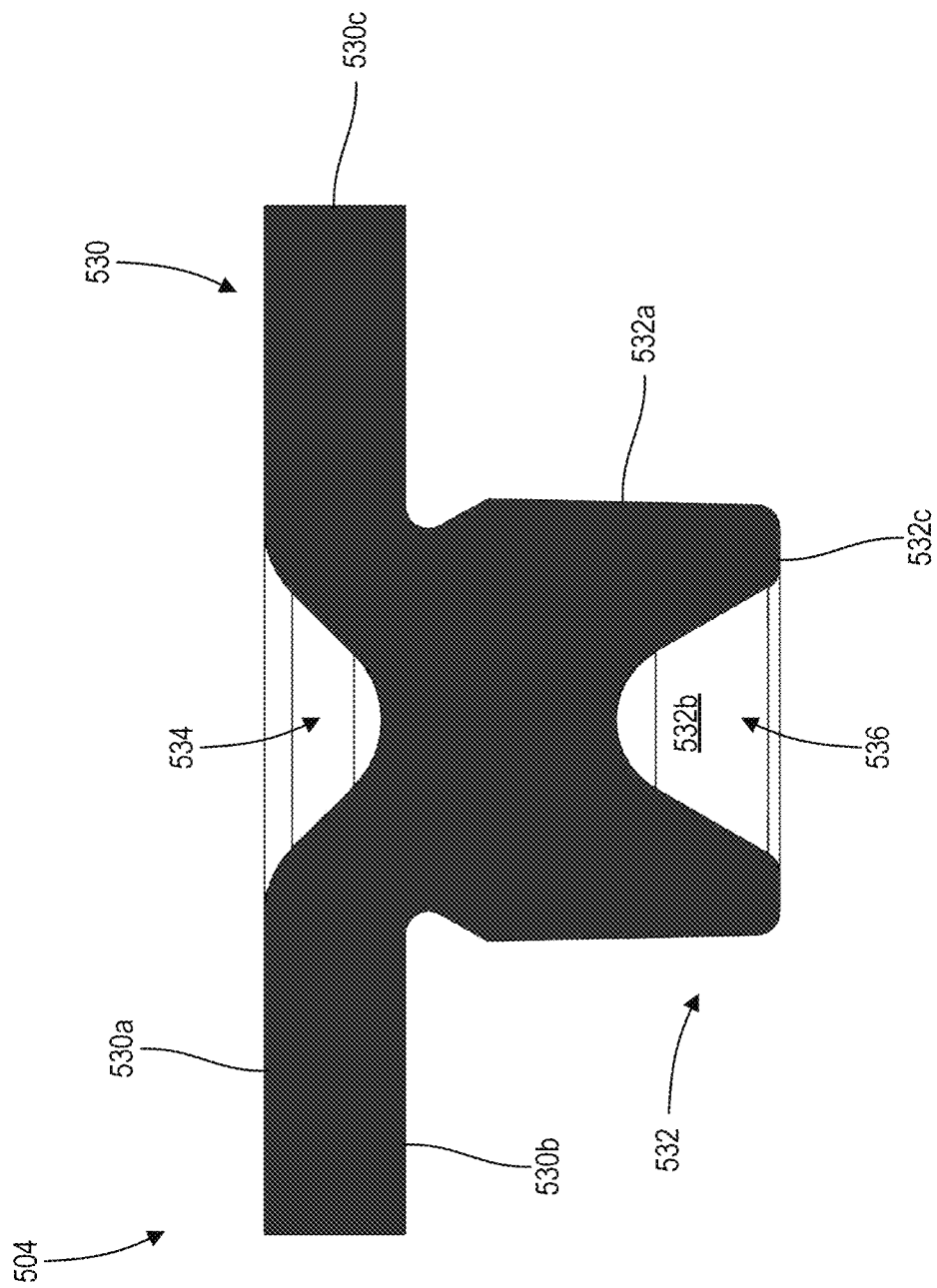

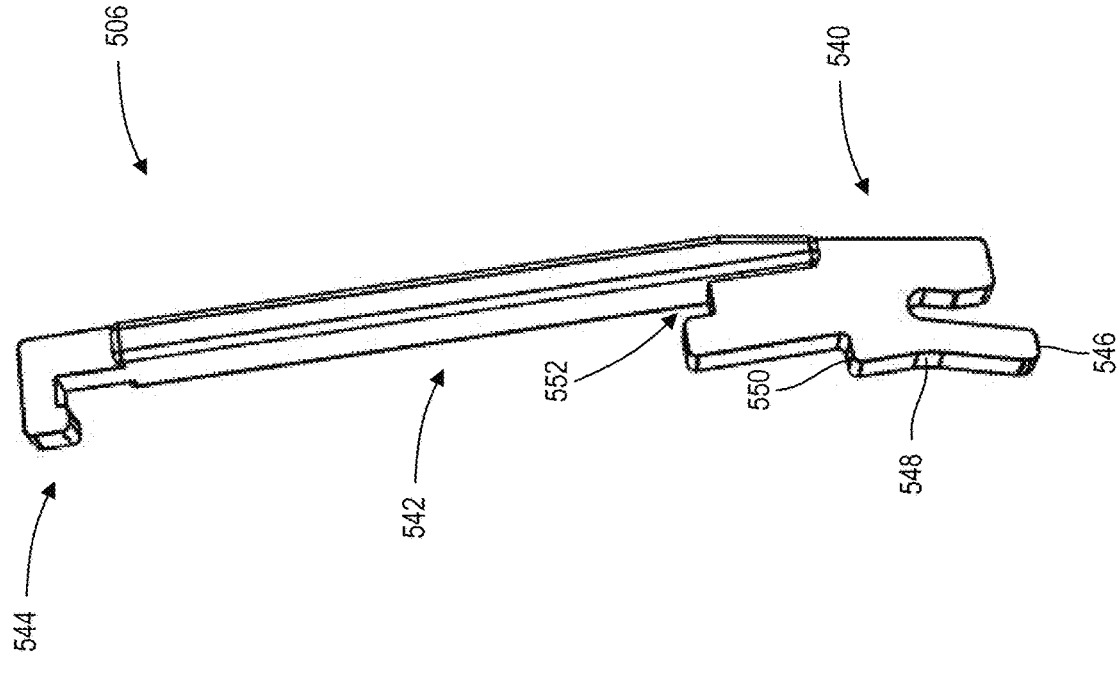
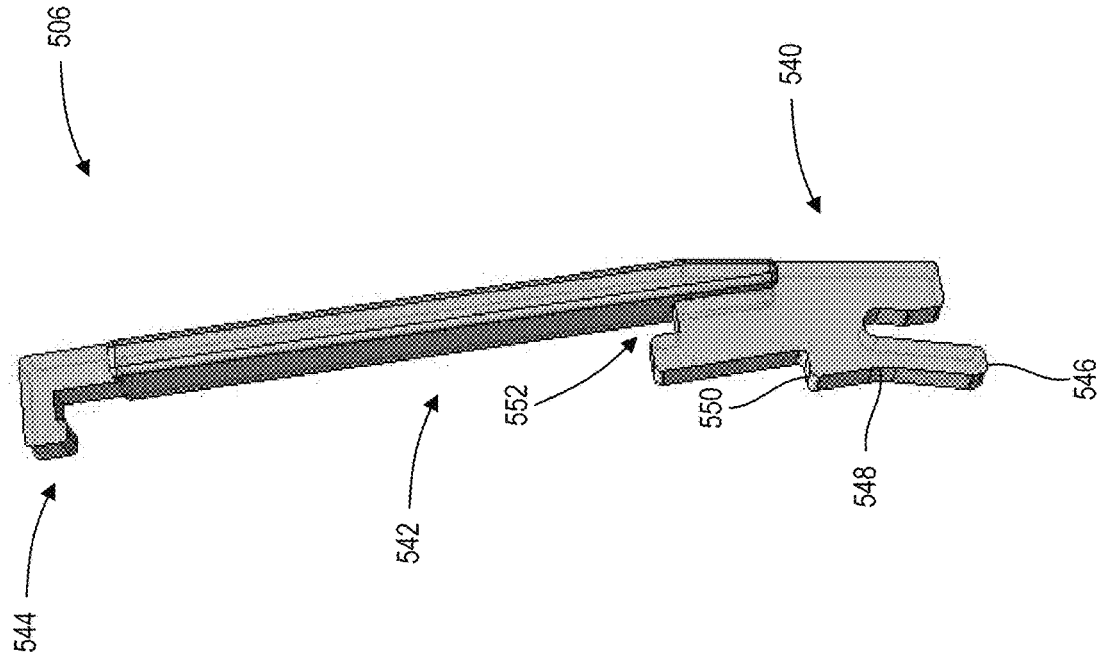

DERMAL PATCH FOR COLLECTING A PHYSIOLOGICAL SAMPLE WITH REMOVABLE VIAL

TECHNICAL FIELD

The present teachings are generally directed to dermal devices that can be employed to collect a physiological sample from a subject.

BACKGROUND

Biomarkers are increasingly employed for diagnosis of various disease conditions as well as for assessing treatment protocols. In many cases, it is important to monitor the level of a biomarker over time (e.g., to assess the progression of a disease). The temporal monitoring of biomarkers via conventional techniques includes drawing a physiological fluid sample from a subject. These techniques may be cumbersome and painful to the subject. For example, the invasive nature of drawing a blood sample from a subject can cause discomfort and may lead to less cooperation from a subject, especially children, rendering multiple measurements of a target analyte difficult.

Some recently developed devices that allow for continuous monitoring of a target analyte (e.g., glucose monitors), typically suffer from several shortcomings, such as low sensitivity and/or specificity. Therefore, there is still a need for devices that allow collection of a physiological sample (e.g., a blood sample) for monitoring a target analyte.

SUMMARY

Aspects of the present disclosure address the above-referenced problems and/or others.

In one aspect, a device (herein also referred to as a dermal patch) for collecting a physiological sample from a subject includes a lancet with a needle that is configured to puncture the subject's skin. The device further includes a cartridge that is configured to couple to the lancet. The lancet is configured to automatically deploy the needle when coupled to the cartridge, which in turn allows the needle to puncture the subject's skin and draw a physiological sample. The device also includes a vial disposed within the cartridge and configured to receive the drawn physiological sample. In some embodiments the vial is removable from the cartridge. In certain embodiments, the vial is configured to be placed into a centrifuge. In some embodiments, the vial includes a lysis buffer and/or a preservative and/or an anticoagulant.

In some embodiments, the device further includes a plunger that is at least partially disposed within the vial and is configured to create a vacuum within the vial and the cartridge, wherein the vacuum can draw the physiological sample into the vial. In certain embodiments, the cartridge further includes a physiological sample well, and a needle in open communication with the physiological sample well and configured to carry the physiological sample from the physiological sample well to the vial. In certain embodiments, the plunger includes a snap-off joint that allows a user to separate a portion of the plunger from the rest of the plunger. By way of example, the snap-off joint can be implemented, without limitation, as a reduced diameter portion, a notch, a perforation, among other structures.

In some embodiments the device further includes a self-healing cap coupled to the vial. In some embodiments the self-healing cap is configured to seal the vial after being punctured. In certain embodiments, the needle is configured to puncture the self-healing cap to carry the physiological sample to the vial. In some embodiments, the cartridge includes a cover, and a base removably coupled to the cover. In certain embodiments, the cover includes a vial viewing aperture configured to provide visual access to the vial disposed within the cartridge. In other embodiments, the device includes a quick response (QR) code disposed on an outer surface of the vial. In certain embodiments the cover includes a quick response code viewing aperture configured to provide visual access to the quick response code.

In another aspect, a method for obtaining a physiological sample from a subject includes attaching a cartridge of a dermal patch to the skin of a subject. The cartridge includes a vial disposed therein and a plunger at least partially disposed within the vial. The method also includes engaging a lancet having a needle to the cartridge so as to activate the needle for puncturing the skin so as to draw a physiological sample (e.g., a blood sample). The method further includes moving the plunger from a first position to a second position to facilitate drawing the physiological sample into the vial. In certain embodiments, the needle of the lancet automatically retracts into the lancet after drawing the physiological sample. In some embodiments the method further includes removing the vial from the cartridge, breaking the plunger at its snap-off joint such that a portion of the plunger remains disposed within the vial, placing the vial with the portion of the plunger into a medical device, and performing an analysis of the physiological sample within the vial via the medical device.

In some embodiments, the vial includes a lysis buffer or a preservative or an anticoagulant. In certain embodiments, the cartridge includes a physiological sample well and the drawn physiological sample pools within the physiological sample well and wherein moving the plunger from the first position to the second position draws the physiological sample from the physiological sample to the vial. In some embodiments, the cartridge or the vial includes a quick response code, and the method further includes scanning the quick response code to update an electronic medical record associated with the quick response code.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which:

FIGS. 10A and 10B-14A and 14B depict a cover of the cartridge in accordance with an exemplary embodiment of the present disclosure;

FIGS. 15A and 15B-20A and 20B depict a base of the cartridge in accordance with an exemplary embodiment of the present disclosure;

FIGS. 24A and 24B-27 depict a syringe for use with the cartridge in accordance with an exemplary embodiment of the present disclosure;

FIGS. 29A and 29B-33 depict the plunger in accordance with an exemplary embodiment of the present disclosure;

FIGS. 36A and 36B-FIGS. 44A and 44B depict a vial assembly in accordance with an exemplary embodiment of the present disclosure;

FIGS. 45A and 45B-52A and 52B depict a vial of the vial assembly in accordance with an exemplary embodiment of the present disclosure;

FIGS. 53 and 54 depict a cap of the vial assembly in accordance with an exemplary embodiment of the present disclosure;

FIGS. 55A and 55B depict a locking member of the vial assembly in accordance with an exemplary embodiment of the present disclosure;

DETAILED DESCRIPTION

Figure 1A:
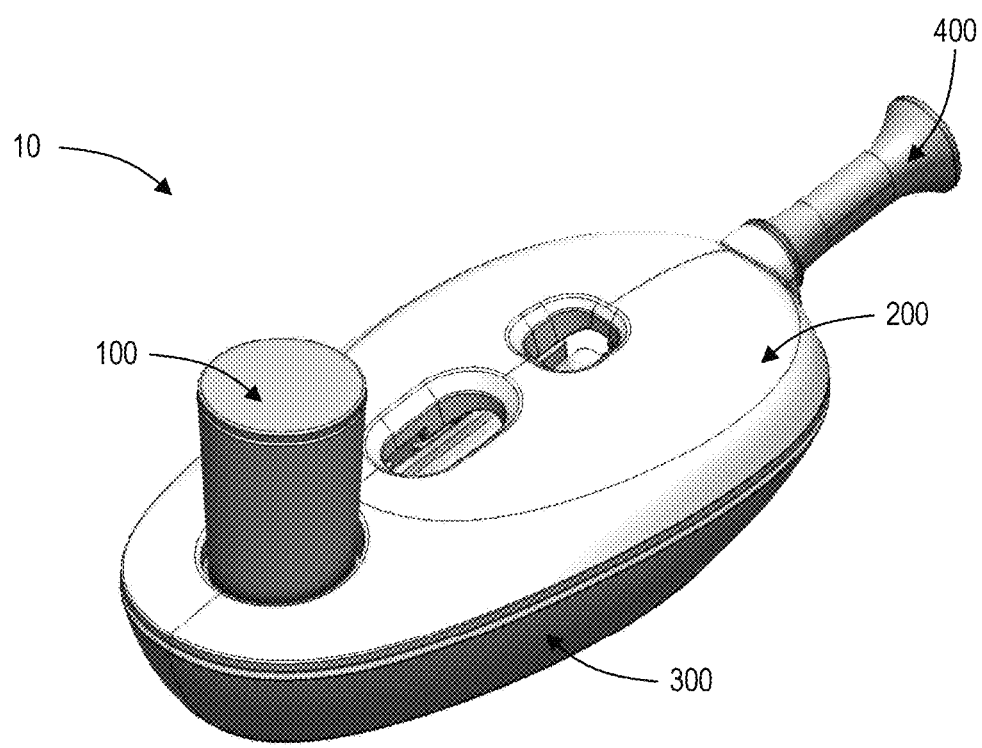
FIGS. 1A and 1B depict a dermal patch system in accordance with an exemplary embodiment of the present disclosure.

The present disclosure generally relates to a dermal patch that may be utilized to collect and/or store a collected physiological sample.

In some embodiments, a dermal patch may be used to collect a physiological sample and the collected sample may then be stored within a vial of the dermal patch. Dermal patches disclosed herein may allow for the collection and analysis of a physiological sample in a variety of environments (e.g., in the home, in the field, in a medical facility, etc.).

Various terms are used herein in accordance with their ordinary meanings in the art, unless otherwise indicated.

The term "about," as used herein, denotes a deviation of at most 10% relative to a numerical value. For example, about 100 μm means in the range of 90 μm-110 μm.

The term "substantially," as used herein, refers to a deviation, if any, of at most 10% from a complete state and/or condition.

The term "subject" as used herein refers to a human subject or an animal subject (i.e., chicken, pig, cattle, dog, cat, etc.).

The term "physiological sample," as used herein, includes fluid drawn from a subject and includes, but is not limited to, blood and interstitial fluid.

The term "lancet," as used herein refers broadly to an element that can be used to provide a passageway, or facilitate the production of a passageway, in the skin for the collection of a physiological sample.

The term "transparent," as used herein, indicates that light can substantially pass through an object (e.g., a window) to allow visualization of a material disposed behind the object. For example, in some embodiments, a transparent object allows the passageway of at least 70%, or at least 80%, or at least 90% of visible light therethrough.

The term "vacuum," as used herein, refers to a pressure less than atmospheric pressure and more particularly to a pressure that can facilitate the movement of a fluid (e.g., a physiological sample) within a dermal patch.

The term "syringe" as used herein, refers to a device that includes a hollow barrel (also referred to as a "vial" herein) that is fitted with a plunger. A syringe may or may not include a needle.

The term "needle" as used herein, refers to a component with a pointed tip that is configured to pierce an outer surface of an element (e.g., skin of a subject) to provide a passageway.

The term "pipette" as used herein refers to an apparatus for collecting a liquid that consists of a narrow tube and a barrel that retains the liquid. Liquid may travel into the barrel via the suction or capillary action and as such, a pipette may or may not include a bulb.

The present disclosure generally relates to a device, which is herein also referred to as a dermal patch or a dermal patch system, for collecting a physiological sample (e.g., bodily fluids such as blood, interstitial fluids, etc.) from a subject. In some embodiments discussed below, such a dermal patch system can include a cartridge that can be affixed to a to a subject's skin (e.g., via an adhesive layer) and a separate lancet that can be engaged with the cartridge to puncture the skin, thereby providing a passageway for extracting the physiological sample. As discussed in more detail below, the lancet can include a housing in which at least one needle that is configured for puncturing the skin is disposed. The lancet can further include a mechanism that can be transitioned between at least two states, wherein in one state (herein referred to as a locked state), the mechanism retains the needle within the lancet in an undeployed position when the lancet is not engaged with the cartridge and in another state (herein referred to as a released state), the mechanism allows the needle to be deployed for puncturing the skin in response to engagement of the lancet with the cartridge. In other words, the engagement of the lancet with the cartridge transitions the mechanism from the locked state to the released state, where in the released state, the mechanism allows the needle to be deployed for puncturing the skin. For example, in some embodiments, the mechanism can include an upper locking portion that can retain an upper spring that is coupled to a needle platform (to which a needle is mounted) in a compressed state, thereby preventing the needle from transitioning into a deployed position. Further, the mechanism can include an upper interference member that prevents the movement of the needle platform when the mechanism is in the locked state.

Hence, the engagement of the lancet with the cartridge results in an automatic transition of the mechanism from the locked state to the released state, which transitions the needle into a deployed position in which the needle extends beyond the lancet and the cartridge housing to puncture the subject's skin. In some embodiments, the engagement of the lancet with the cartridge causes the upper locking member to release the needle platform, which in turn allows the upper spring to decompress and thus push down the needle platform thereby deploying the needle. In some embodiments, the mechanism can further include a lower interference member that restricts the downward movement of the needle platform, when the needle platform is released. In this manner the extent of the penetration of the needle into the skin can be controlled. In certain embodiments, the mechanism can also include a lower locking member that retains a lower spring in a compressed state. The downward movement of the needle platform can cause the release of the lower locking member to allow the lower spring to decompress and exert a force on the needle platform to cause the retraction of the needle into the lancet housing.

In this manner, the lancet remains safe before it is engaged with the cartridge as the lancet is not capable of deploying the needle when the lancet is not engaged with the cartridge. Furthermore, in this manner, the lancet remains safe after drawing a physiological sample as the needle automatically retracts back into the lancet after being deployed.

Figure 1B:
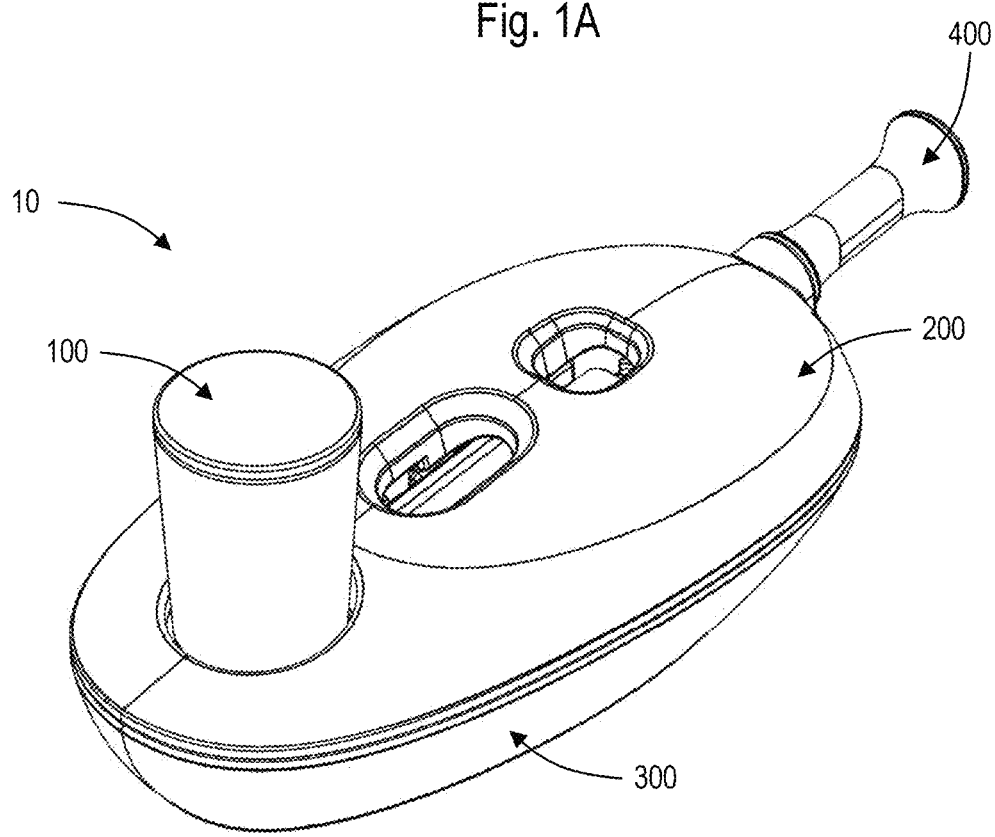

Referring now to FIGS. 1A and 1B, a dermal patch system 10 is shown in accordance with an exemplary embodiment. The dermal patch system 10 includes a lancet 100, a cartridge 12 that can be affixed to a subject's skin via an adhesive layer 14 (FIGS. 9A and 9B), and a syringe 16 (FIGS. 24A and 24B-27) that can be at least partially disposed within the cartridge 12. As will be discussed in further detail herein, the lancet 100 can engage with the cartridge 12 to deploy a needle disposed within the lancet housing to puncture the subject's skin thereby drawing a physiological sample from the subject.

Figure 2:
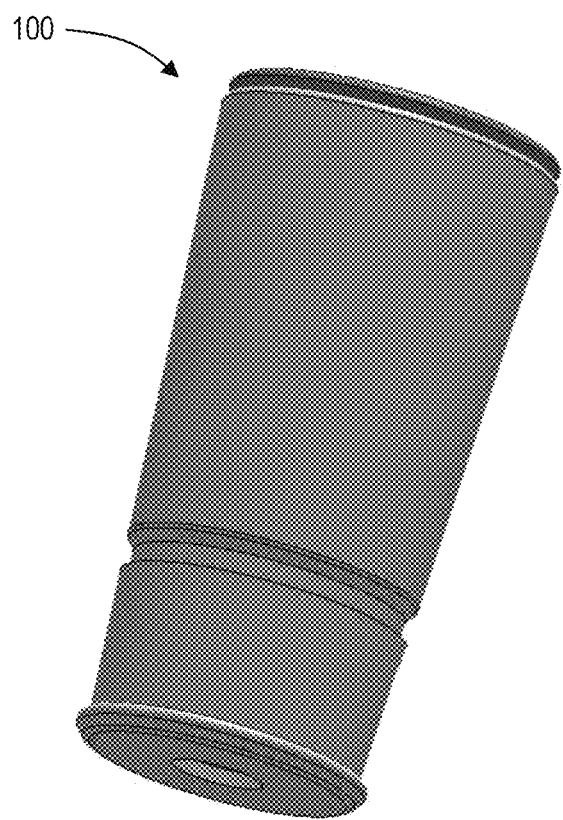
FIGS. 2 and 3 depict a lancet of the dermal patch system in accordance with an exemplary embodiment of the present disclosure
Figure 3:
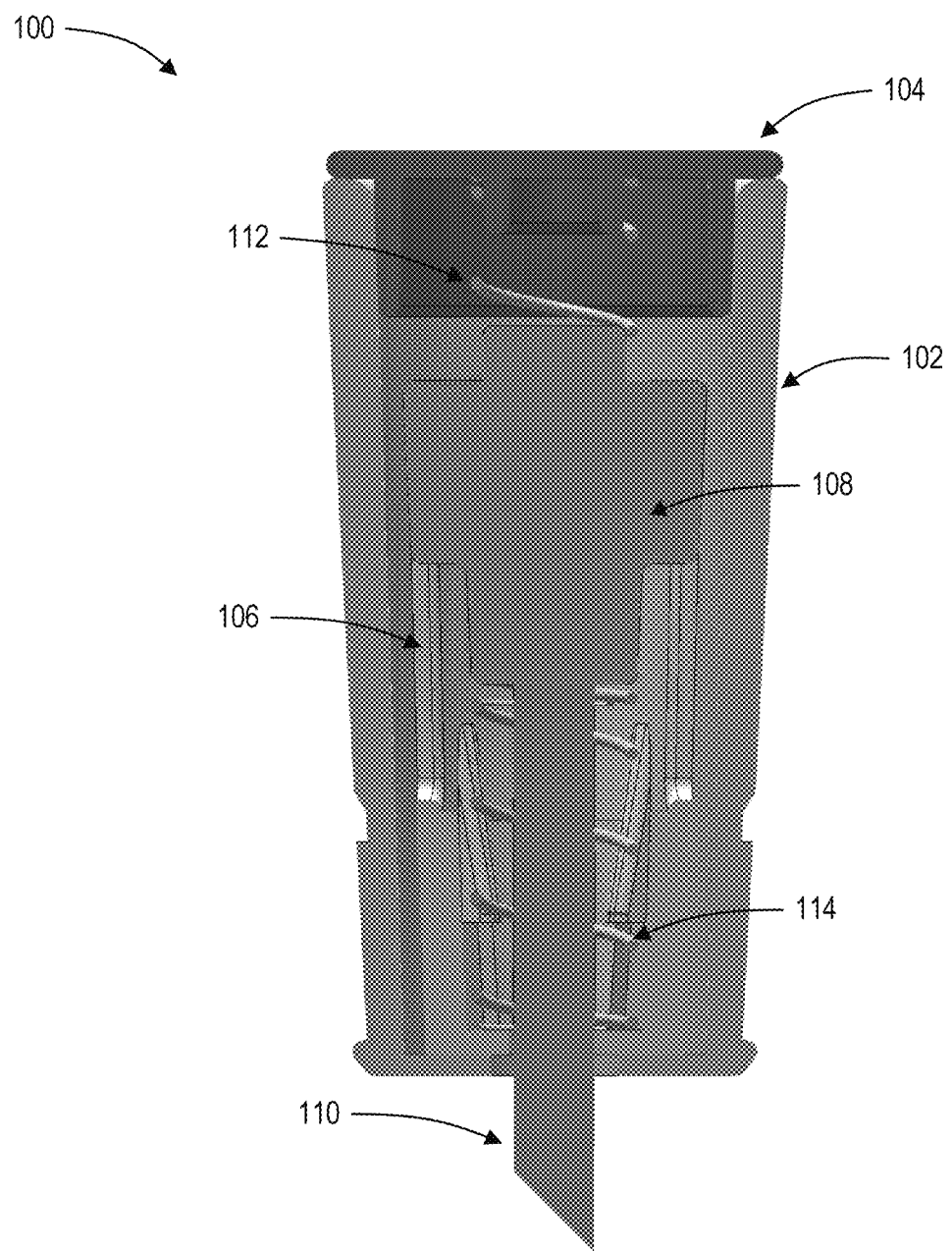

Referring now to FIGS. 2 and 3, the lancet 100 is shown in accordance with an exemplary embodiment. The lancet 100 includes a housing 102 in which various components of the lancet are disposed and a cap 104 that is coupled to the housing 102. The lancet 100 can further include an inner sleeve 106 within the housing 102 and a needle frame 108 that is disposed within the inner sleeve 106 and onto which a needle 110 is mounted. The lancet 100 also can include an injection spring 112 and a retraction spring 114 that move a needle of the lancet between various positions.

Figure 4B:
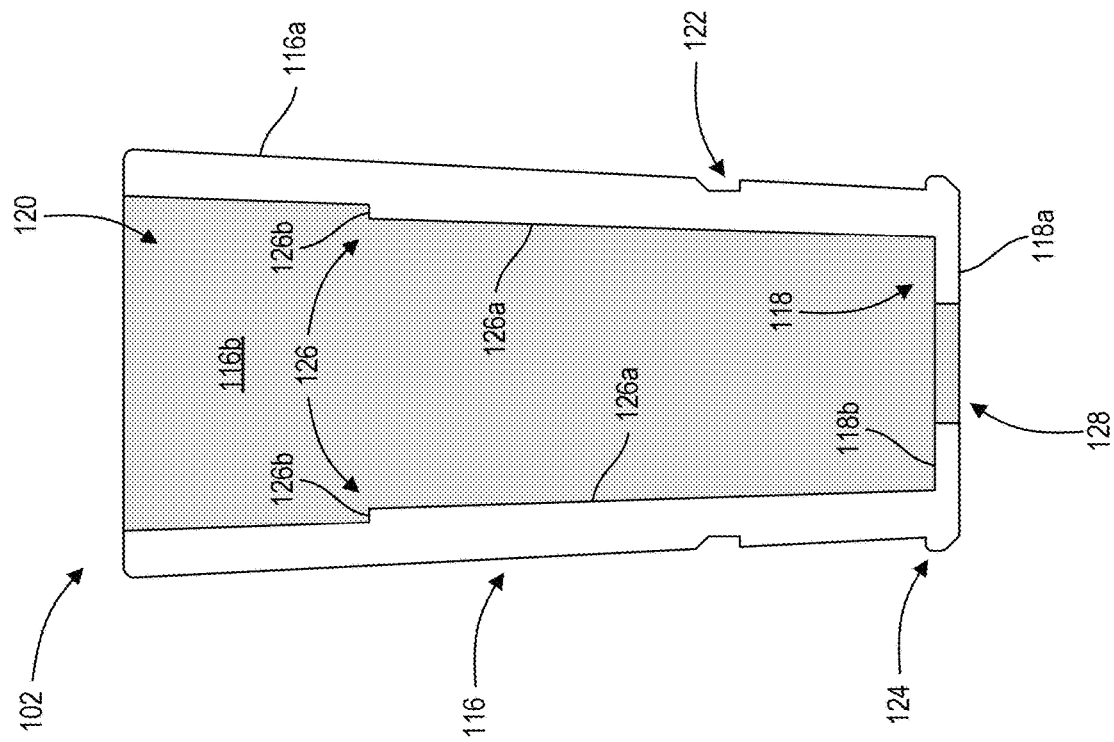
FIGS. 4A and 4B depict a housing of the lancet in accordance with an exemplary embodiment of the present disclosure.
Figure 4A:
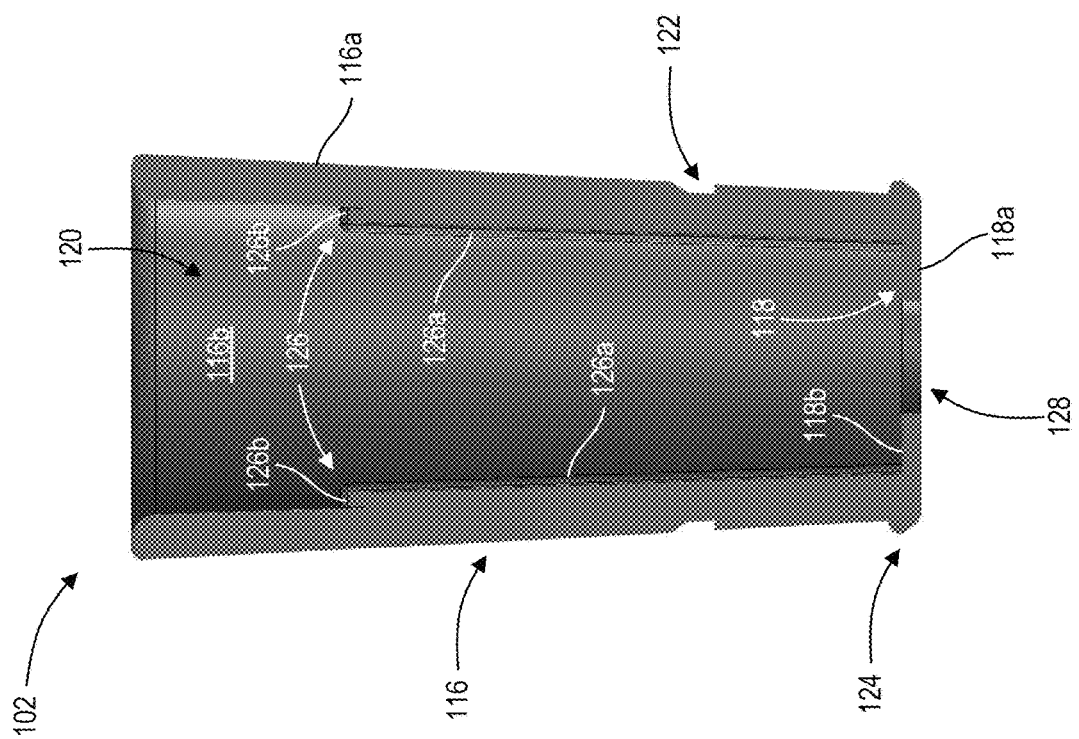

With particular reference to FIGS. 4A and 4B, the housing 102 includes a side wall 116 and a bottom wall 118. The side wall 116 includes an outer surface 116a and an opposed inner surface 116b. The bottom wall 118 includes an outer surface 118a and an opposed inner surface 118b. The side wall 116 extends vertically from the bottom wall 118. The side wall 116 has a generally cylindrical shape and the bottom wall 118 is generally circular in shape and is concentric relative to a longitudinal axis of the generally cylindrical side wall and covers a lower opening formed by the generally cylindrical side wall. The inner surface 116b of the side wall 116 and the inner surface 118b of the bottom wall 118 define an inner volume 120.

The outer surface 116a defines a notch 122 that extends circumferentially around the outer surface 116a of the side wall 116. As will be discussed in further detail herein, the notch 122 is shaped and dimensioned to couple to a locking member of the cartridge 12 via a snap fit. The housing 102 further includes a rim 124 that extends circumferentially around the outer surface 116a of the side wall 116. The inner surface 116b defines a first and second column 126 that extend vertically from the inner surface 118b of the bottom wall 118. The columns 126 includes an inner surface 126a and a top surface 126b. The inner surface 126a extends vertically between the inner surface 118b of the bottom wall 118 and the top surface 126b. The top surface 126b extends longitudinally between the inner surface 116b of the side wall 116 and the inner surface 126a.

As will be discussed in further detail herein, before the lancet 100 is inserted into the cartridge 12 the columns 126 retain the needle 110 of the lancet 100 in an undeployed position.

The bottom wall 118 defines an aperture 128 that extends through the bottom wall 118. Stated another way, the aperture 128 extends between the outer surface 118a and the inner surface 118b of the bottom wall 118. As will be discussed in further detail herein, when the lancet is activated via engagement with the cartridge 12, the needle of the lancet 100 is activated to extend through the aperture 128 and puncture the subject's skin thereby providing a passageway through which a physiological sample can be drawn from a subject.

Figure 5A:
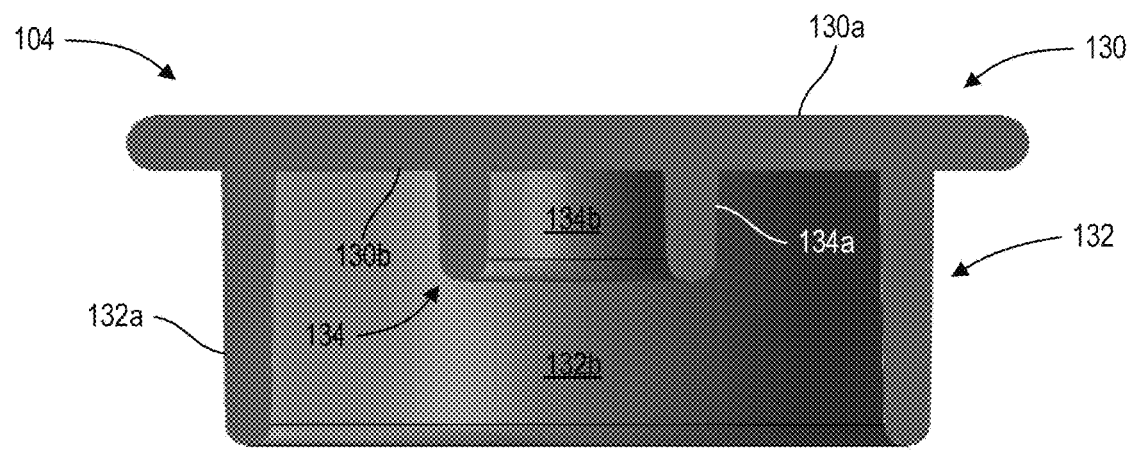
FIGS. 5A and 5B depict a cap of the lancet in accordance with an exemplary embodiment of the present disclosure.
Figure 5B:
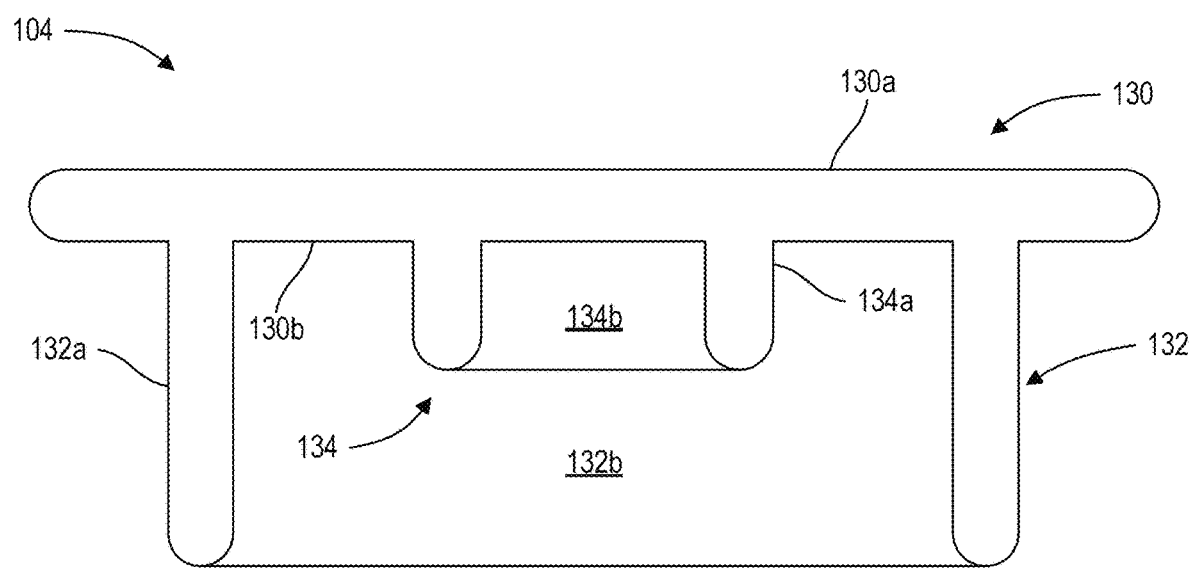

With particular reference to FIGS. 5A and 5B the cap 104 includes a top wall 130 with an outer surfaced 130a and an opposed inner surface 130b. The cap 104 also includes a side wall 132 with an outer surface 132a and an opposed inner surface 132b. The top wall 130 extends longitudinally from and perpendicular to the side wall 132. The side wall 132 extends vertically from and perpendicular to the top wall 130. The top wall 130 and the side wall 132 are generally circular in shape and are concentric with one another. The cap 104 also includes an inner cylinder 134 with an outer surface 134a and an opposed outer surface 134b. The inner cylinder 134 extends vertically from and perpendicular to the top wall 130. The inner cylinder 134 is concentric with the top wall 130 and the side wall 132.

When the cap 104 is coupled to the housing 102 the side wall 132 extends into the inner volume 120 of the housing 102 and at least a portion of the side wall 132 contacts the inner surface 116b of the side wall 116 such that the cap 104 couples to the housing 102 via an interference fit.

Figure 6:
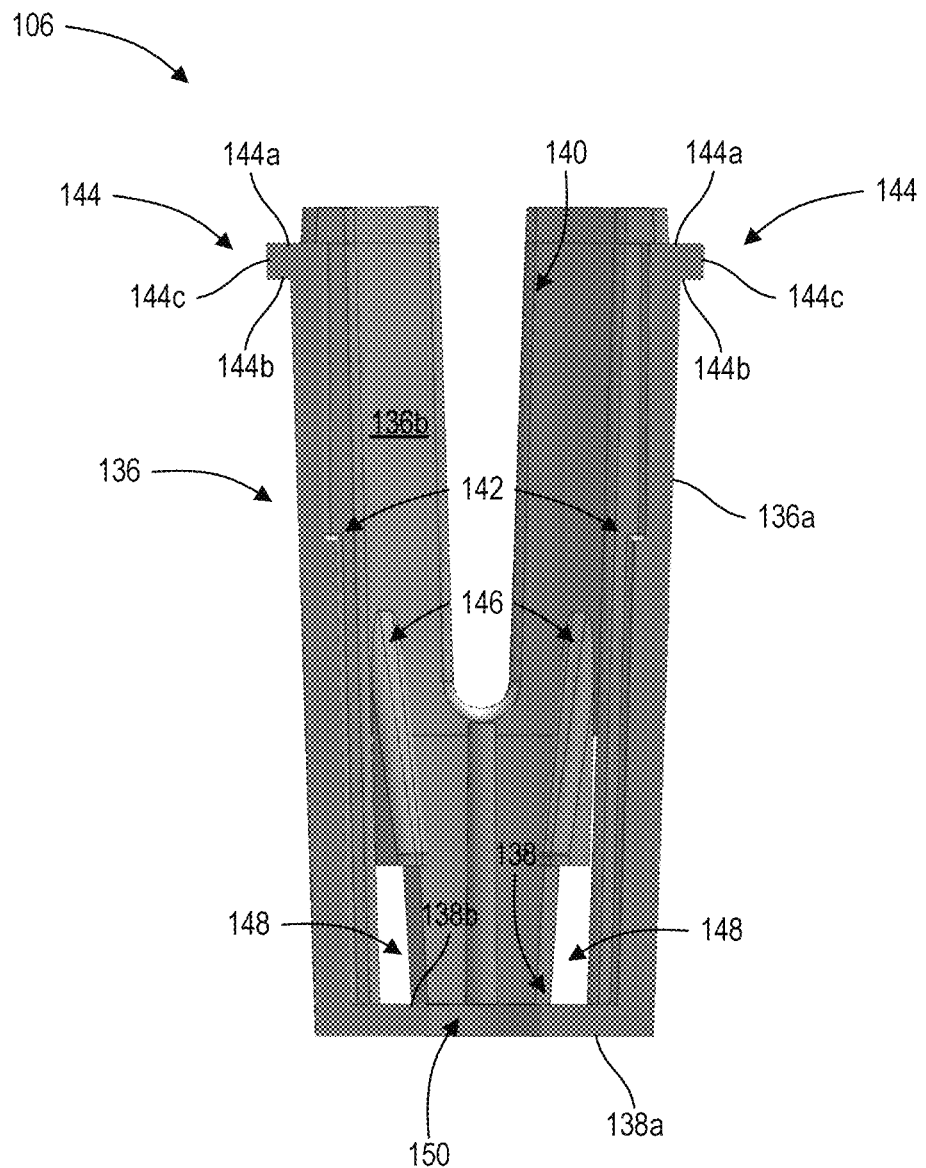
FIG. 6 depicts an inner sleeve of the lancet in accordance with an exemplary embodiment of the present disclosure.

As depicted in FIG. 6, the inner sleeve 106 includes a side wall 136 and a bottom wall 138. The side wall 136 includes an outer surface 136a and an opposed inner surface 136b. The bottom wall 138 includes an outer surface 138a and an opposed inner surface 138b. The side wall 136 extends vertically from the bottom wall 138. The side wall 136 and the bottom wall 138 are generally circular in shape and are concentric with one another. The inner surface 136b of the side wall 136 and the inner surface 138b of the bottom wall 138 define an inner volume 140. The inner surface 136b defines a plurality of columns 142 each of which extends vertically from and perpendicular to the inner surface 138b of the bottom wall 138. As will be discussed in further detail herein, when the needle frame 108 is in a deployed position, a portion of the needle frame 108 rests upon the columns 142.

The inner sleeve 106 further includes a plurality of ledges 144 that extend circumferentially about the side wall 136. Each ledge 144 includes a top surface 144a, an opposed bottom surface 144b and an outer surface 144c that extends between the top surface 144a and the bottom surface 144b. The inner sleeve 106 also includes a plurality of locking members 146 that extend from the inner surface 136b of the side wall 136. As will be discussed in further detail herein, the proximal end of the locking members 146 retains the retraction spring 114 in a compressed state in absence of engagement between the lancet 100 and the cartridge 12. The side wall 136 further defines a plurality of openings 148 that extend through the side wall 136. Stated another way, the openings 148 extend between the outer surface 136a and the inner surface 136b of the side wall 136. Each of the openings 148 are aligned with a proximal end of a locking member 146 to allow the proximal end of a locking member 146 to extend therethrough.

The bottom wall 138 defines an aperture 150 that extends through the bottom wall 138. Stated another way, the aperture 150 extends between the outer surface 138a and the inner surface 138b of the bottom wall 138. The aperture 150 is concentric with the aperture 128 of the housing 102. As will be discussed in further detail herein, when in a deployed position, the needle 110 of the lancet 100 extends through the aperture 150 of the inner sleeve 106 as well as the aperture 128 of the housing 102.

Figure 7:
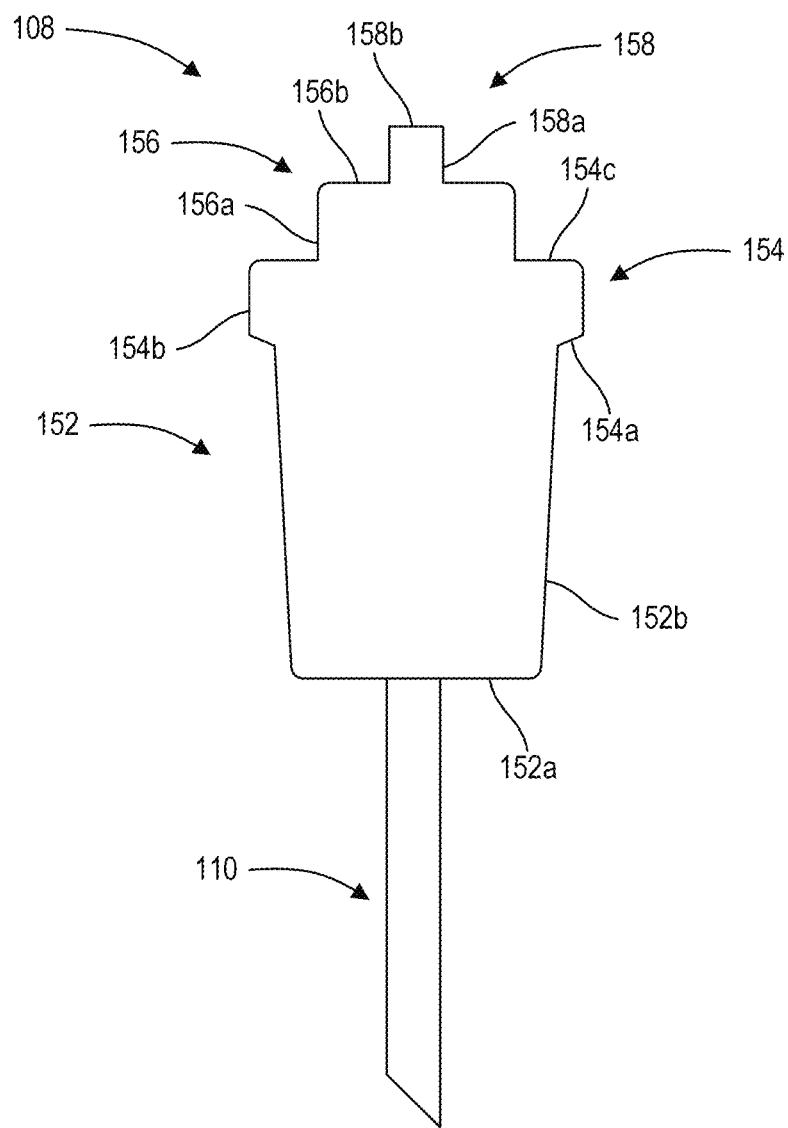
FIG. 7 diagrammatically depicts a needle frame of the lancet in accordance with an exemplary embodiment of the present disclosure.
Figure 8A:
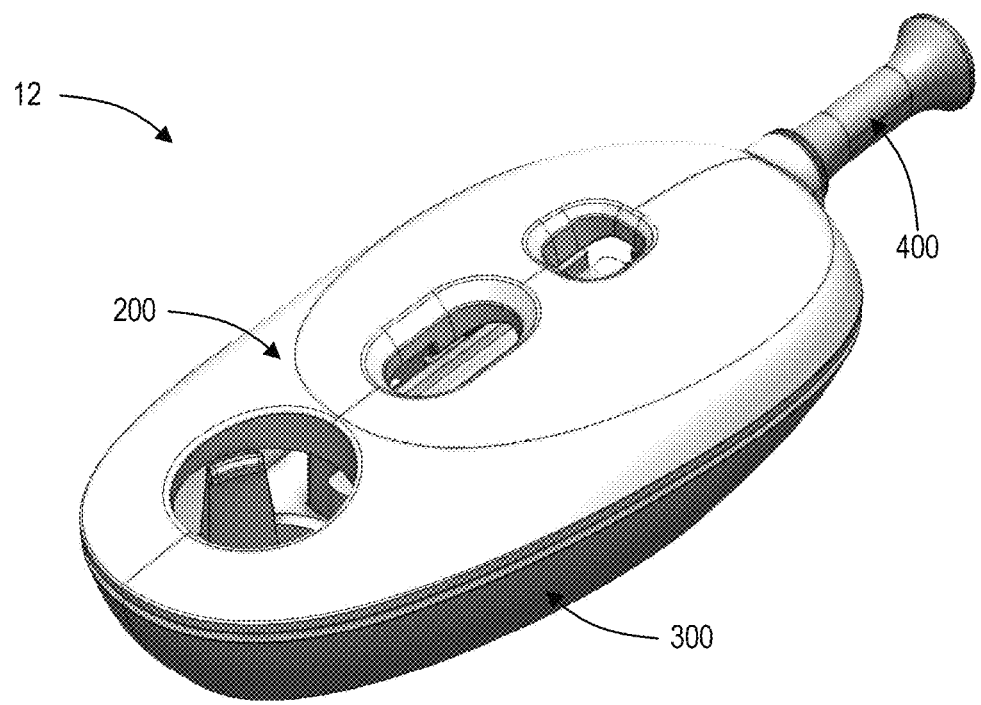
FIGS. 8A, 8B, 9A, and 9B depict a cartridge of the dermal patch system in accordance with an exemplary embodiment of the present disclosure.
Figure 8B:
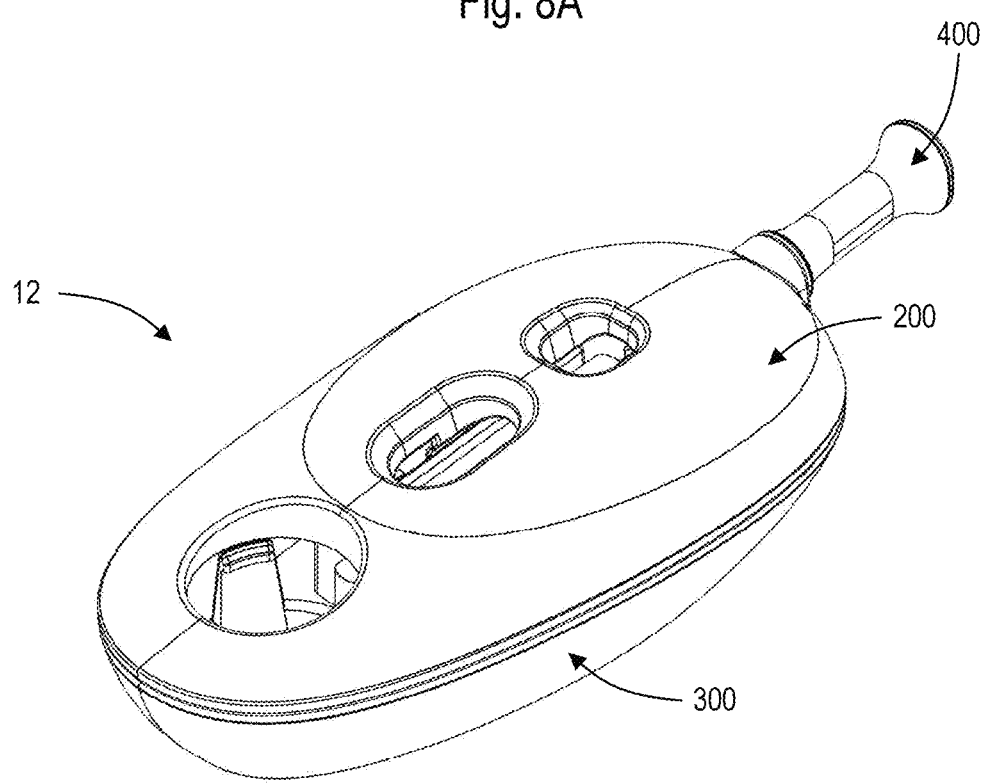

As depicted in FIG. 7, the needle frame 108 includes a first cylinder 152 and a second cylinder 154 disposed vertically above the second cylinder 154c. The first cylinder 152 includes a bottom surface 152a and an outer surface 152b. The second cylinder 154c is disposed vertically above the first cylinder 152 and the third cylinder 156 is disposed vertically above the second cylinder 154. The first cylinder 152 includes a bottom surface 152a and an outer surface 152b and the second cylinder 154 includes a bottom surface 154a, an outer surface 154b and a top surface 154c. The third cylinder 156 includes an outer surface 156a and a top surface 156b. Similarly, the protrusion 158 includes an outer surface 158a and a top surface 158b.

The bottom surface 152a of the first cylinder 152 extends circumferentially about the outer surface 152b of the first cylinder. The outer surface 152b of the first cylinder 152 extends vertically between the bottom surface 152a of the first cylinder 152 and the bottom surface 154a of the second cylinder 154. The bottom surface 154a of the second cylinder 154 extends at an angle longitudinally between the outer surface 152b of the first cylinder and the outer surface 154b of the second cylinder 154. The outer surface 154b extends vertically between the bottom surface 154a and the top surface 154c of the second cylinder 154. The top surface 154c of the second cylinder 154 extends longitudinally between the outer surface 154b of the second cylinder and the outer surface 156a of the third cylinder 156. The outer surface 156a extends vertically between the top surface 154c of the second cylinder and the top surface 156b of the third cylinder. The top surface 156b of the third cylinder extends longitudinally between the outer surface 156a of the third cylinder 156 and the outer surface 158a of the protrusion 158. The outer surface 158a extends vertically between the top surface 156b of the third cylinder and the top surface 158b of the protrusion 158. The top surface 158b of the protrusion 158 extends across a proximal end of the outer surface 158a.

The injection spring 112 extends vertically between the cap 104 and the needle frame 108. More specifically, a distal end of the injection spring 112 contacts the inner surface 130b of the top wall 130 and a proximal end of the injection spring 112 contacts the top surface 154c of the second cylinder 154. The distal end of the injection spring 112 extends circumferentially around the outer surface 134a of the inner cylinder 134. The proximal end of the injection spring 112 extends circumferentially around the third cylinder 156 and around the protrusion 158.

The needle frame 108 supports the needle 110. In some embodiments, the needle 110 is molded into the first cylinder 152 or is attached to the bottom surface 152a of the first cylinder 152 (e.g., via an adhesive).

Referring now to FIGS. 8A, 8B, 9A, and 9B, the cartridge 12 is shown in accordance with an exemplary embodiment.

The cartridge 12 includes a cover 200 and a base 300 that can couple to the cover 200. For example, the cover 200 and the base 300 can be formed as two separate components that are removably coupled to one another (e.g., via a snap fitting). In other embodiments, the cover 200 and the base 300 form an integral unitary cartridge 12. In some of these embodiments, the cover 200 can be coupled to the base 300 via an adhesive, laser welding, etc. The dermal patch system 10 also includes the syringe 16. The syringe 16 includes a plunger 400 and a vial assembly 500 that is coupled to the plunger 400. As will be discussed in further detail herein, the plunger is configured to create vacuum within the vial assembly 500 and the cartridge 12.

The cartridge 12 may be formed using a variety of suitable materials including, but not limited to, polymeric materials (e.g., polyolefins, polyethylene terephthalate (PET), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, photocross linkable polymers, etc.). In some embodiments, some of the cover 200 may be formed of poly(dimethylsiloxane) (PDMS) to allow visibility of components disposed within the cartridge 12.

Referring now to FIGS. 10A and 10B-14A and 14B, the cover 200 is shown in accordance with an exemplary embodiment. In this embodiment, the cover 200 includes a lid 202 with an outer surface 202a and an opposed inner surface 202b.

The lid 202 defines a U-shaped opening 204. The U-shaped opening 204 extends through the lid 202. Stated another way, the U-shaped opening 204 extends between the outer surface 202a and the inner surface 202b of the lid 202. The U-shaped opening 204 is shaped and dimensioned to accommodate at least a portion of the plunger 400. As will be discussed in further detail herein, U-shaped opening 204 allows the plunger 400 to be disposed within the cartridge 12. That is, the U-shaped opening 204 is shaped to accommodate the plunger 400 such that at least a portion of the plunger 400 can extend through the lid 202 to be disposed within in the cartridge 12.

The lid 202 defines a lancet aperture 206 that is generally circular in shape. The lancet aperture 206 extends through the lid 202. Stated another way, the lancet aperture 206 extends between the outer surface 202a and the inner surface 202b of the lid 202. The lancet aperture 206 is shaped to accommodate at least a portion of the lancet 100. As will be discussed in further detail herein, the lancet aperture 206 allows the lancet 100 to couple to the base 300. That is, the lancet aperture 206 is shaped to accommodate the lancet 100 such that at least a portion of the lancet 100 can extend through the lid 202.

Figure 9A:
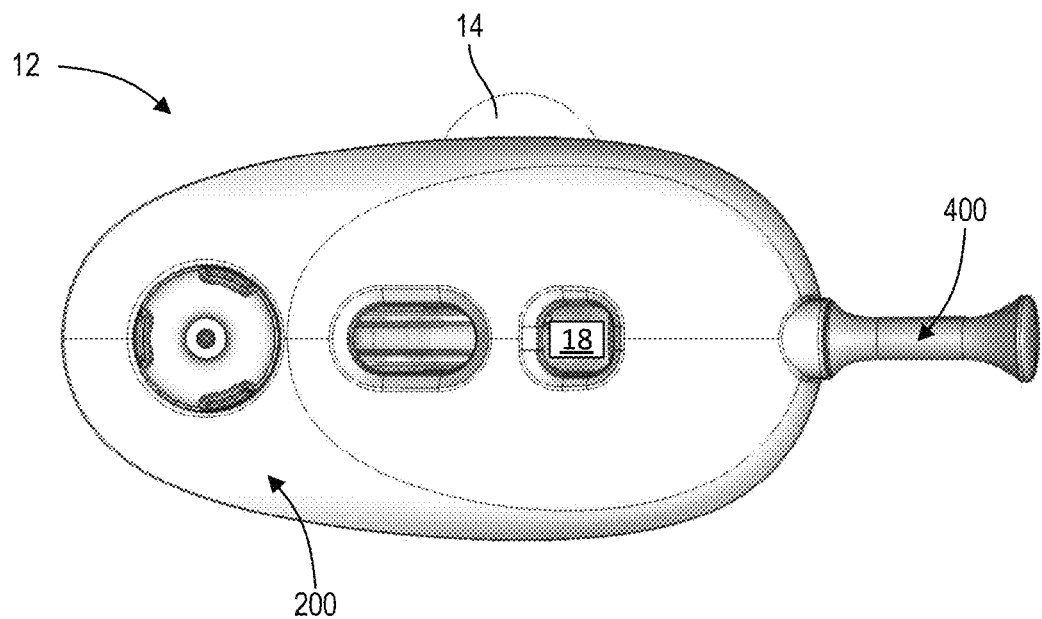
Figure 9B:
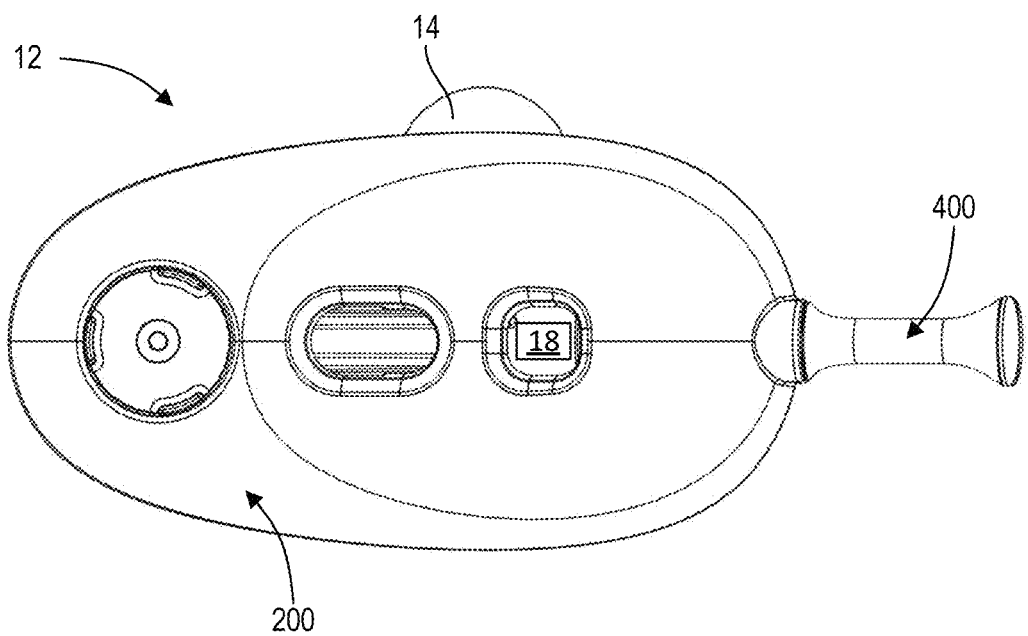
Figure 10A:
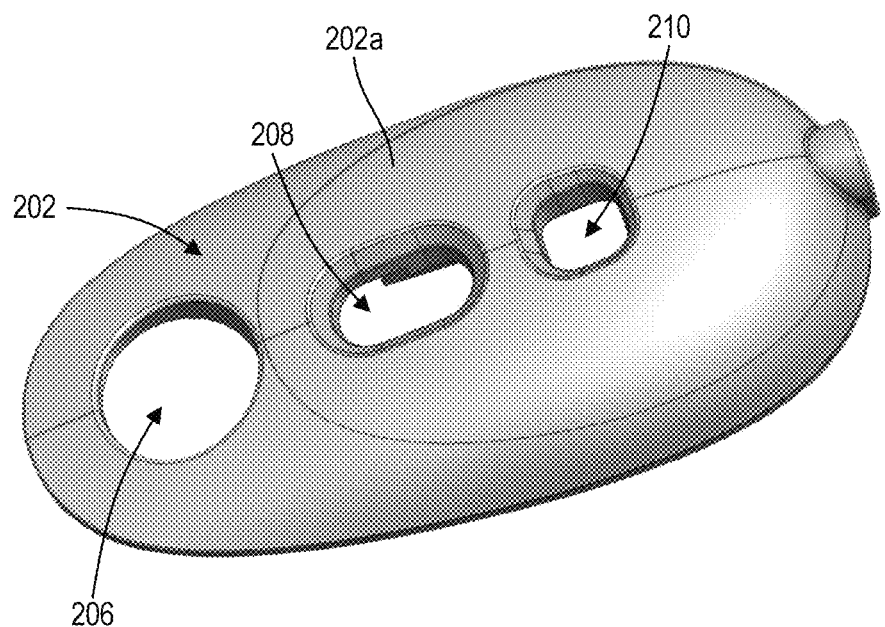
Figure 10B:
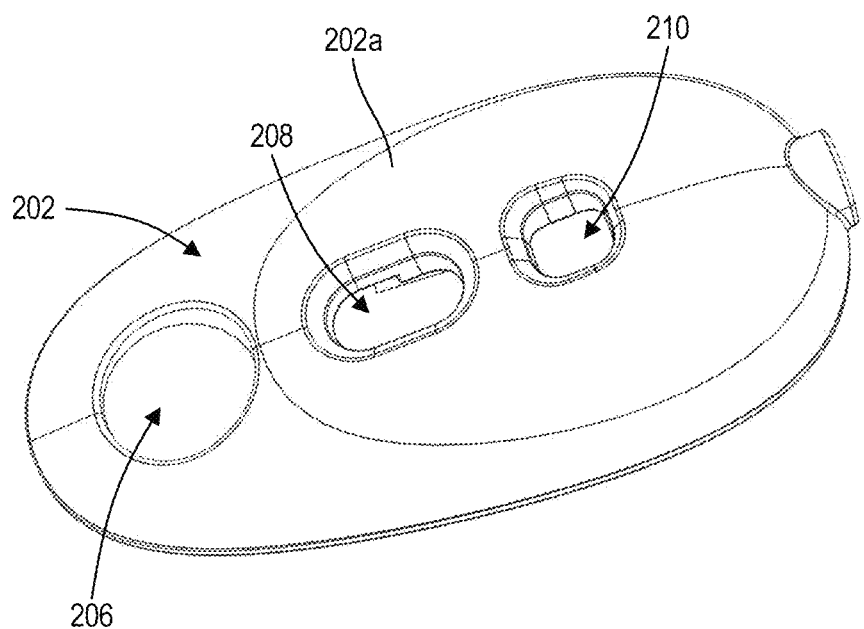
Figure 13A:
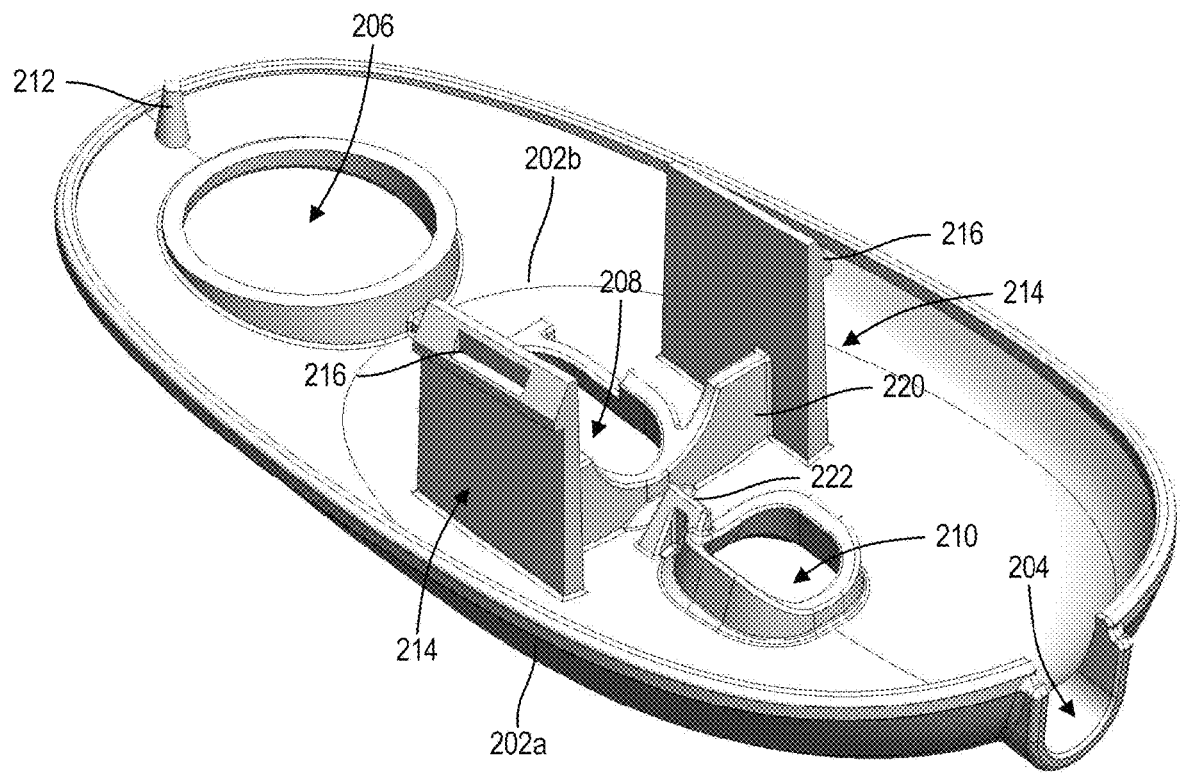
Figure 13B:
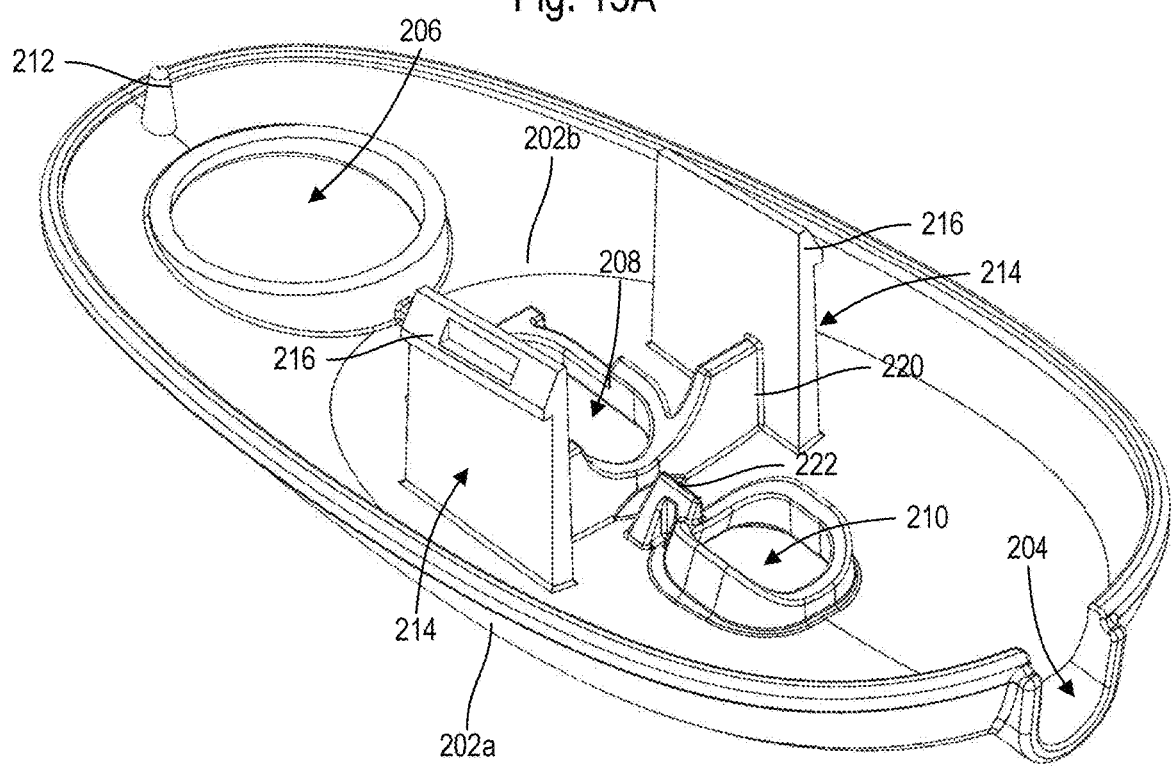
Figure 14B:
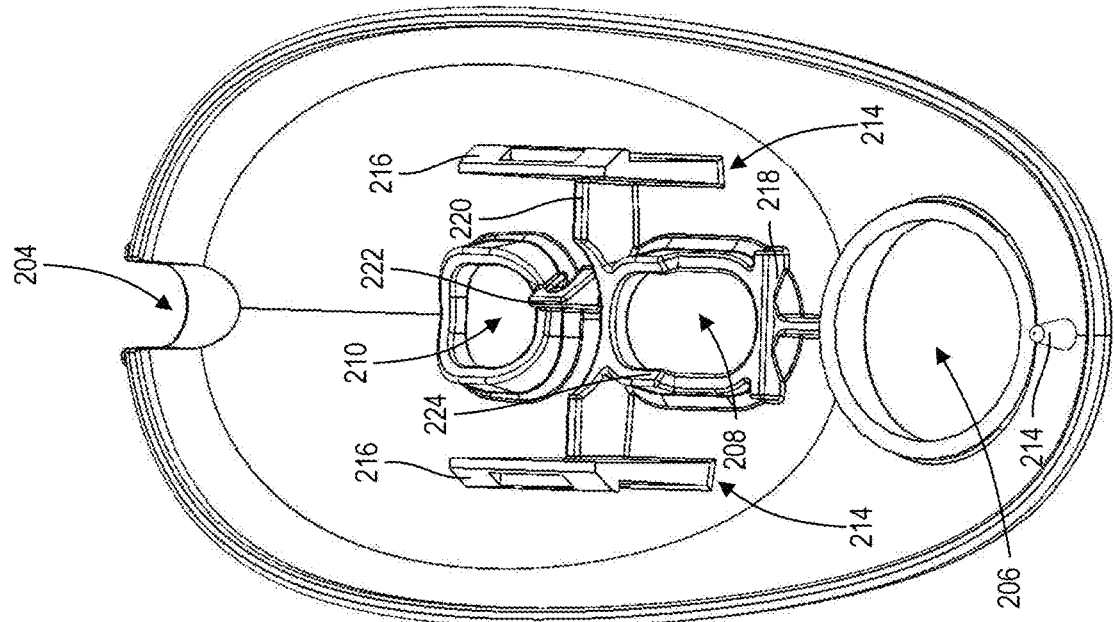
Figure 14A:
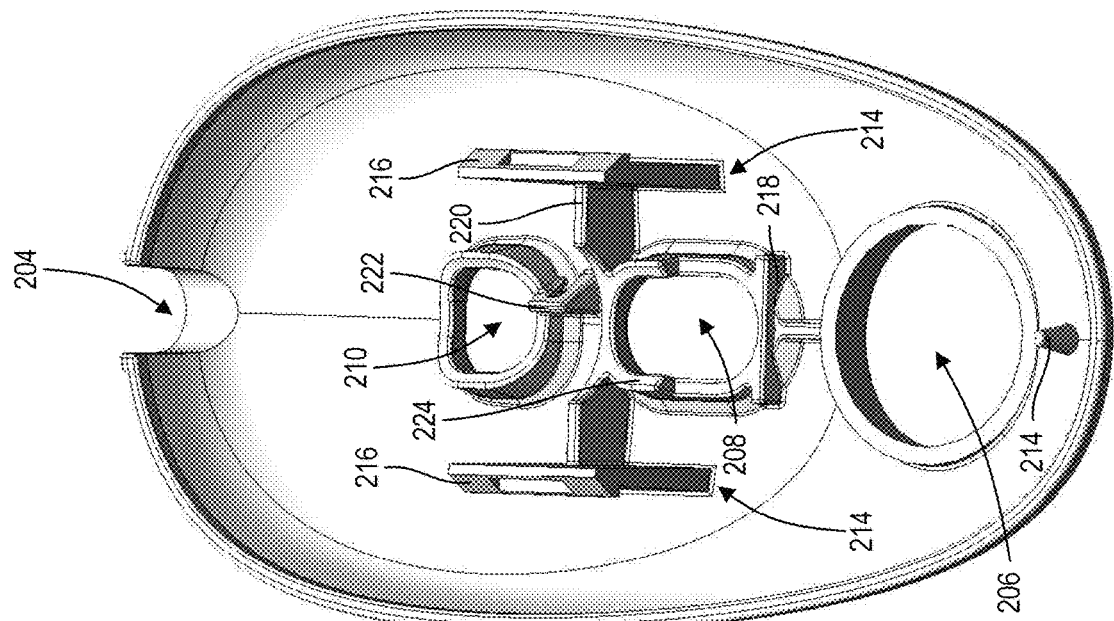
Figure 15A:
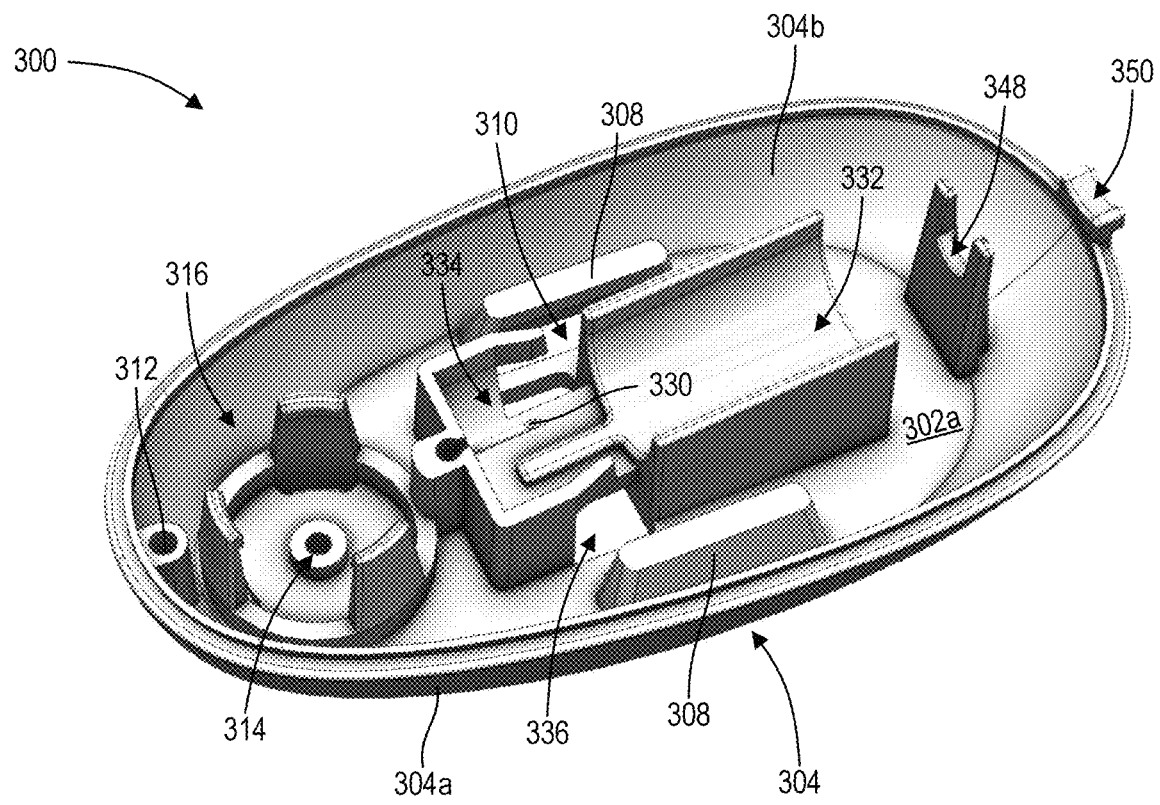
Figure 15B:
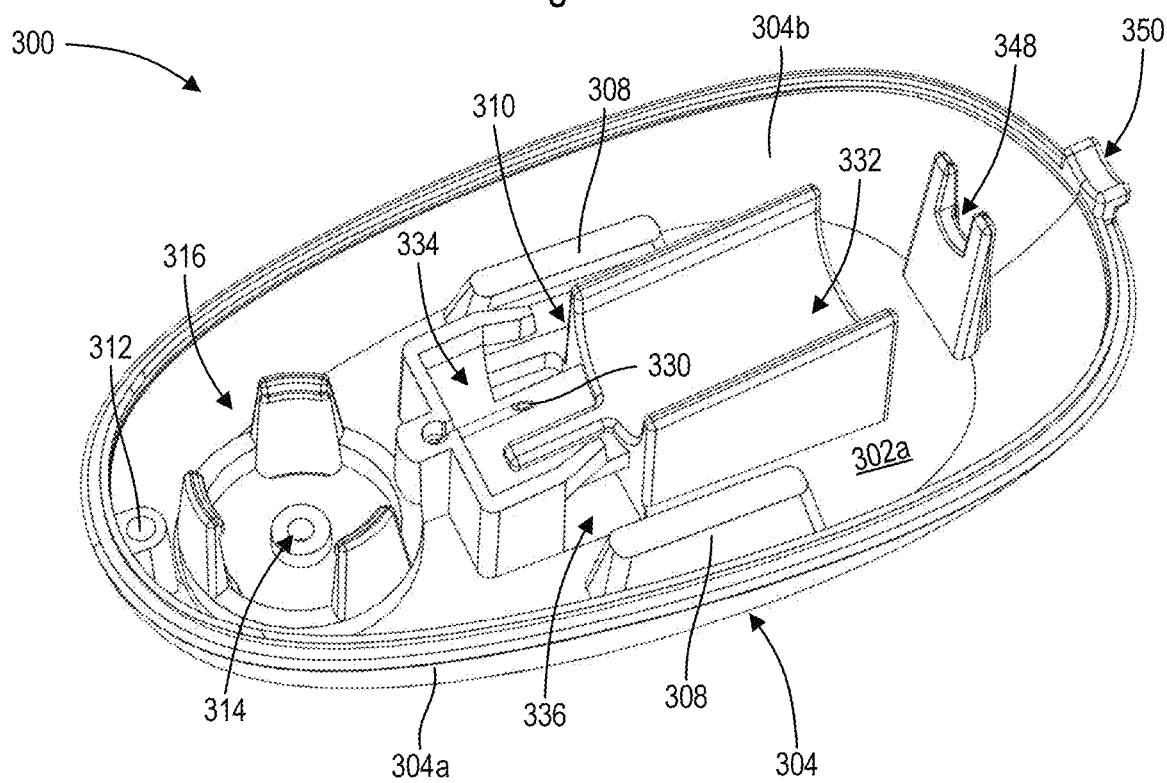
Figure 16A:
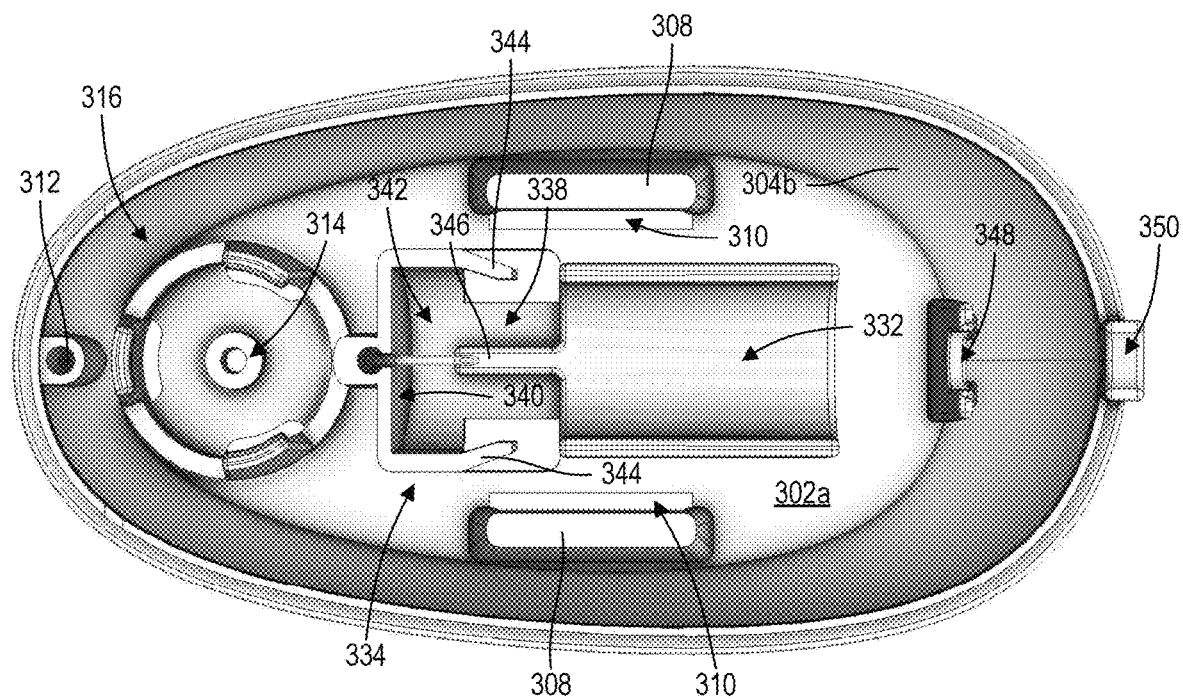
Figure 16B:
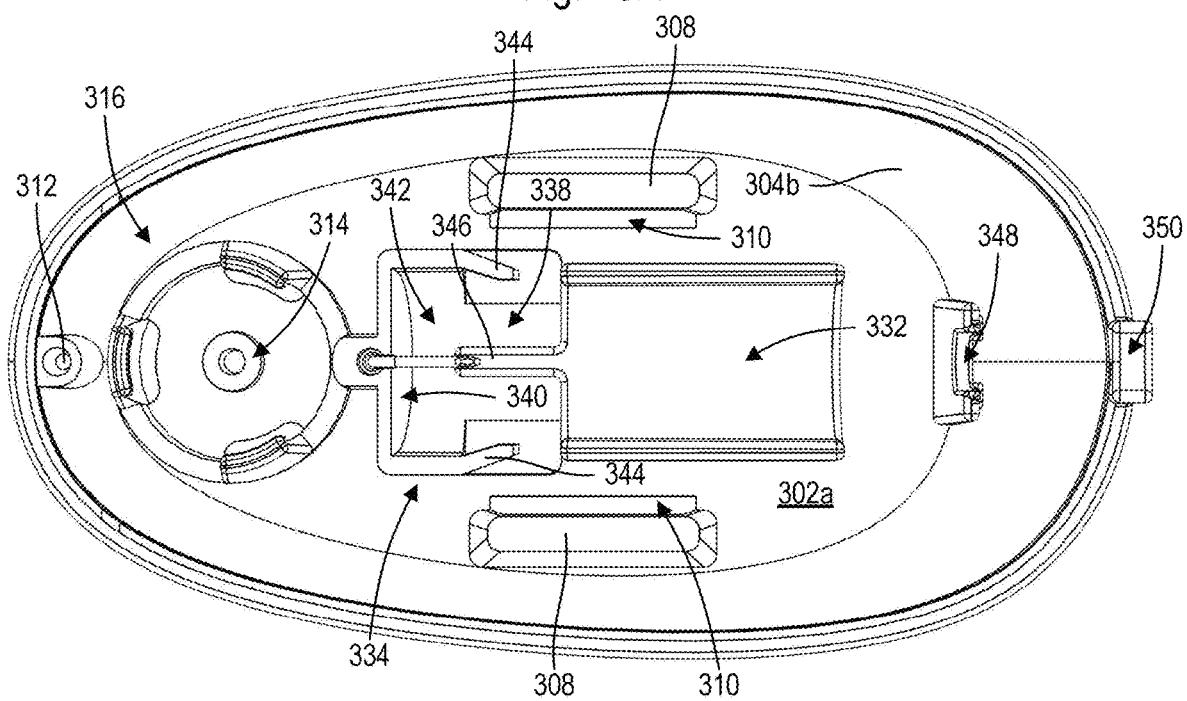
Figure 17B:
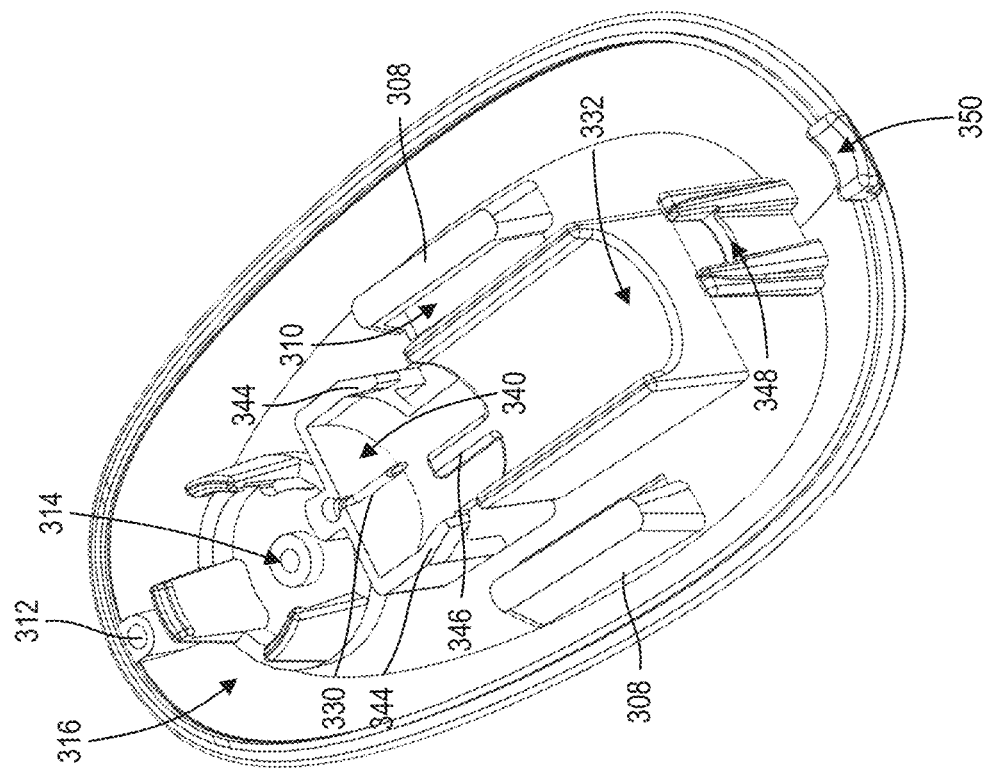
Figure 17A:
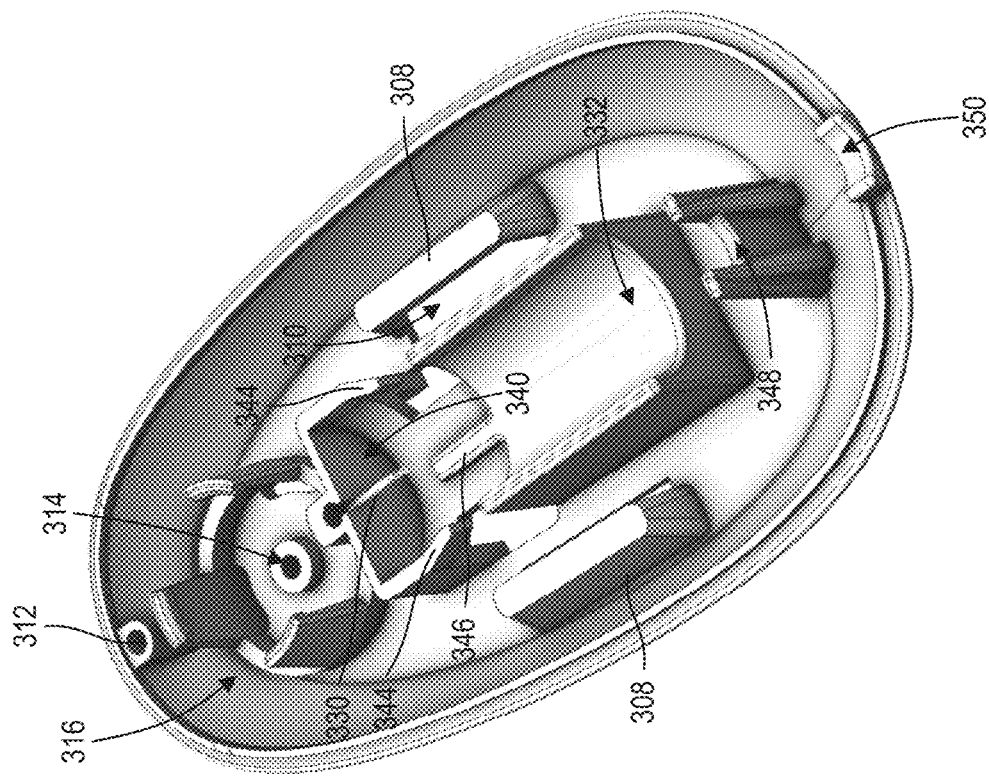
Figure 18A:
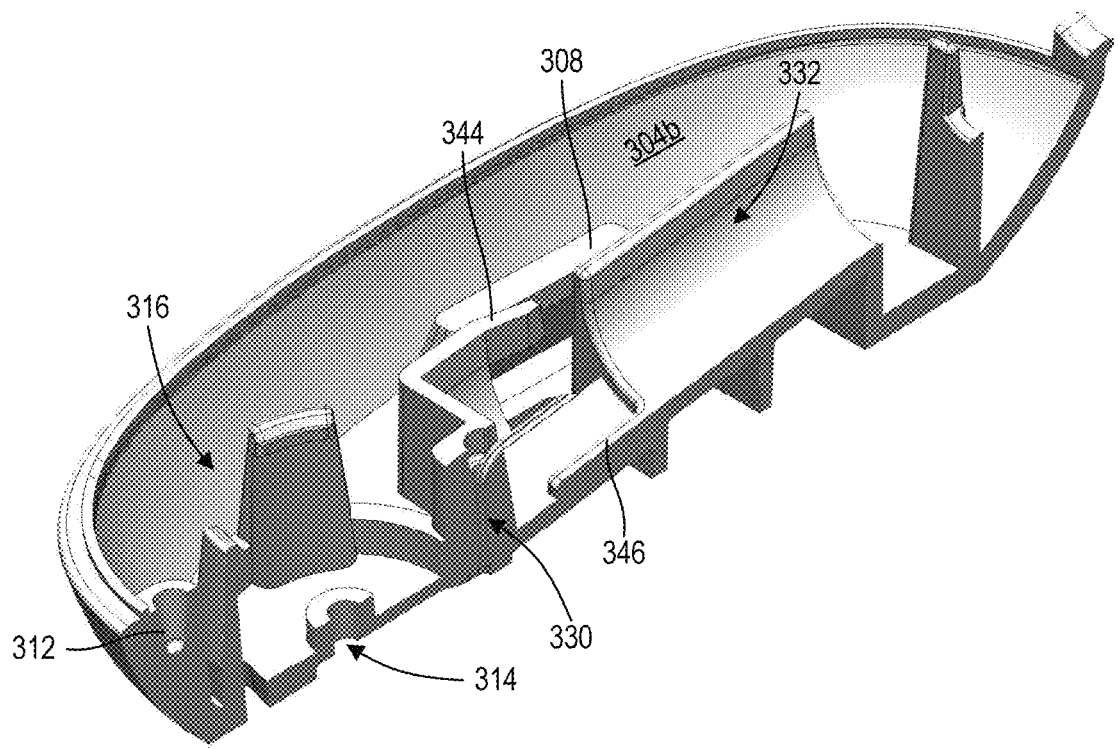
Figure 18B:
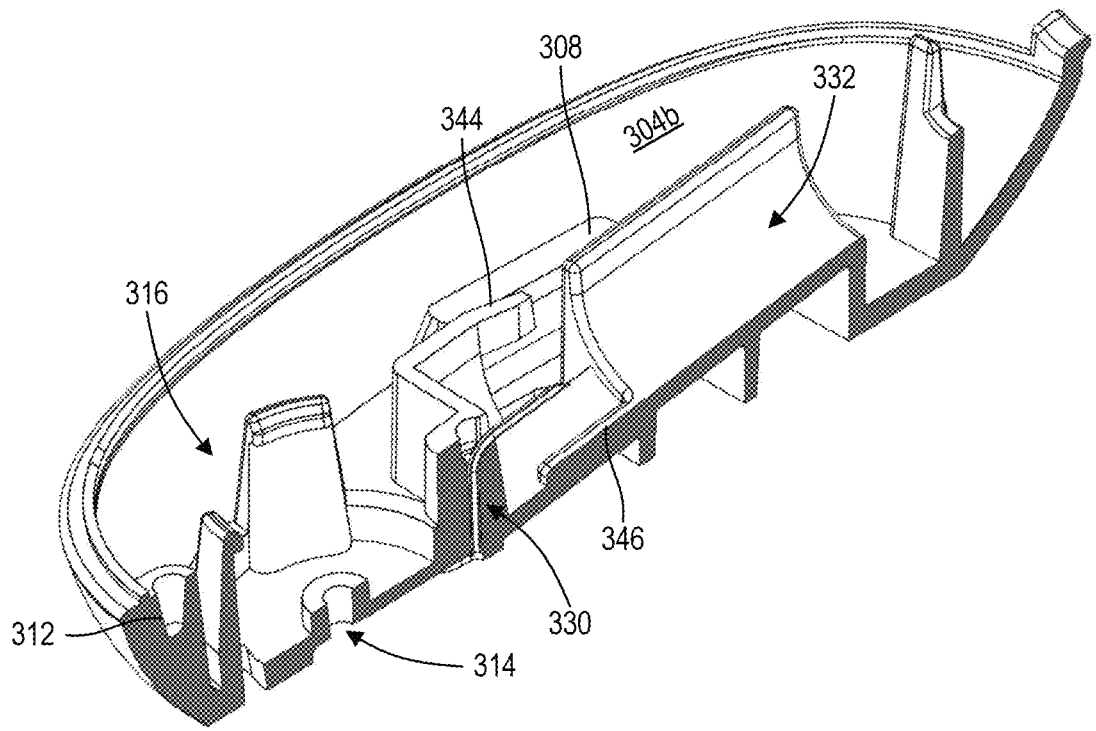
Figure 19A:
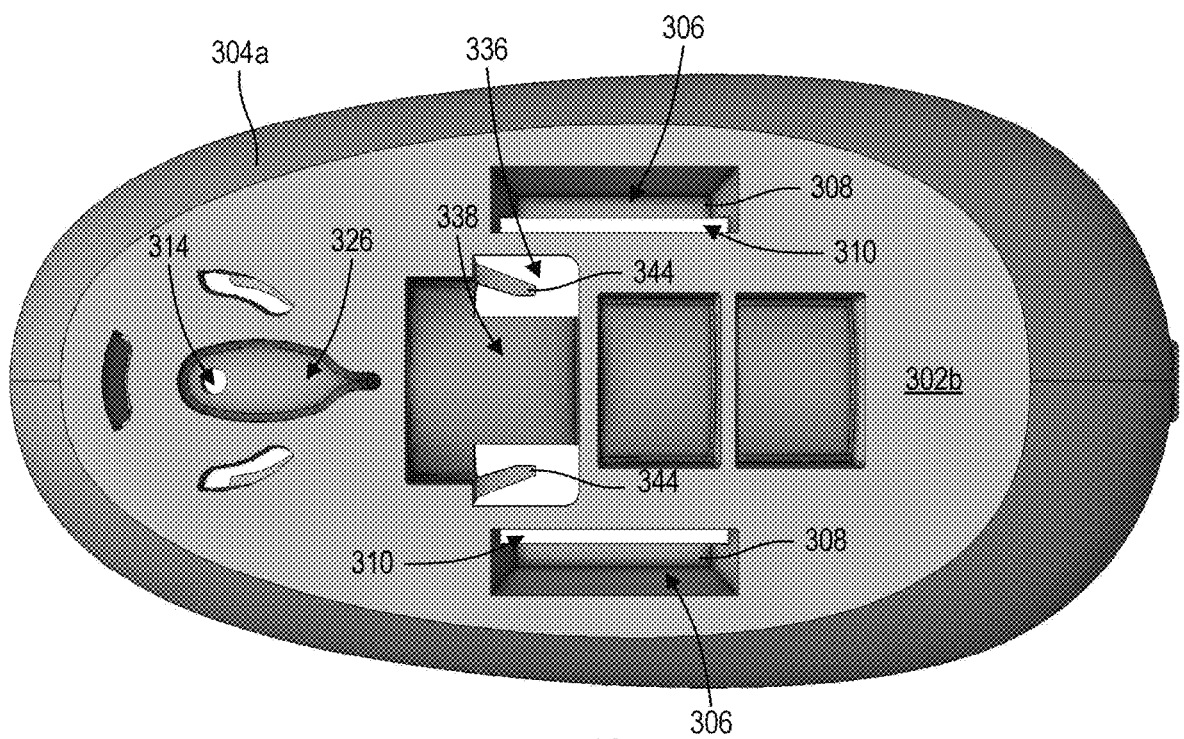
Figure 19B:
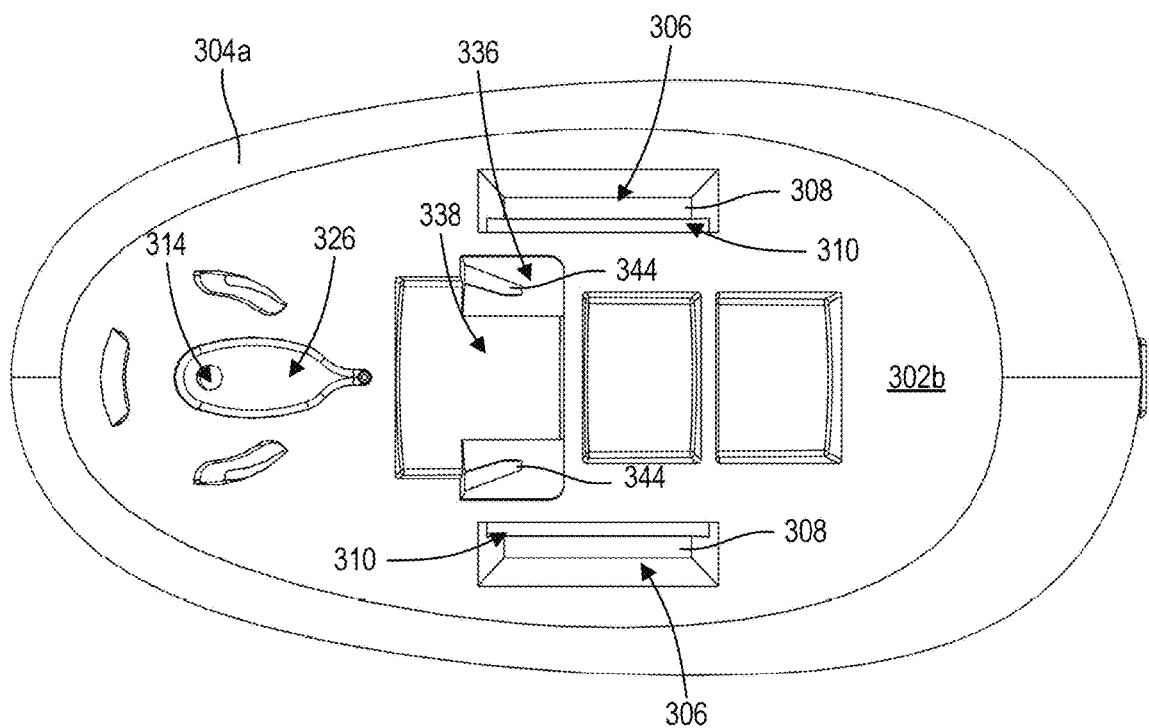

The lid 202 further defines a vial viewing aperture 208 and a quick response ("QR") code viewing aperture 210. The vial viewing aperture 208 and the QR code viewing aperture 210 extend through the lid 202. Stated another way, the vial viewing aperture 208 and the QR code viewing aperture 210 extend between the outer surface 202a and the inner surface 202b of the lid 202. The vial viewing aperture 208 is shaped and positioned to allow a user of the dermal patch system 10 to view the vial assembly 500 that is disposed within the cartridge 12. The QR code viewing aperture 210 is shaped and positioned to allow a user of the dermal patch system 10 to view a QR code 18 that is located on the vial assembly 500 (FIGS. 9A and 9B). While the QR code 18 is depicted as on the vial assembly 500, it is understood that the QR code 18 may be positioned elsewhere on the cartridge 12 (e.g., on the outer surface 202a of the lid 202). As will be discussed in further detail herein, the QR code 18 can be associated with an electronic medical record ("EMR") stored in an electronic medical record database.

The cover 200 further includes a rod 212 and locking members 214 that each includes a hook 216. The rod 212 and the locking members 214 extend vertically from and perpendicular to the inner surface 202b of the lid 202. As will be discussed in further detail herein, the rod 212 and the locking members 214 couple the cover 200 to the base 300.

The cover 200 also includes a locking wall 218 and a vial guide 220. The locking wall 218 and the vial guide 220 each extend vertically from and perpendicular to the inner surface 202b of the lid 202 and are disposed at opposite ends of the vial viewing aperture 208. Furthermore, the vial guide 220 extends longitudinally between the locking members 214. As will be discussed in further detail herein the locking wall 218 prevents movement of the vial assembly 500 when the vial assembly 500 is arranged in a first position and the vial guide 220 is shaped and dimensioned to guide movement of the vial assembly 500 when the vial assembly 500 is arranged in different position.

The cover 200 also includes a rotational stop 222 that extend vertically from and perpendicular to the inner surface 202b of the lid 202 and is disposed at a proximal end of the QR code viewing aperture 210b. The rotational stop 222 is positioned offset from a center of the cover 200 and, as will be discussed in further detail herein, the rotational stop 222 prevents the vial assembly 500 from rotating in a counter-clockwise direction.

The cover 200 further includes a stopping wall 224 that extends partially around the vial viewing aperture 208. The stopping wall 224 extends around the distal end of the vial viewing aperture 208. As will be discussed in further detail herein, the stopping wall 224 prevents horizontal movement of the vial assembly 500.

With reference to FIGS. 15A and 15B-20A and 20B, the base 300 is shown in accordance with an exemplary embodiment. In this embodiment, the base 300 includes a bottom wall 302 with a top surface 302a and an opposed bottom surface 302b. The base 300 also includes a side wall 304 with an outer surface 304a and an opposed inner surface 304b. The side wall 304 extends vertically from the bottom wall 302 and the bottom wall 302 extends longitudinally from the side wall 304. The side wall 304 has a similar shape and dimension as the lid 202 such that the lid 202 and the side wall 304 are flush with one another when the cover 200 is coupled to the base 300.

Figure 22A:
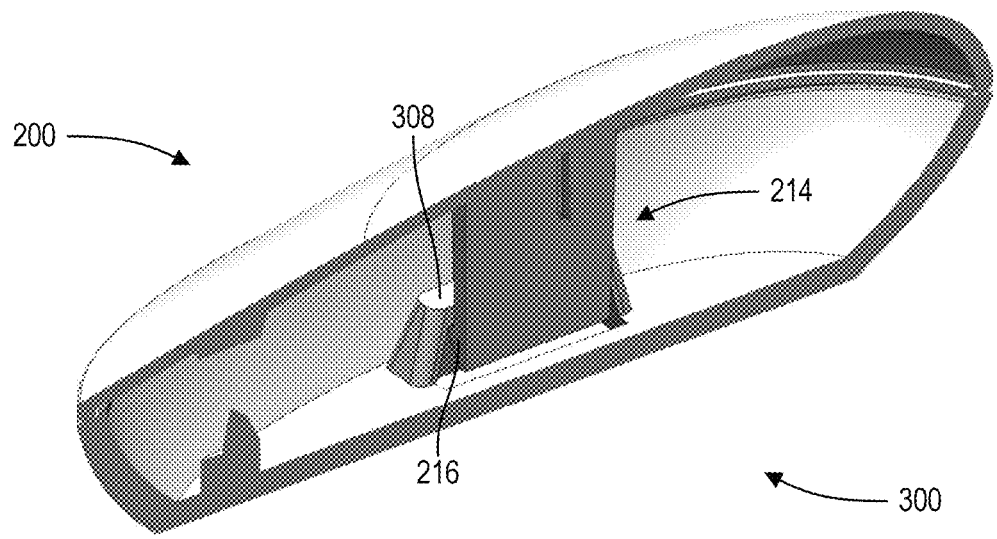
FIGS. 22A and 22B depict the cover coupled to the base in accordance with an exemplary embodiment of the present disclosure.
Figure 22B:
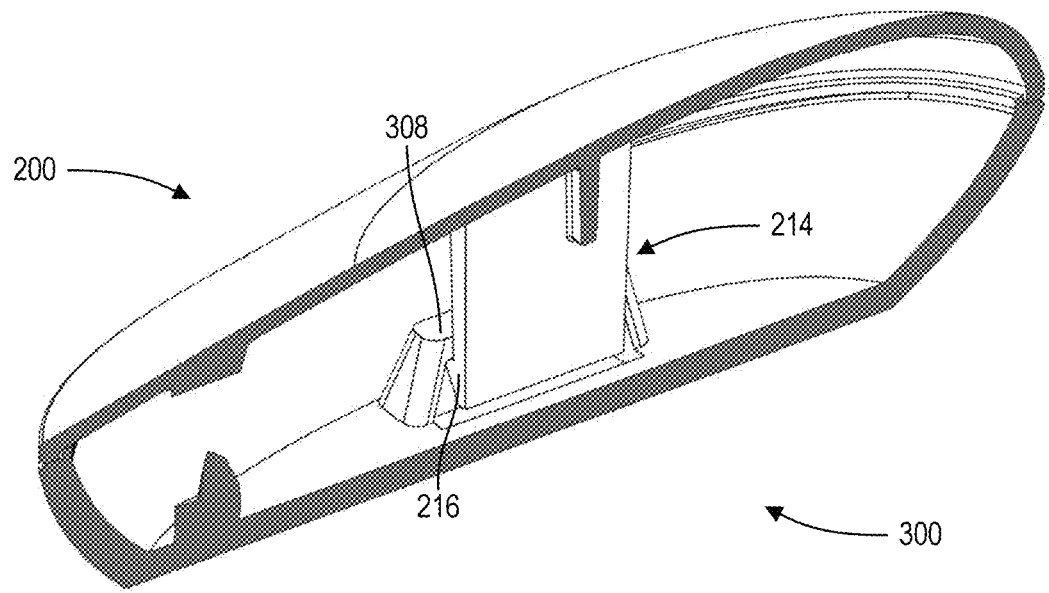

The bottom wall 302 defines openings 306 that extend through the bottom wall 302. The base 300 also includes extensions 308 that extend vertically from and perpendicular to the top surface 302a of the bottom wall 302. The extensions 308 define gaps 310. The extensions 308 are located above the openings 306 such that a gap 310 is aligned with an opening 306. The gaps 310 and therefore the extensions 308 are shaped to accept a hook 216 of a locking member 214 such that an extension 308 couples to a hook 216 via a snap fitting thereby coupling the base 300 to the cover 200 (FIG. 22A and 22B). The base 300 also includes a rod receptacle 312. The rod receptacle 312 is shaped and dimensioned to accept the rod 212 such when the cover 200 is coupled to the base 300.

The base 300 further includes a needle aperture 314 that is generally circular in shape. The needle aperture 314 extends through the bottom wall 302. Stated another way, the needle aperture 314 extends between the top surface 302a and the bottom surface 302b of the bottom wall 302. As will be discussed in further detail herein, when the cover 200 is coupled to the base 300 and when the cartridge 12 is adhered to the skin of a subject, the needle aperture 314 allows the needle 110 of the lancet 100 to extend through the bottom wall 302 to pierce the skin of the subject, skin, thereby allowing extraction of a physiological sample.

Figure 23:
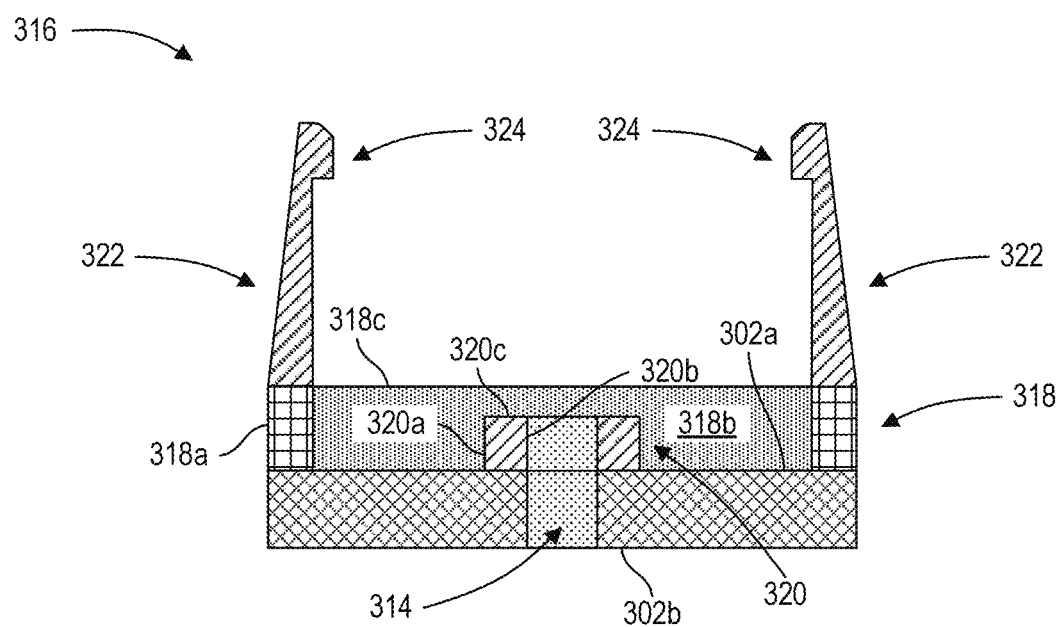
FIG. 23 diagrammatically depicts a lancet receiving element of the base in accordance with an exemplary embodiment of the present disclosure.
Figure 24B:
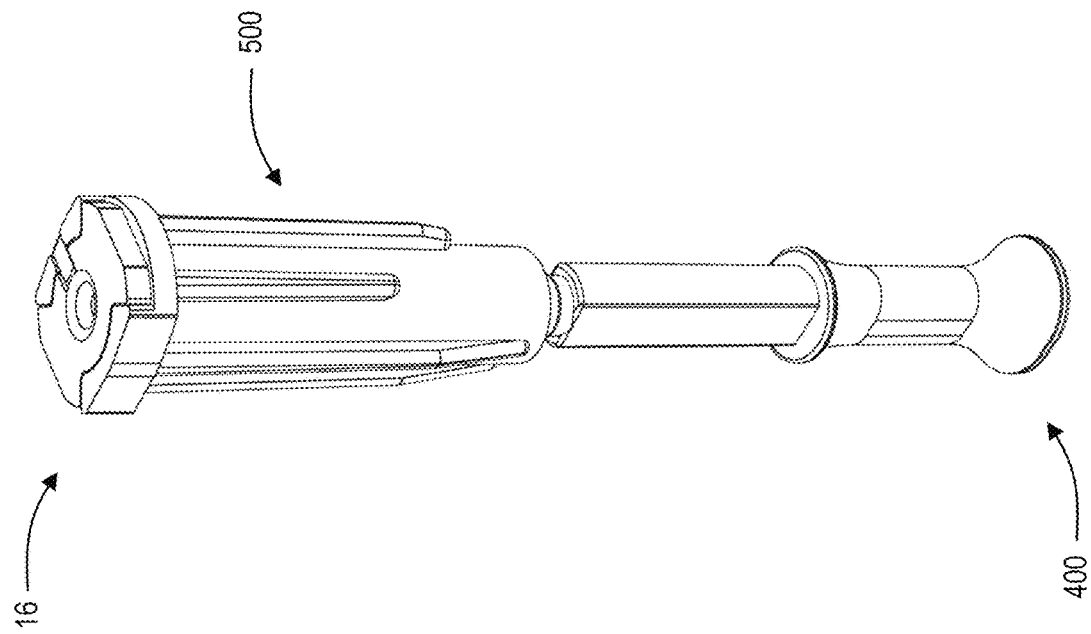
Figure 24A:
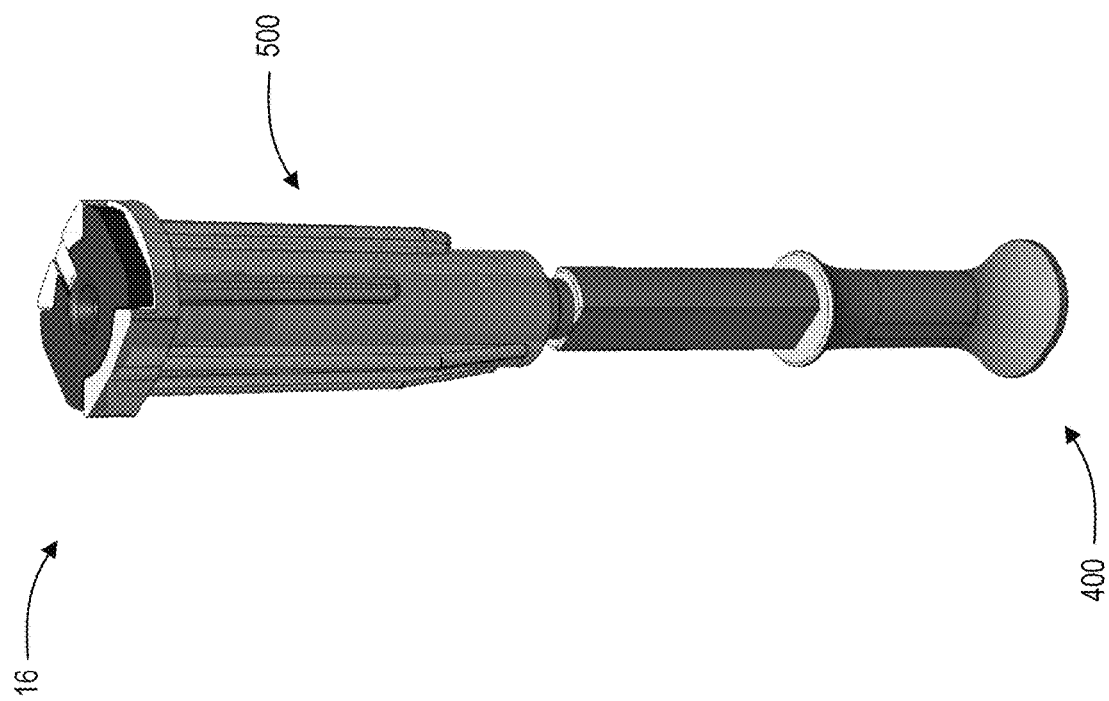
Figure 26:
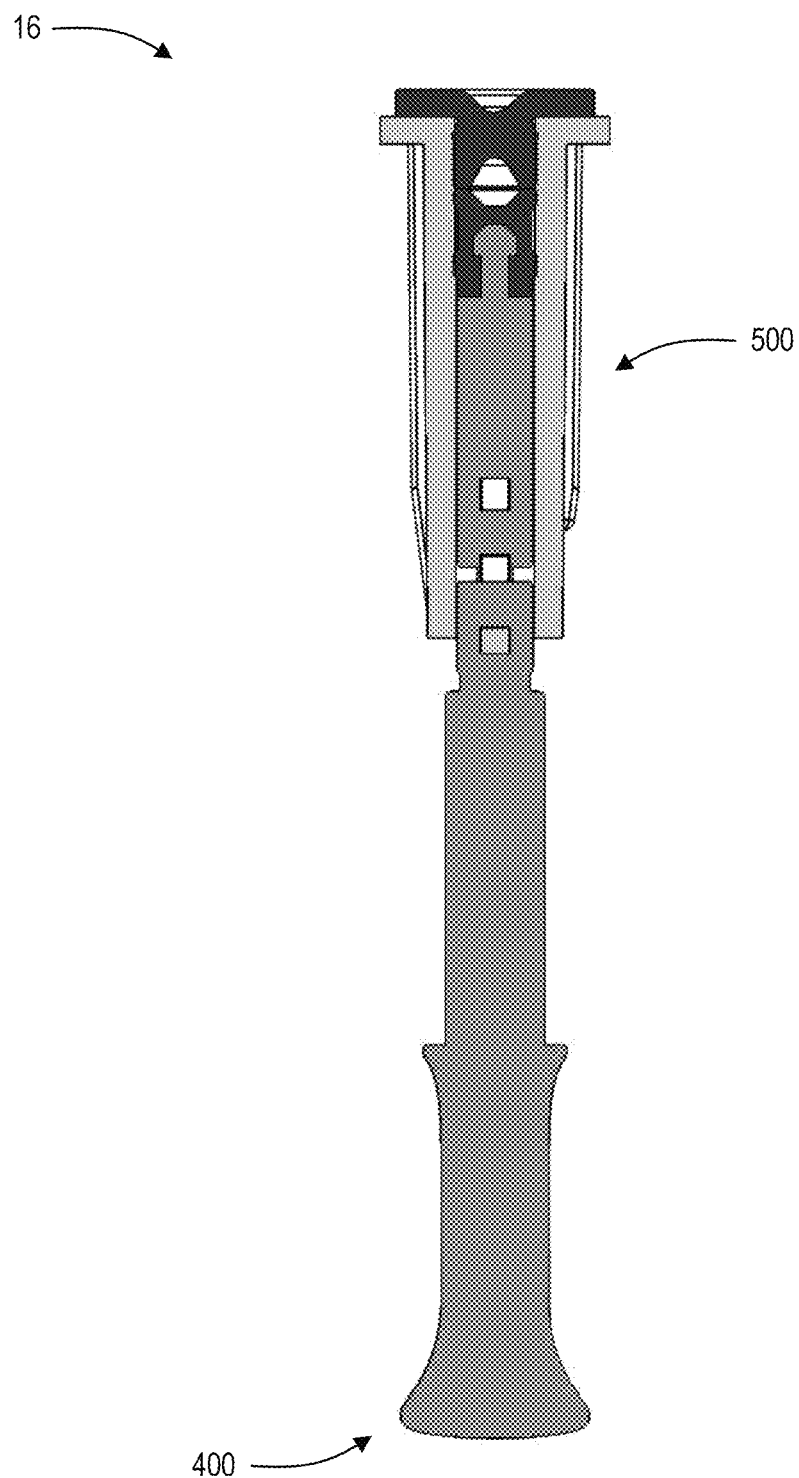
Figure 27:
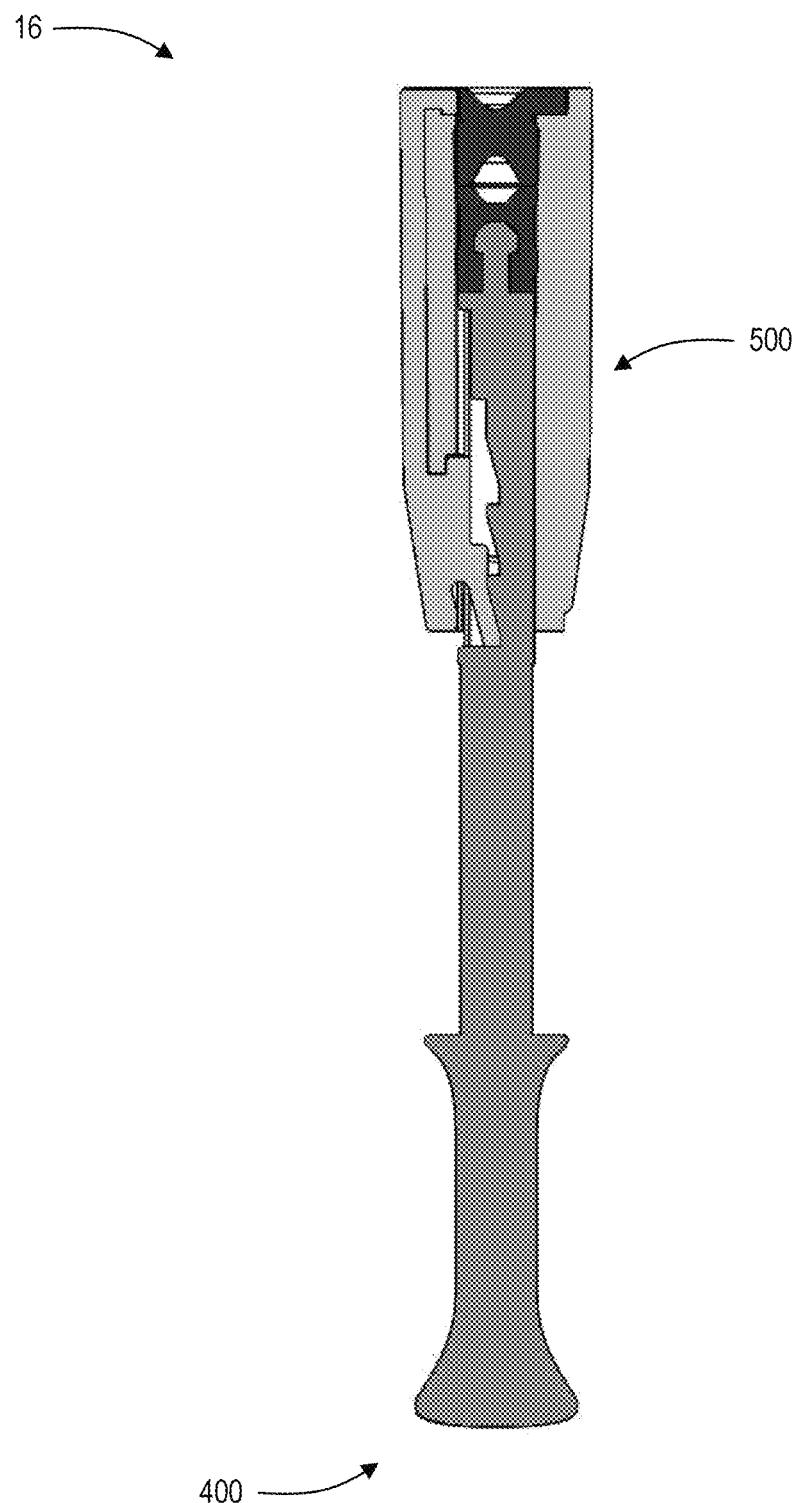
Figure 28B:
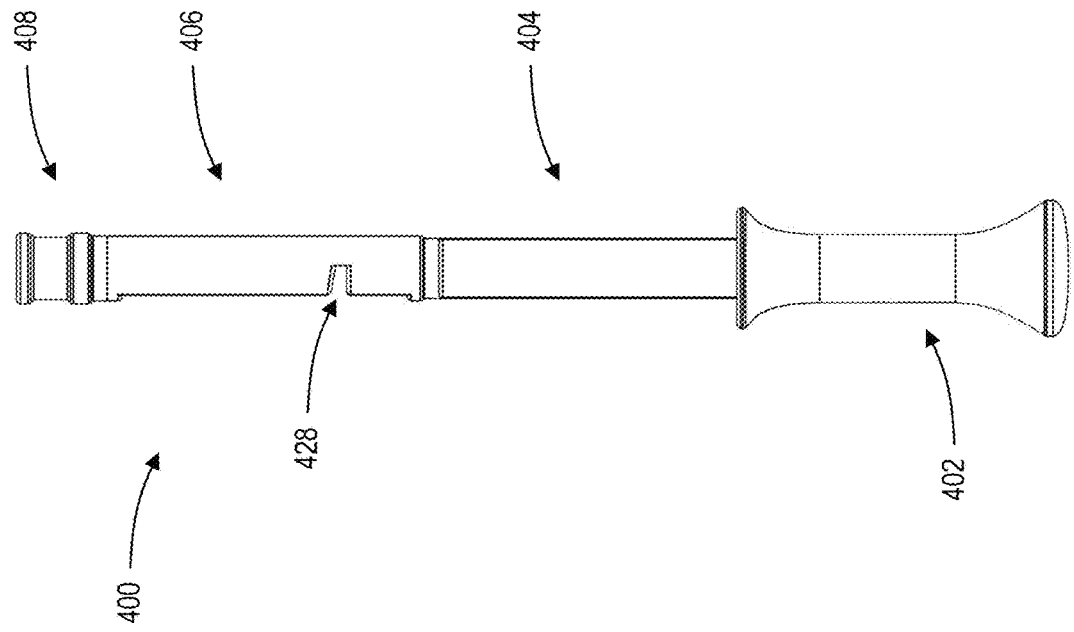
FIGS. 28A and 28B depict a plunger of the syringe with an elastomeric ring in accordance with an exemplary embodiment of the present disclosure.
Figure 28A:
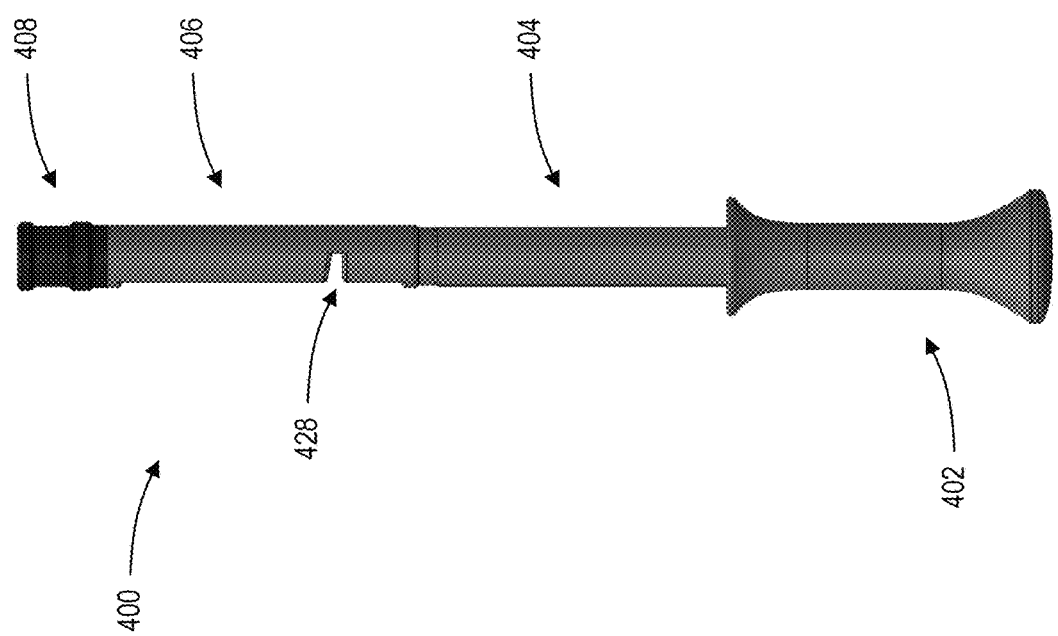
Figure 30A:
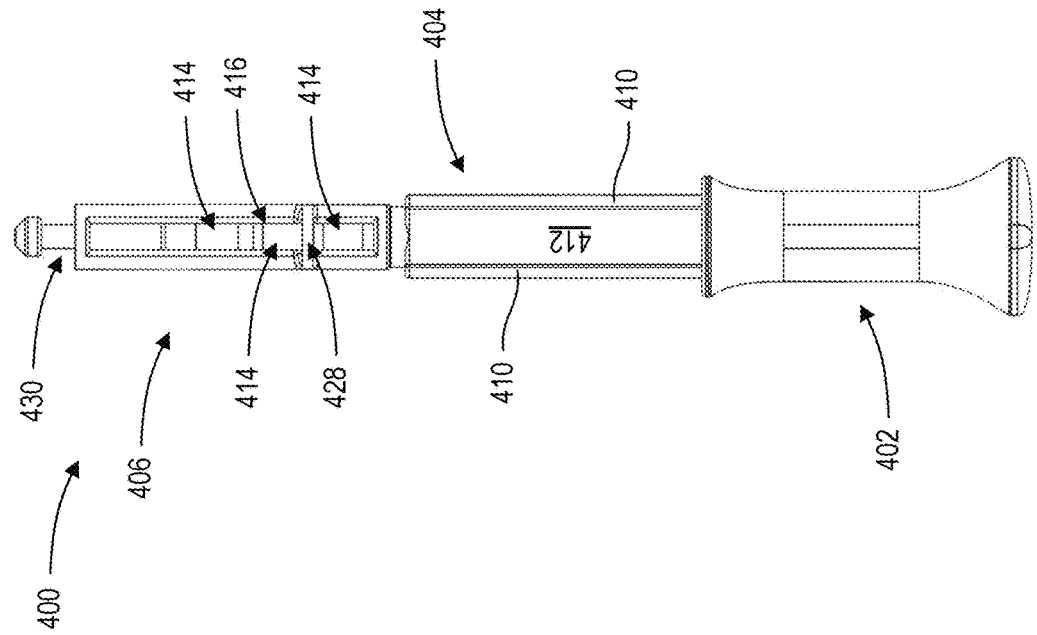
Figure 30B:
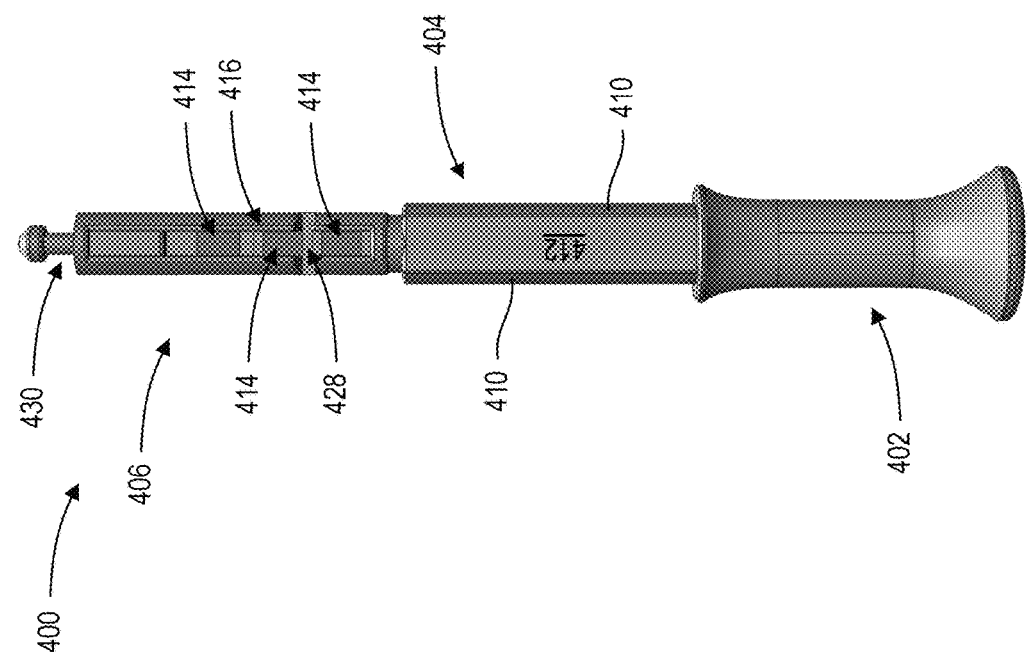

The base 300 also includes a lancet receiving element 316 that is shaped and dimensioned to accept the proximal end of the lancet 100. With particular reference to FIG. 23, the lancet receiving element 316 includes an outer circular projection 318 and an inner circular projection 320 with each extending vertically from and perpendicular to the top surface 302a of the bottom wall 302. The outer circular projection 318 includes an outer surface 318a, an opposed inner surface 318b, and a top surface 318c that extends between the outer surface 318a and the inner surface 318b. The top surface 318c extends perpendicular to and longitudinally between the outer surface 318a and the inner surface 318b. The outer surface 318a and the inner surface 318b extend vertically from and perpendicular to the top surface 302a of the bottom wall 302 such that the outer surface 318a and the inner surface 318b extend between the top surface 302a and the top surface 318c. The outer circular projection 318 is shaped to accept the lancet 100.

The inner circular projection 320 is disposed around the needle aperture 314 and includes an outer surface 320a, an opposed inner surface 320b, and a top surface 320c that extends between the outer surface 320a and the inner surface 320b. The top surface 320c extends perpendicular to and longitudinally between the outer surface 320a and the inner surface 320b. The outer surface 320a and the inner surface 320b extend vertically from and perpendicular to the top surface 302a of the bottom wall 302 such that the outer surface 320a and the inner surface 320b extend between the top surface 302a and the top surface 320c.

Furthermore, the outer circular projection 318 and the inner circular projection 320 are concentric with one another. As will be discussed in further detail herein, when the lancet 100 is engaged with the base 300, the top surface 320c of the inner circular projection 320 contacts the outer surface 138a of the bottom wall 138 of the inner sleeve 106 which allows the lancet 100 to release the needle 110 so as to puncture the skin, thereby allowing the extraction of a physiological sample from the subject's skin.

The base 300 further includes a plurality of locking members 322 that extend vertically from and perpendicular to the top surface 318c of the outer circular projection 318. Each locking member 322 includes a hook 324 that extends inwardly from a top of a locking member 322 towards the inner circular projection 320. As will be discussed in further detail herein, the hooks 324 of the locking members 322 couple to the lancet 100 to retain the lancet 100 within the base 300.

Figure 20A:
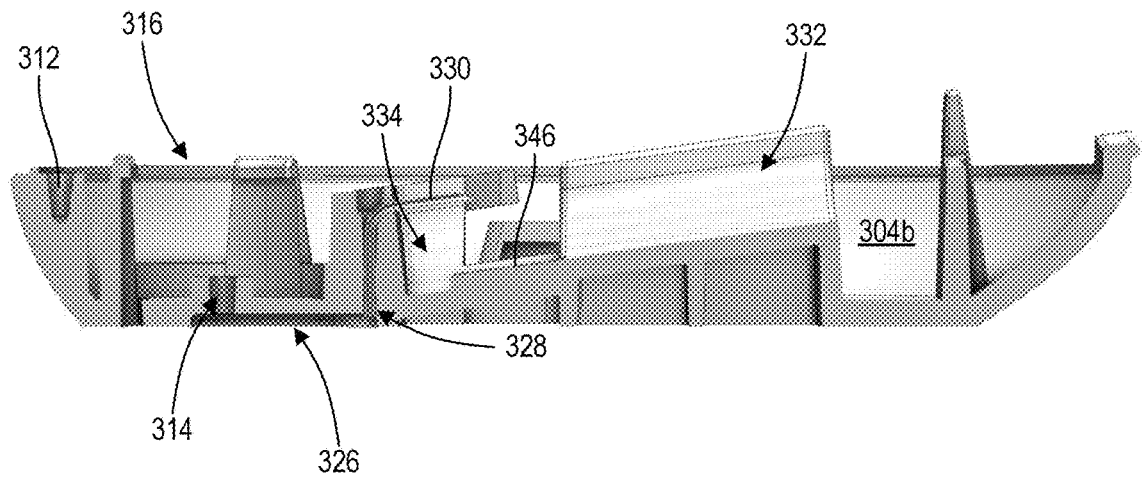
Figure 20B:
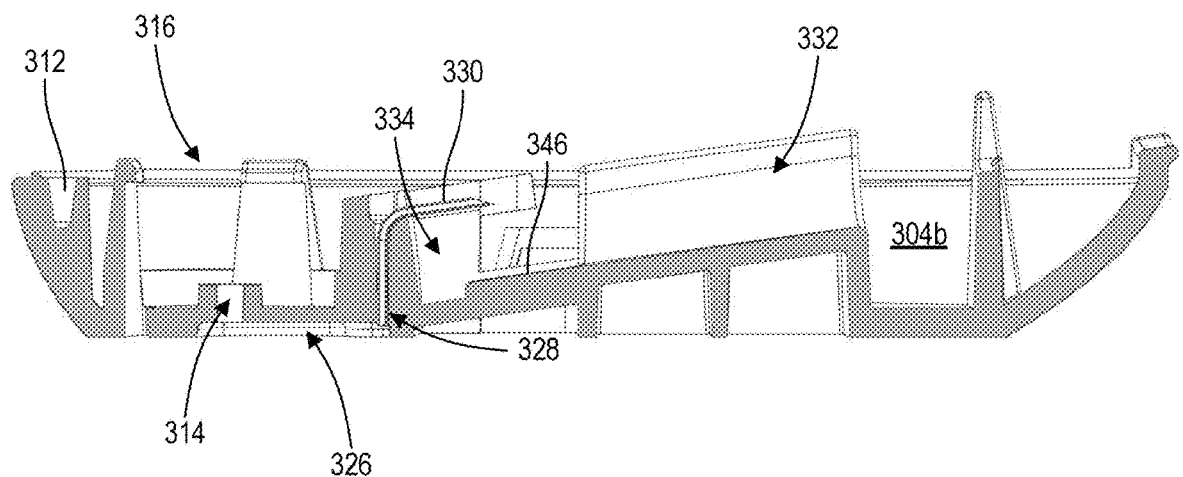

With particular reference to FIGS. 20A and 20B, the base 300 includes a physiological sample well 326 and a channel 328 that that is in open communication with and extends from the physiological sample well 326. As will be discussed in further detail herein, when a physiological sample is drawn from a subject, the physiological sample pools within the physiological sample well 326. The channel 328 is shaped and dimensioned to retain a bent hollow needle 330. Furthermore, the channel 328 includes an opening opposite the physiological sample well 326 which allows the needle 330 into the channel 328. As will be discussed in further detail herein the needle 330 is configured to carry a drawn physiological sample from the physiological sample well 326 to the vial assembly 500.

The base 300 further includes a first vial holder 332 and a second vial holder 334, where each of which extends vertically from and perpendicular to the top surface 302a of the bottom wall 302. The first vial holder 332 and the second vial holder 334 are separated from one another by a gap 336. An extension member 338 extends crosses the gap 336 and extends between the first vial holder 332 and the second vial holder 334. The first vial holder 332, the second vial holder 334, and the extension member 338 are shaped and dimensioned to accept and retain the vial assembly 500.

The second vial holder 334 includes an end wall 340 through which the channel 328 extends. The second vial holder 334 also includes a semi-circular wall 342 that has a similar shape and dimension as the vial assembly 500. The end wall 340 extends vertically from and perpendicular to the top surface 302a of the bottom wall 302. The semi-circular wall 342 extends longitudinally from and perpendicular to the end wall 340. Furthermore, the connection member 338 extends between the first vial holder 332 and the semi-circular wall 342.

The second vial holder 334 also includes latches 344 that extend longitudinally from the semi-circular wall 342. The latches 344 are angled inwardly towards a middle of the base 300. As will be discussed in further detail herein, the latches 344 allow the vial assembly 500 to move from one position wherein the needle 330 extends into the vial assembly 500 to another wherein the needle 330 is removed from the vial assembly 500. Furthermore, as will be discussed in further detail herein, the latches 344 prevent a user from transitioning the vial assembly 500 back to its original position.

Figure 21A:
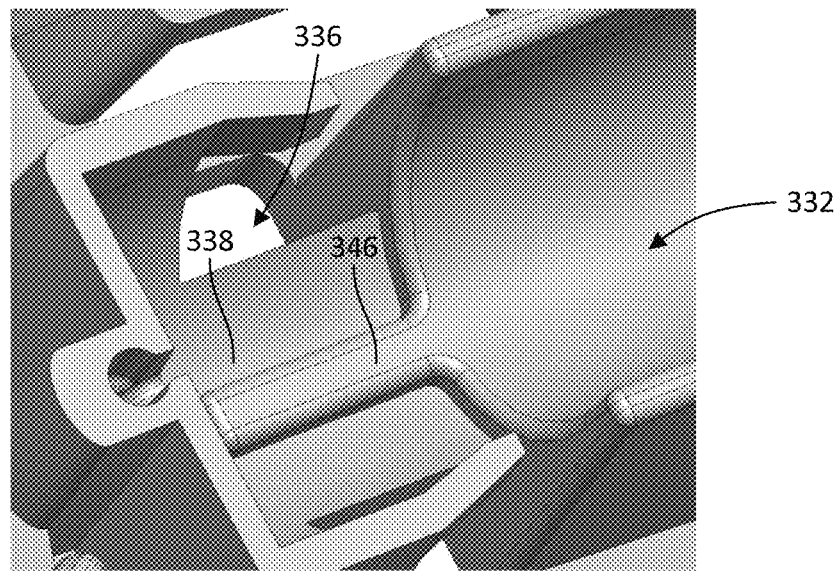
FIG. 21A and 21B depict a portion of the base of the cartridge in accordance with an exemplary embodiment of the present disclosure.
Figure 21B:
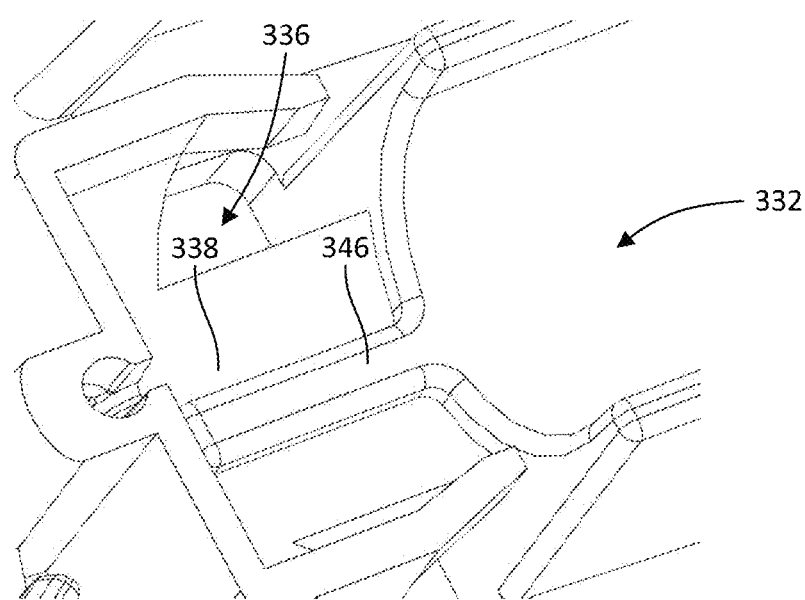

The extension member 338 further includes a protrusion 346 that extends vertically from the extension member 338. As will be discussed in further detail herein, when the vial assembly 500 is in the first position, a portion of the vial contacts the protrusion 346 which prevents the vial assembly 500 from transitioning to a different position until the vial assembly 500 is rotated. As depicted in FIGS. 21A and 21B, the first vial holder 332 extends vertically above the extension member 338 such that the first vial holder has a proximal end surface from which the protrusion 346 extends.

The base 300 also includes U-shaped locking feature 348 and a plunger support 350. The U-shaped locking feature 348 extends vertically from and perpendicular to the top surface 302a of the bottom wall 302. The U-shaped locking feature 348 is shaped and dimensioned to support and guide the plunger 400. As will be discussed in further detail herein, the U-shaped locking feature 348 prevents rotation of the plunger 400 until a physiological sample is drawn into the vial assembly 500. The plunger support 350 extends vertically from and perpendicular to the side wall 304. When the cover 200 is coupled to the base 300 the plunger support 350 is aligned with the U-shaped opening 204. The plunger support 350 is shaped and dimensioned to support the plunger 400 when the plunger 400 is disposed within the cartridge 12.

The rounded surface of the first vial holder 332, the rounded surface of the extension member 338, and the surface of the semi-circular wall 342 angle downward at an angle of about 85° away from the plunger support 350 and towards the end wall 340 such that the vial assembly 500 has an angled orientation when disposed within the cartridge 12. Furthermore, the plunger support 350 and the U-shaped locking feature 348 are oriented such that the plunger 400 has an angled orientation when disposed within the cartridge 12.

With respect to FIGS. 24A and 24B-27, the syringe 16 is shown in accordance with an exemplary embodiment. As previously discussed herein, the syringe 16 includes the plunger 400 and the vial assembly 500.

As depicted in FIGS. 27A and 27B-32, the plunger 400 includes a handle 402, a shaft 404, a rod 406, and an elastomeric ring 408. The handle 402 defines a proximal end of the plunger 400, the shaft 404 extends between the handle 402 and the rod 406, and the rod 406 extends from the shaft 404 and defines a proximal end of the plunger 400. Furthermore, the elastomeric ring 408 surrounds the proximal end of the rod 406.

The shaft 404 is generally cylindrical in shape and includes opposing rounded surfaces 410 and opposing flat surfaces 412 that are disposed between the opposing rounded surfaces 410. As will be discussed in further detail herein, the profile of the shaft 404 prevents the plunger 400 from rotating until the plunger 400 is moved from a first position to a second position.

The rod 406 is generally cylindrical in shape and has a smaller diameter than the shaft 404. As will be discussed in further detail herein, this smaller diameter allows the rod 406 to rotate when the syringe 16 is disposed within the cartridge 12. The rod 406 includes a plurality of projection members 414 that are disposed within a groove 416 of the rod 406. Each projection member 414 includes an angled top surface 418 and a first projection member and a second projection members each include a side surface 420 that extends vertically from a top surface 418. The rod 406 further includes a stopping wall 422 that is also disposed within the groove 416. The stopping wall 422 includes a top surface 424 and a side surface 426 that extends vertically from and perpendicular to the top surface 424.

The rod 406 also includes a snap-off joint 428. As will be discussed in further detail herein, the snap-off joint 428 serves as a break point of the plunger 400 (FIG. 31) which allows the handle 402 and the shaft 404 to sperate from a remainder of the plunger 400. The plunger 400 also includes a projection 430 that extends longitudinally from the proximal end of the rod 406. The projection 430 is shaped and dimensioned to be inserted into the elastomeric ring 408.

Figure 34:
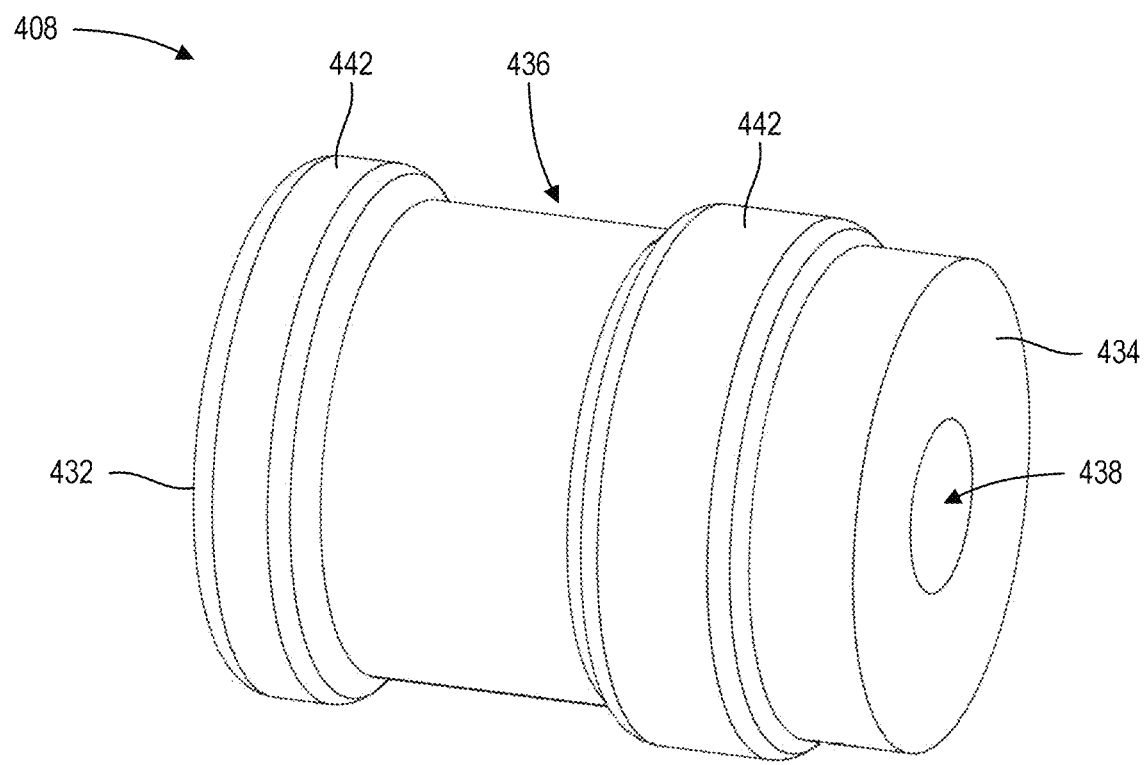
FIGS. 34 and 35 depict the elastomeric ring for use with the plunger in accordance with an exemplary embodiment of the present disclosure.
Figure 35:
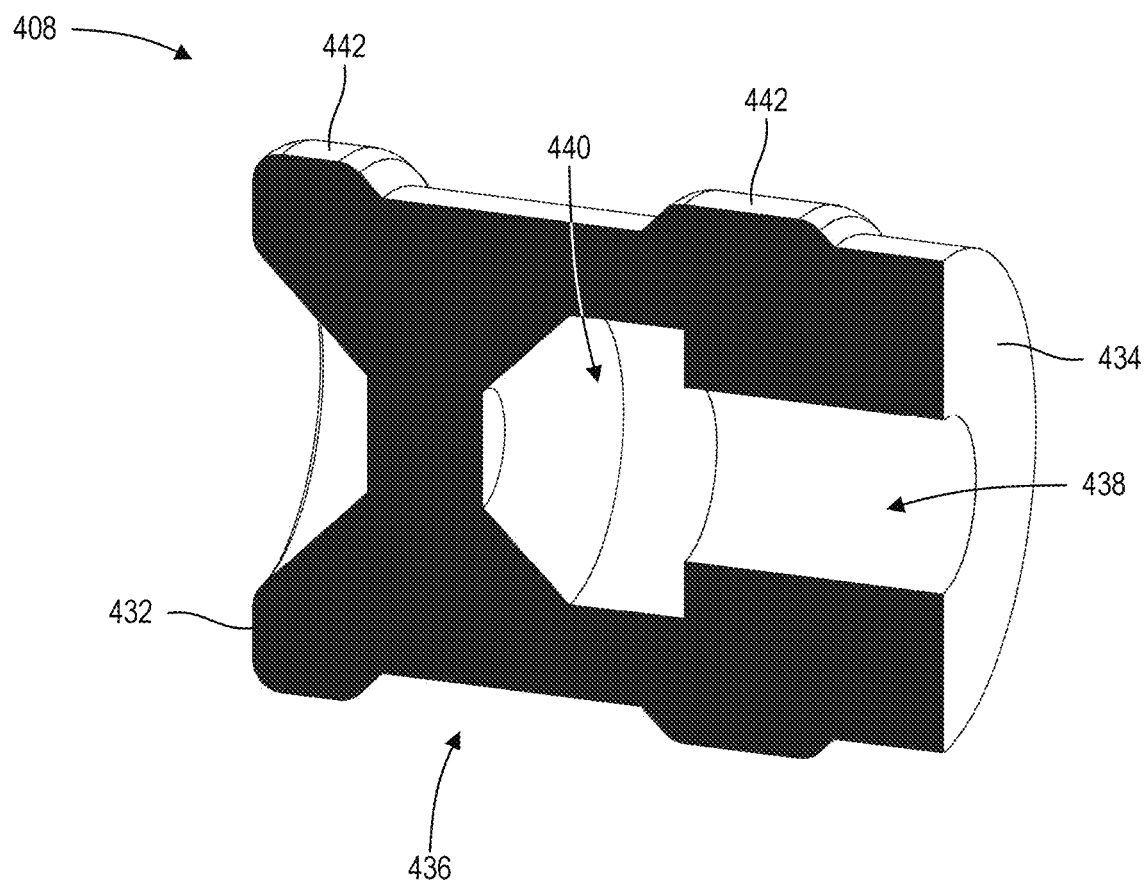
Figure 36B:
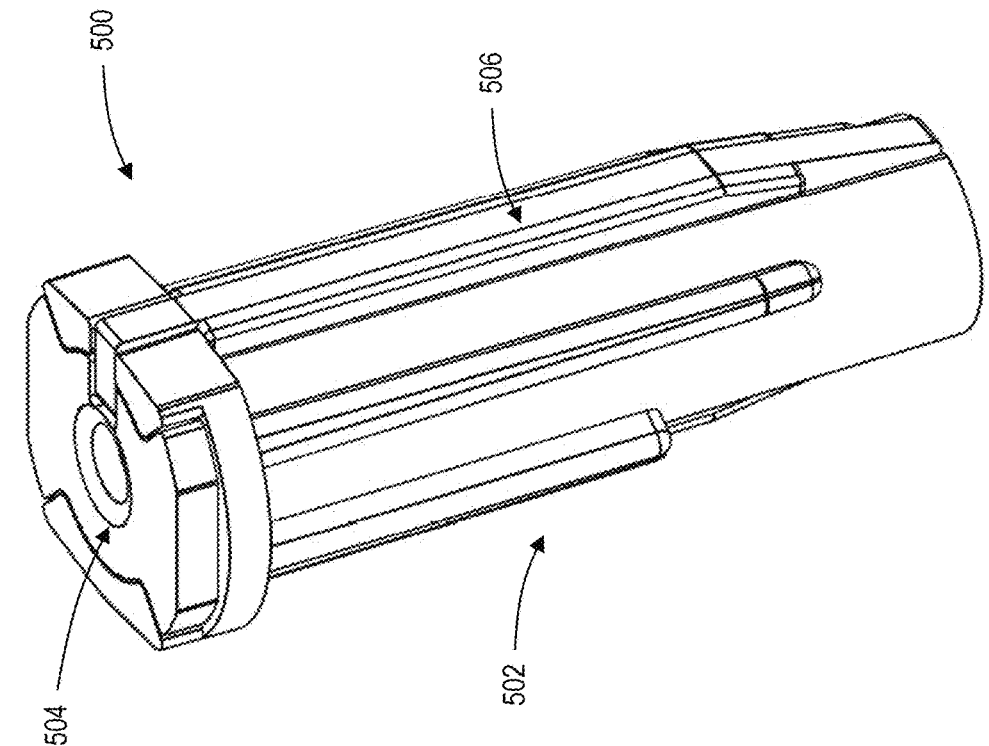
Figure 36A:
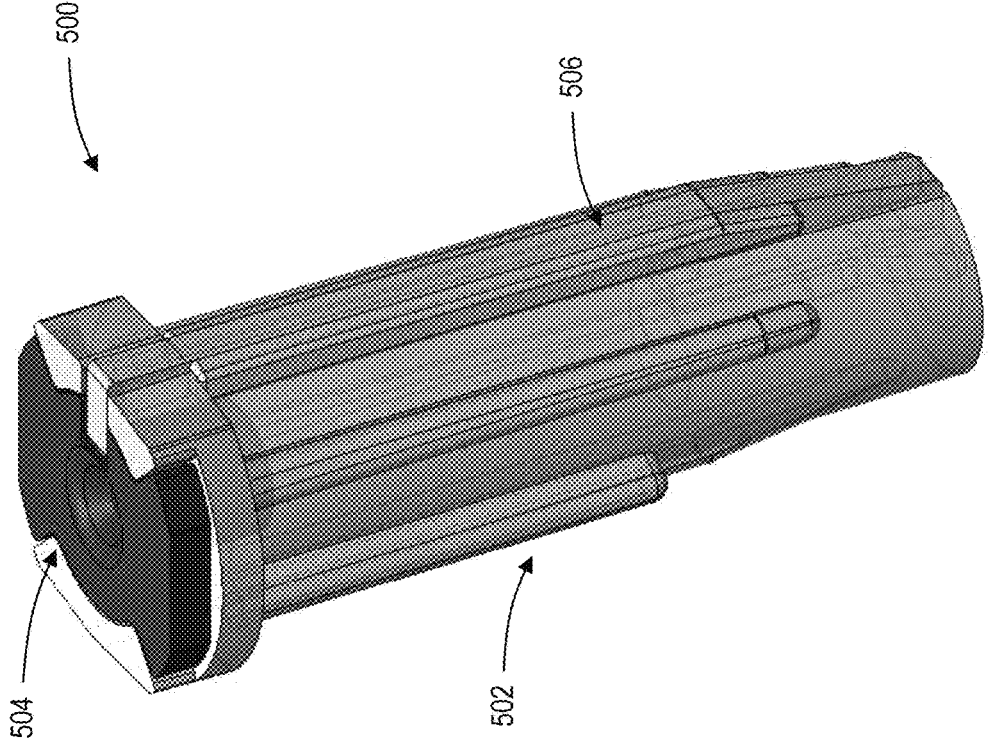
Figure 37B:
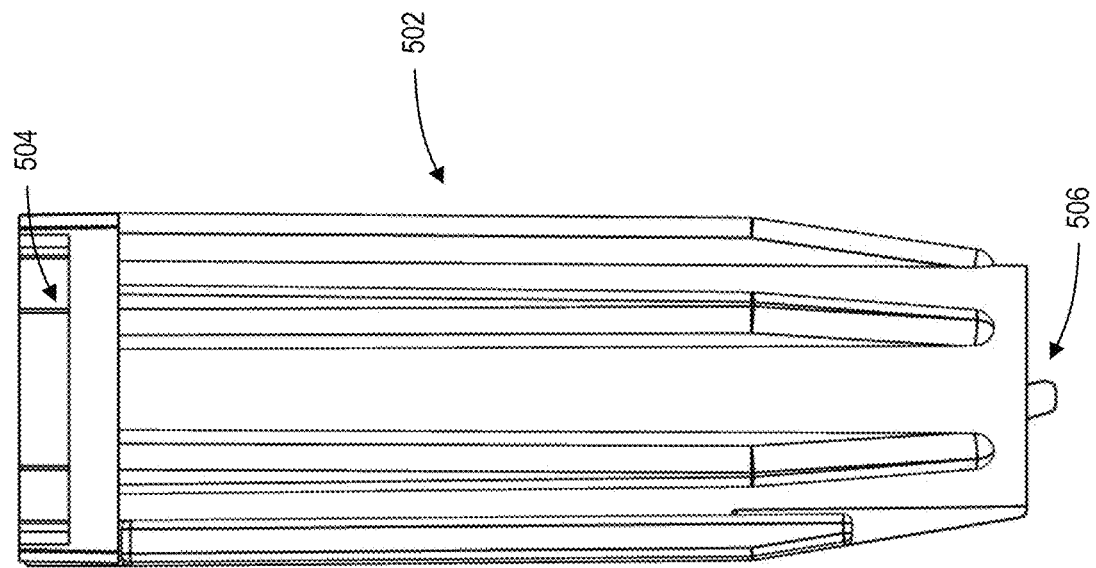
Figure 37A:
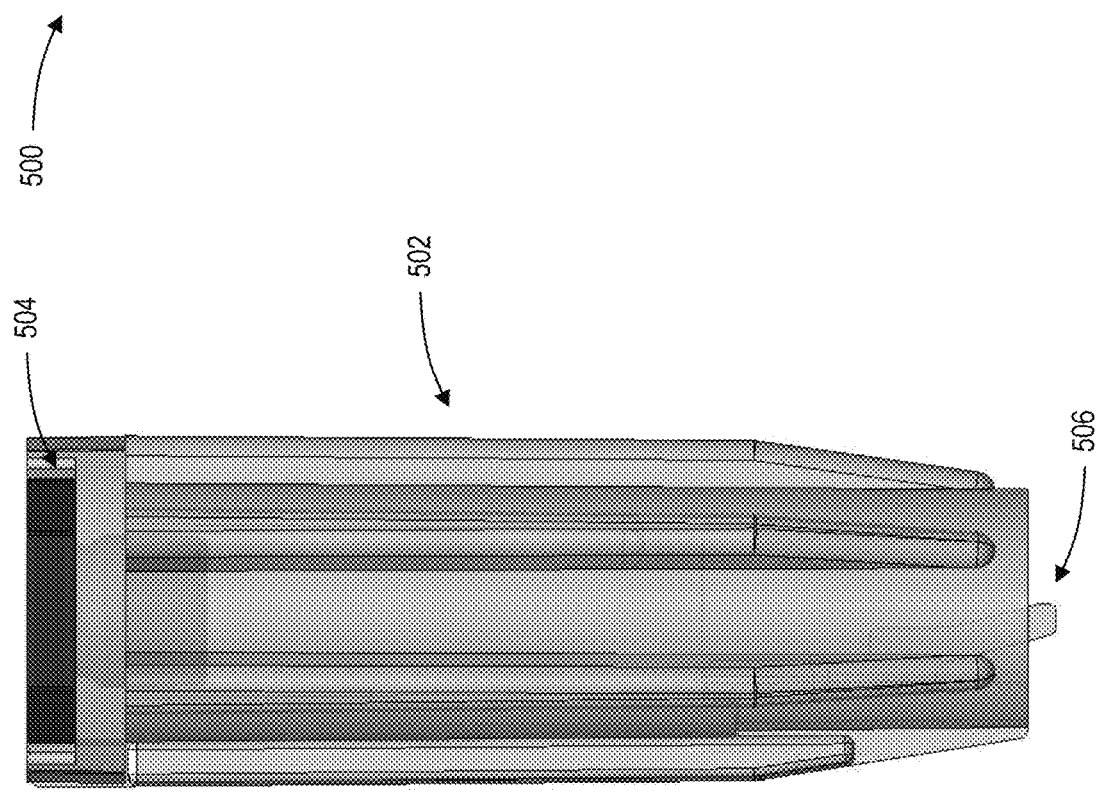
Figure 39B:
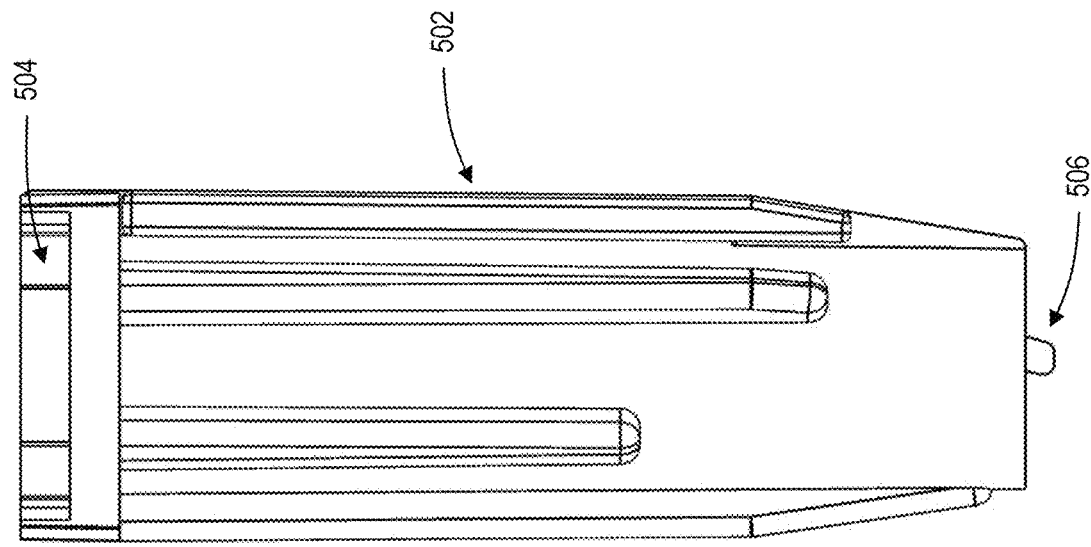
Figure 39A:
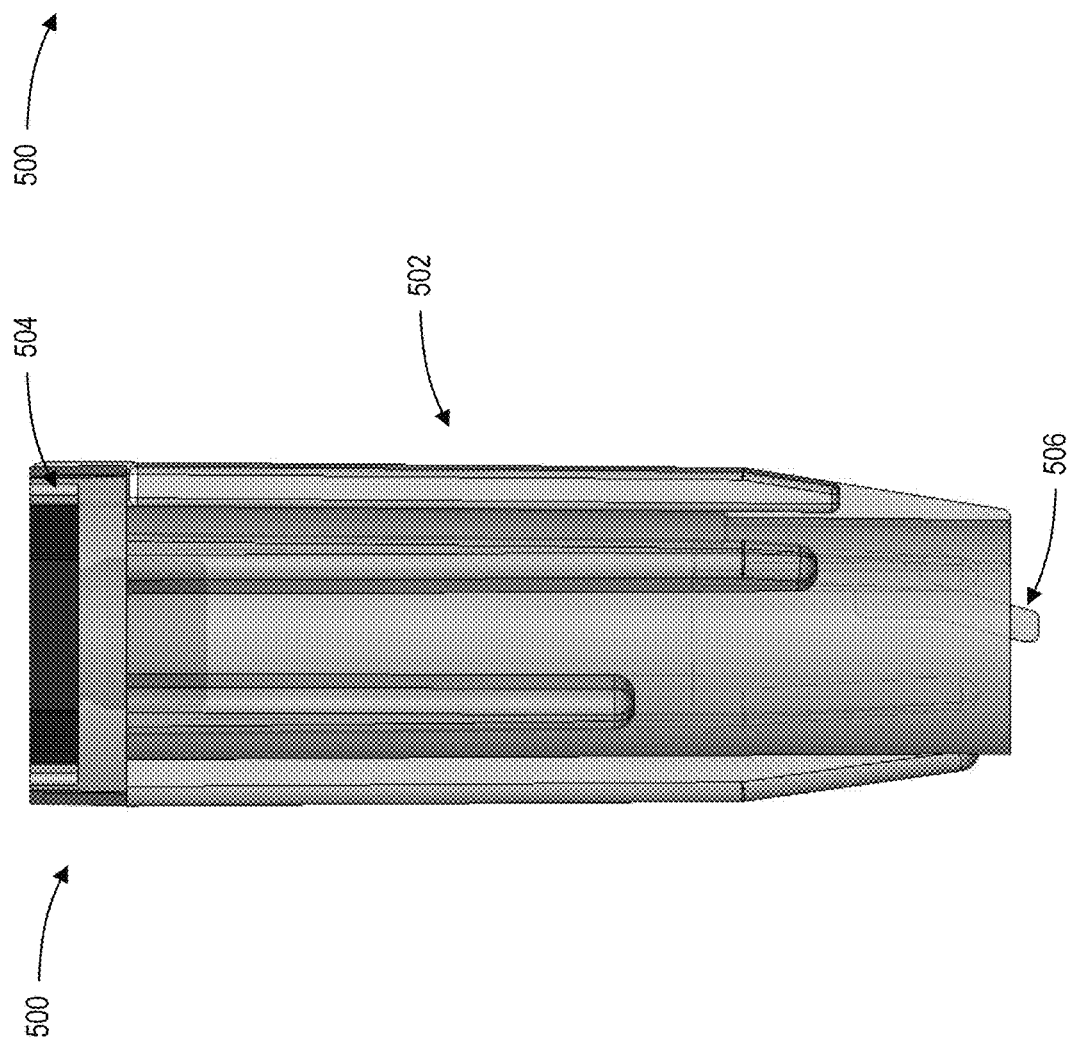
Figure 40B:
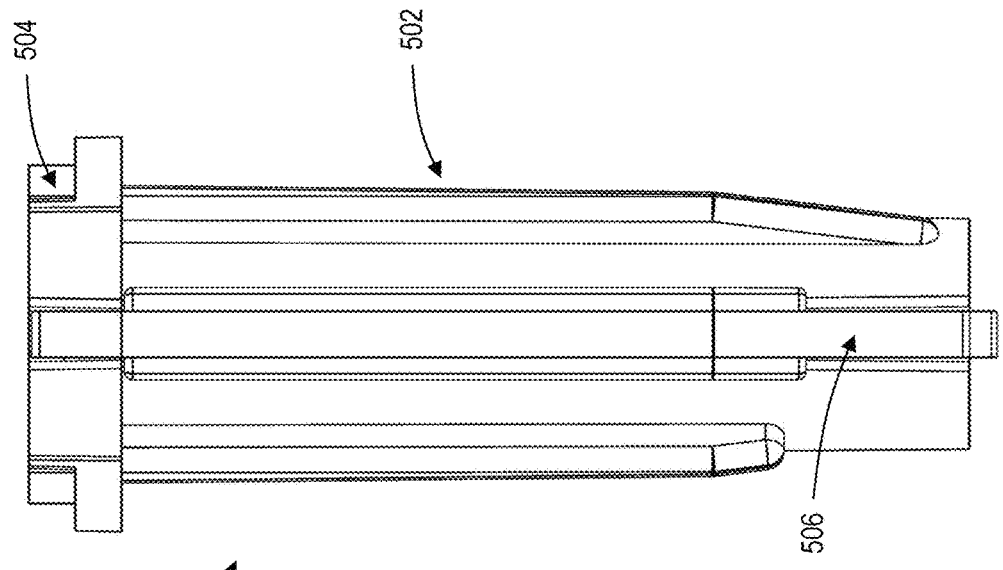
Figure 40A:
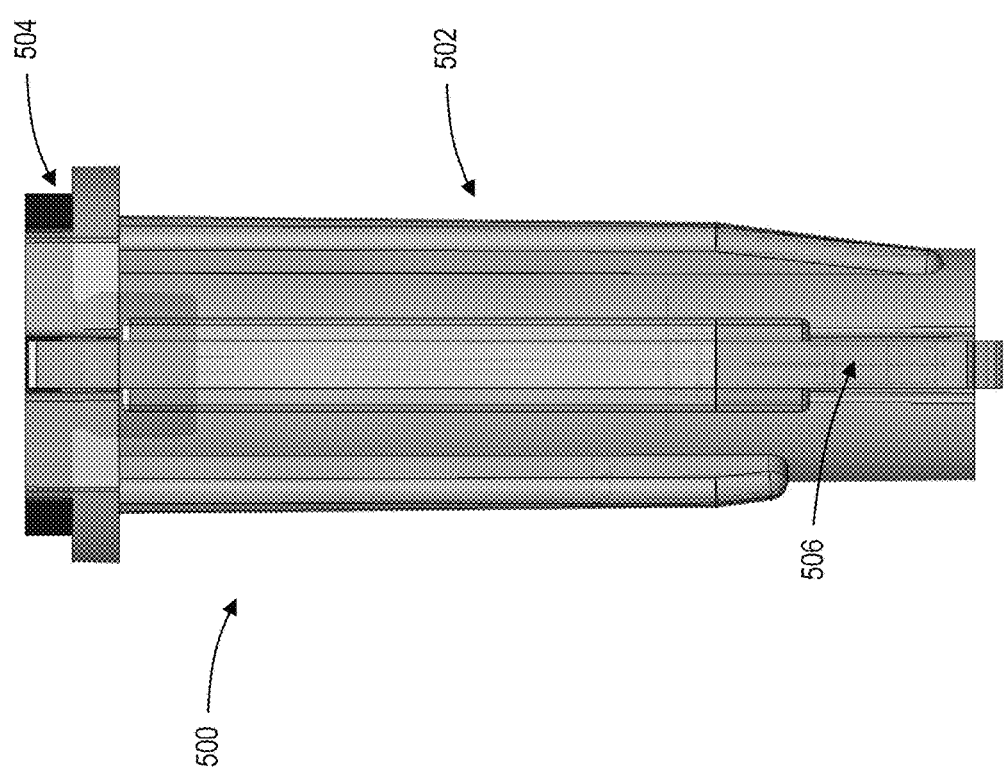
Figure 41A:
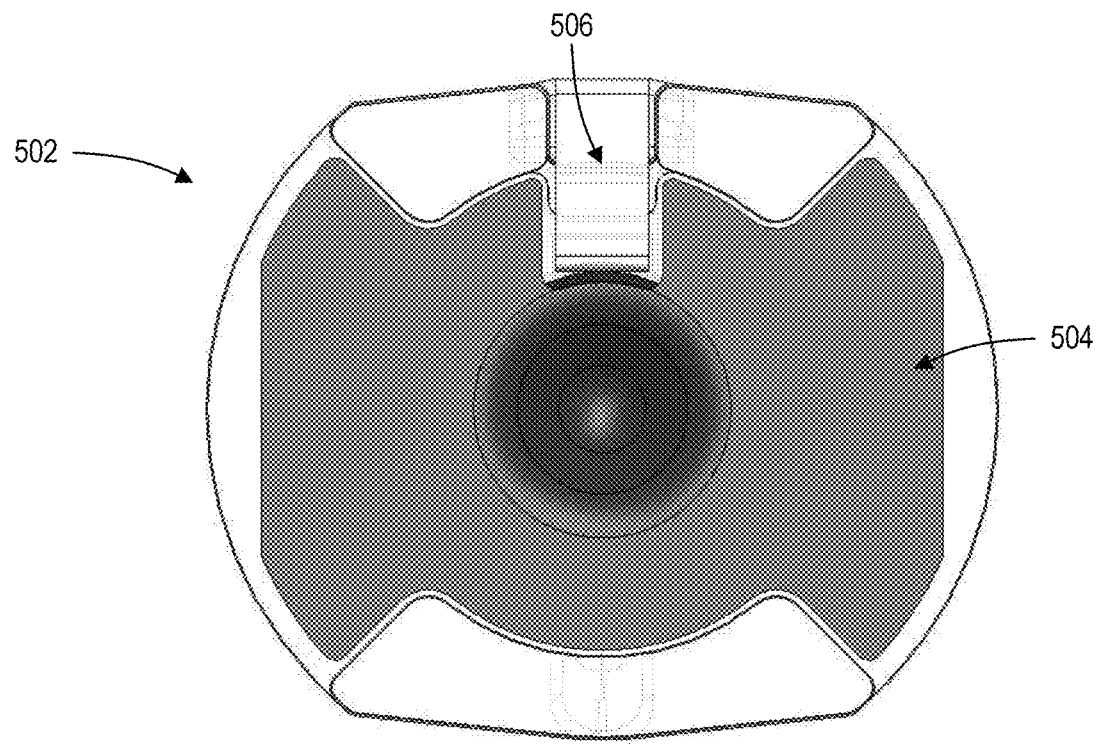
Figure 41B:
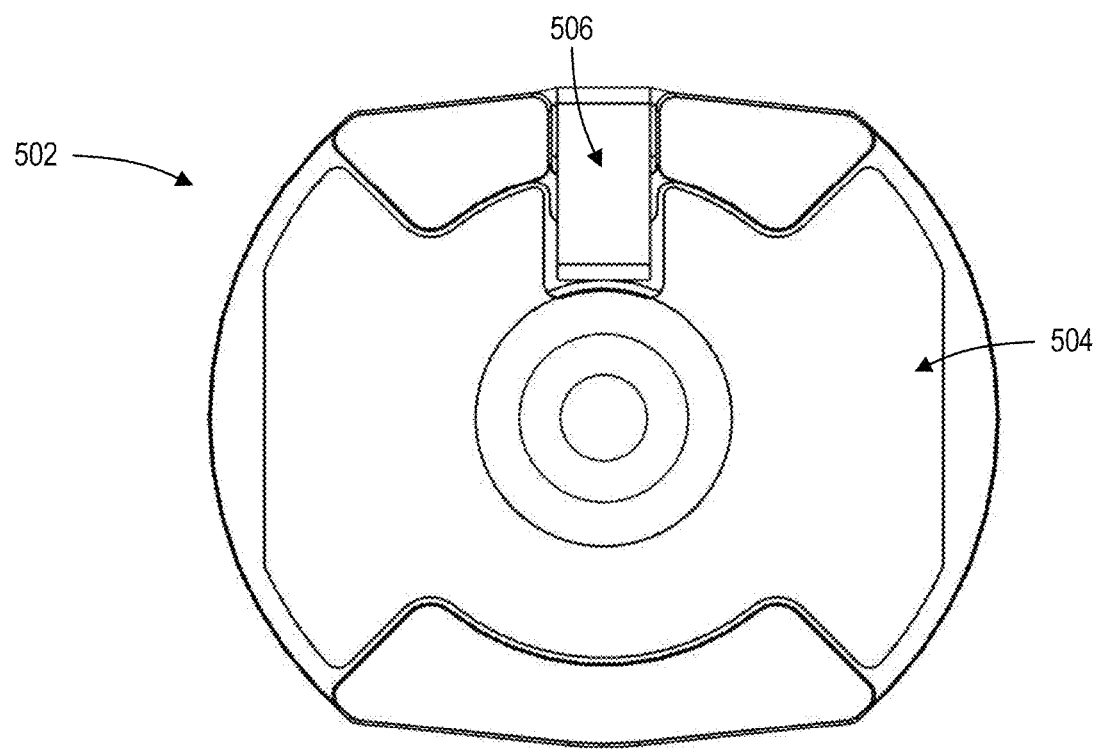
Figure 42A:
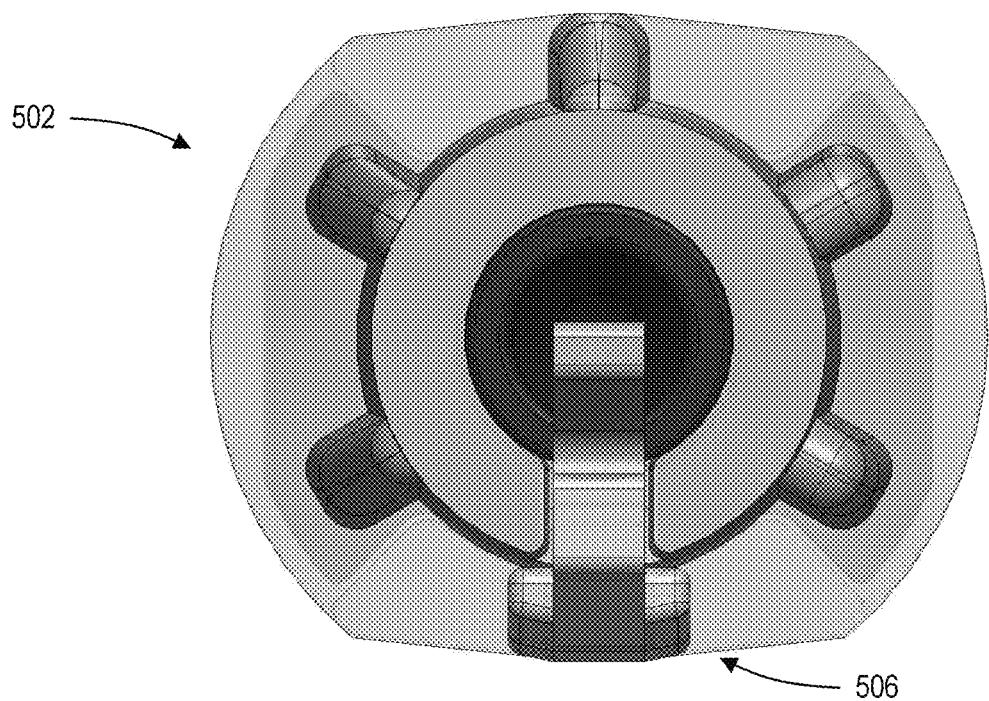
Figure 42B:
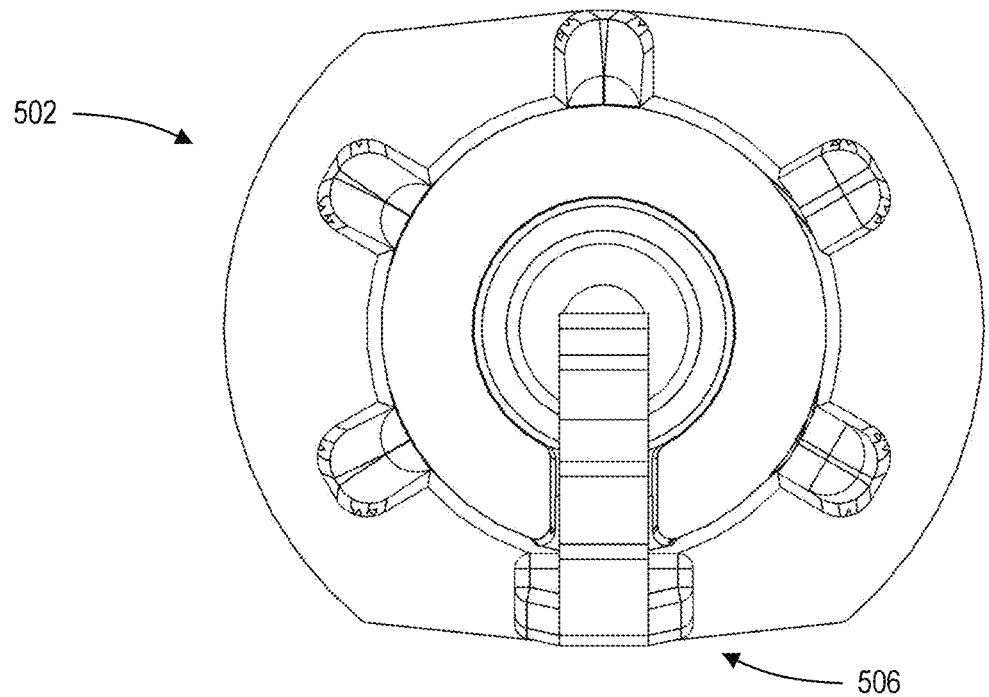
Figure 43B:
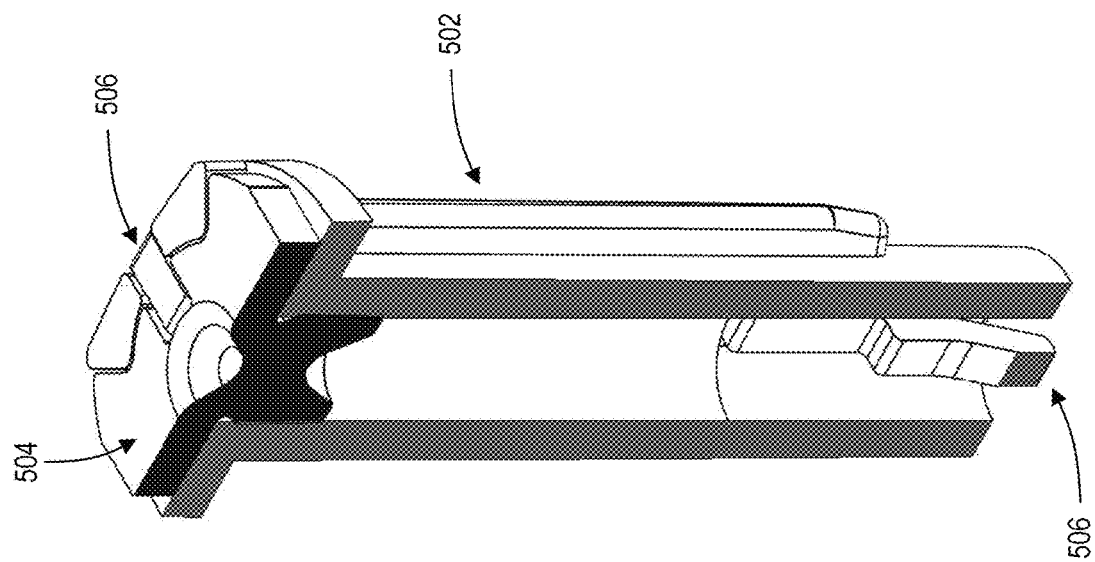
Figure 43A:
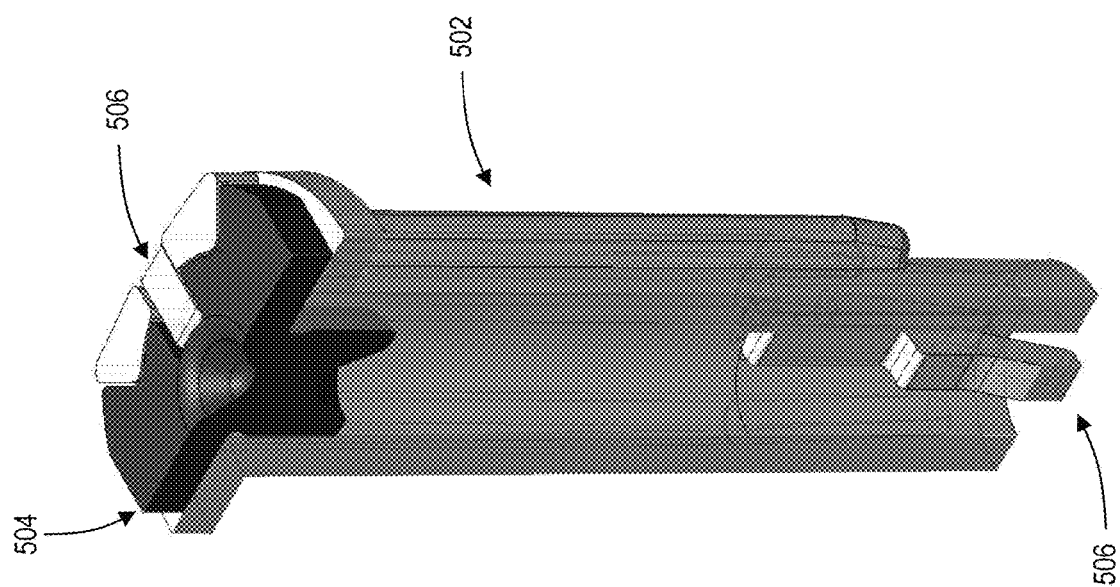
Figure 44B:
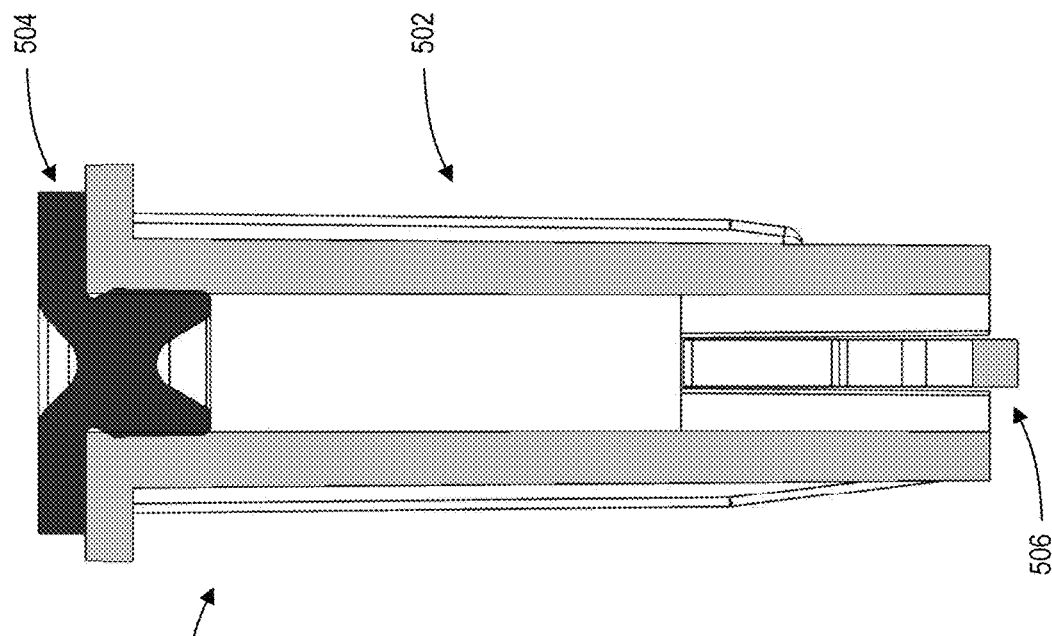
Figure 44A:
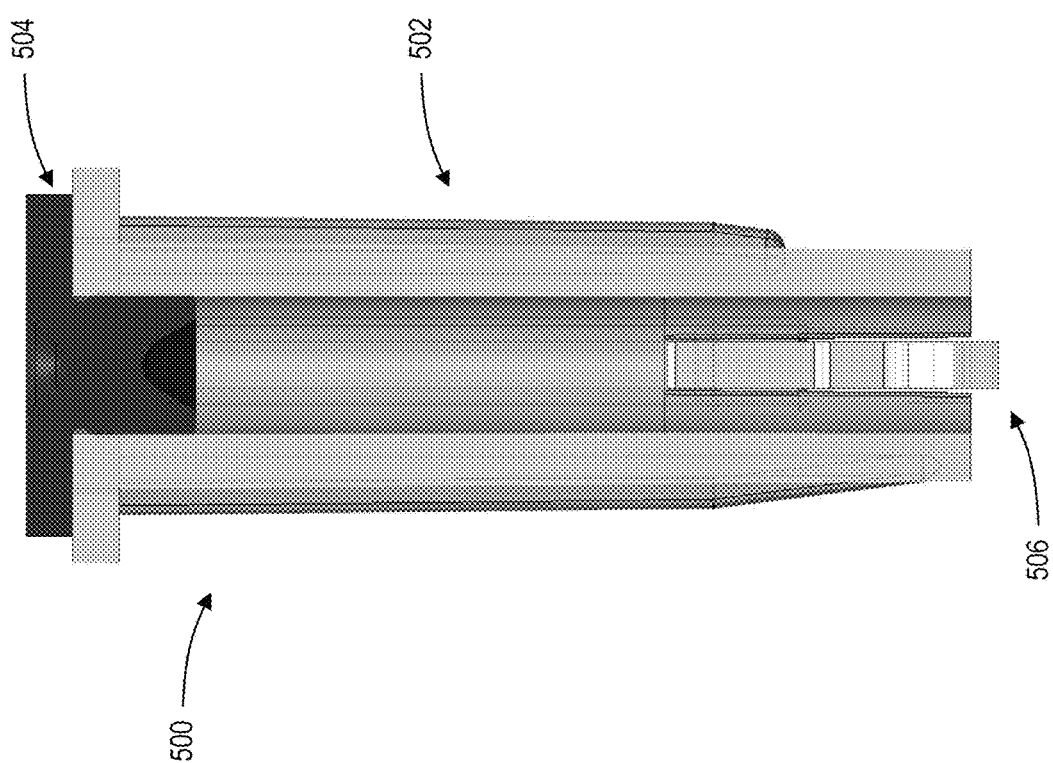
Figure 48B:
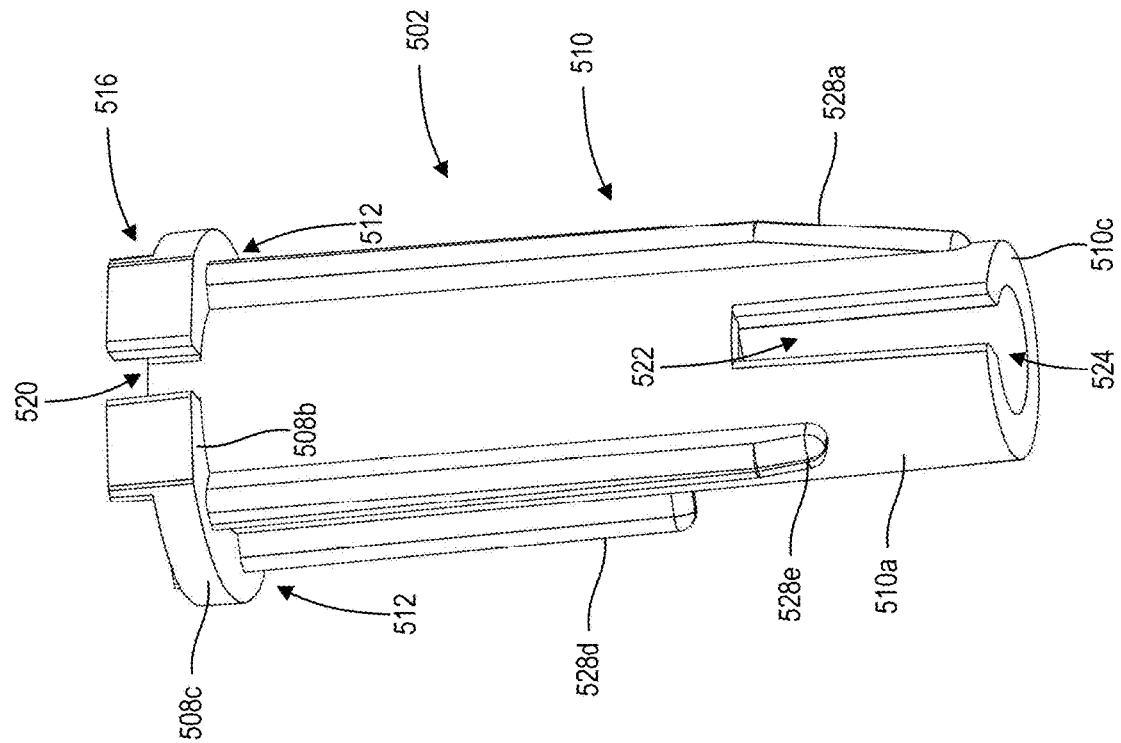
Figure 48A:
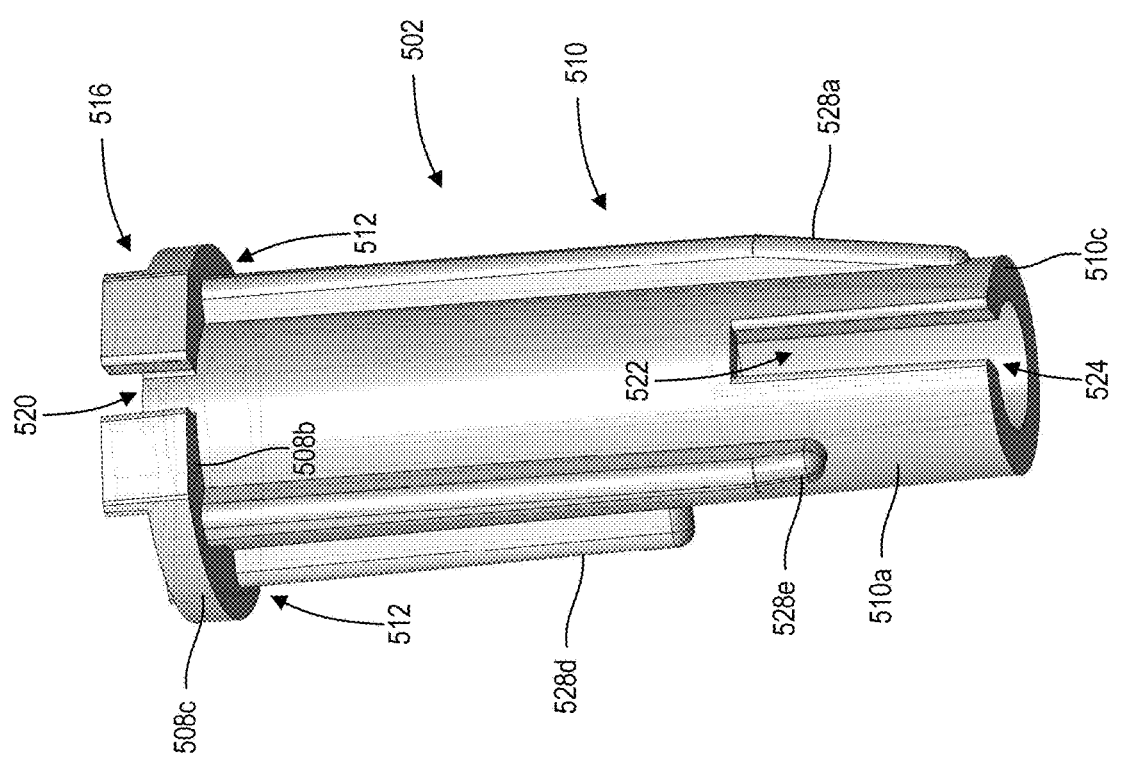
Figure 50B:
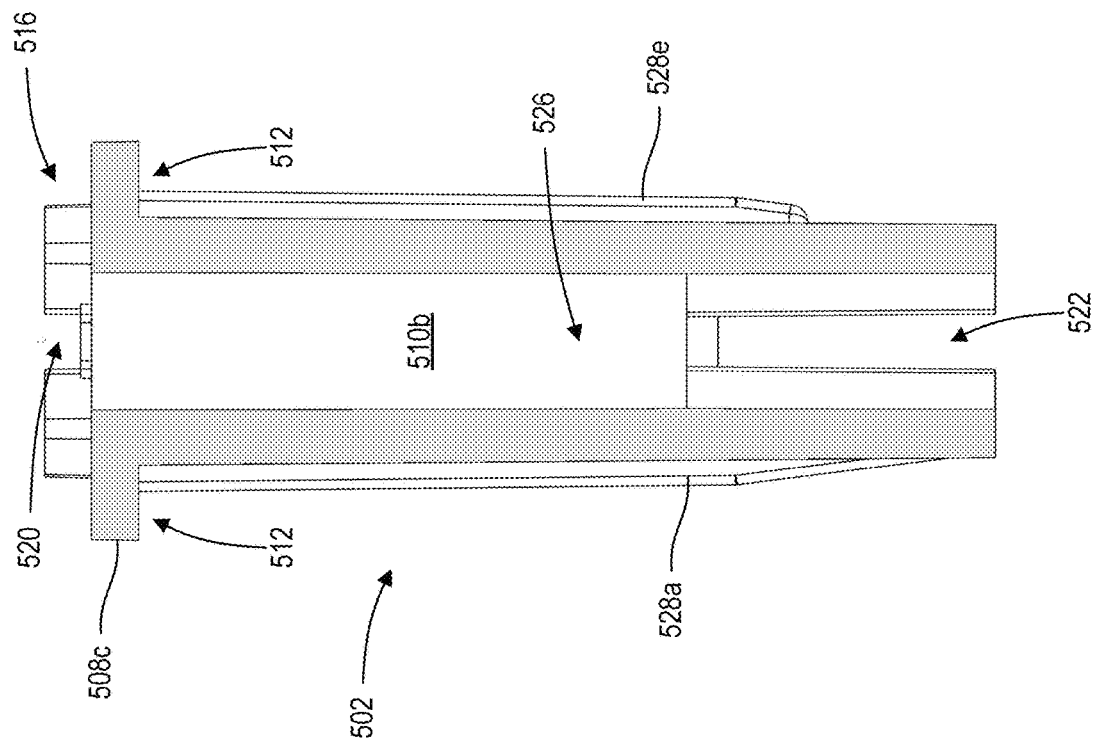
Figure 50A:
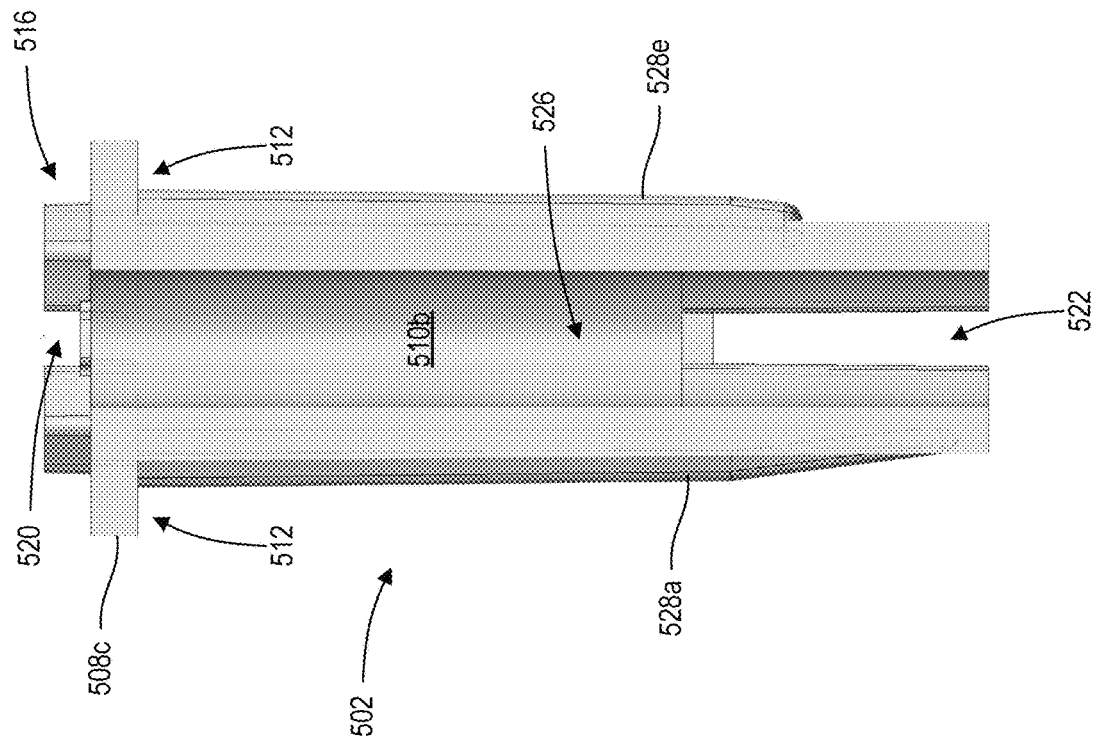
Figure 51:
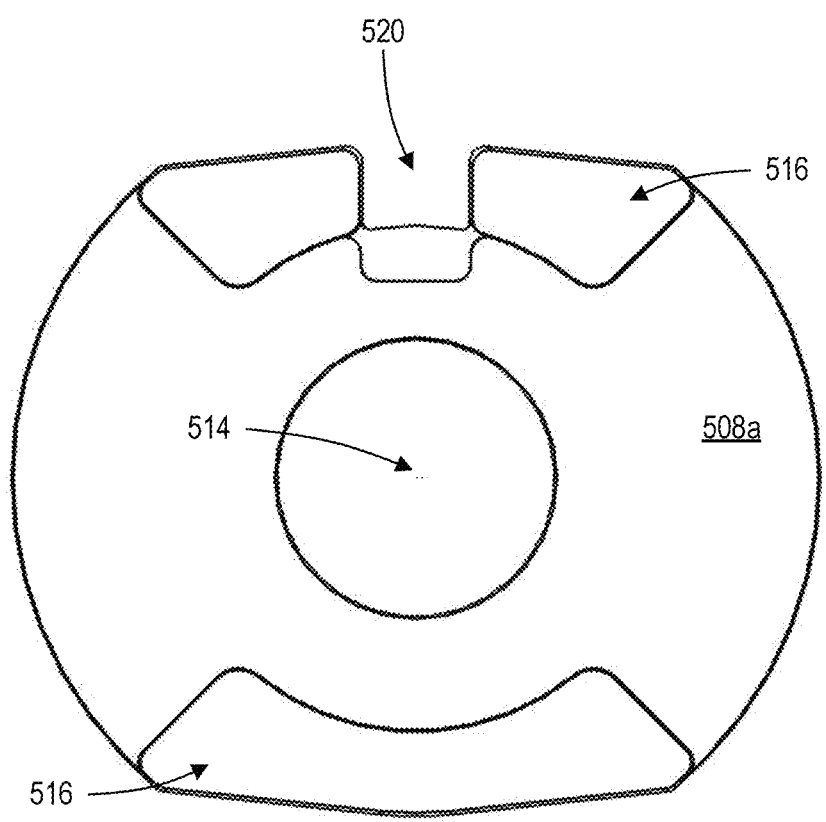
Figure 52A:
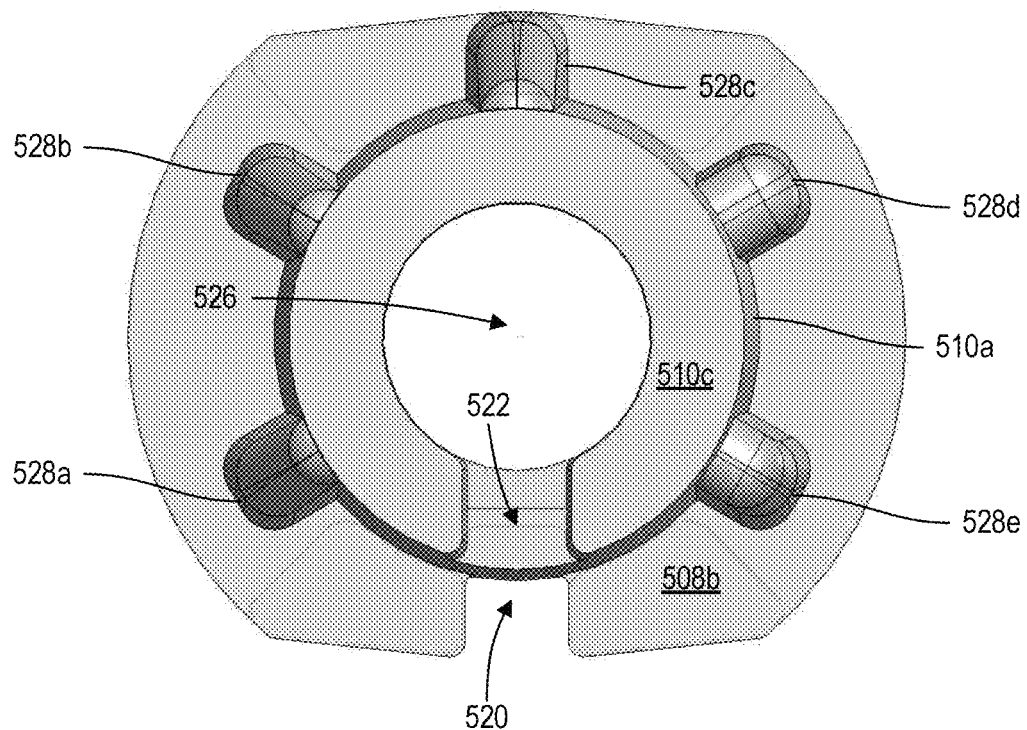
Figure 52B:
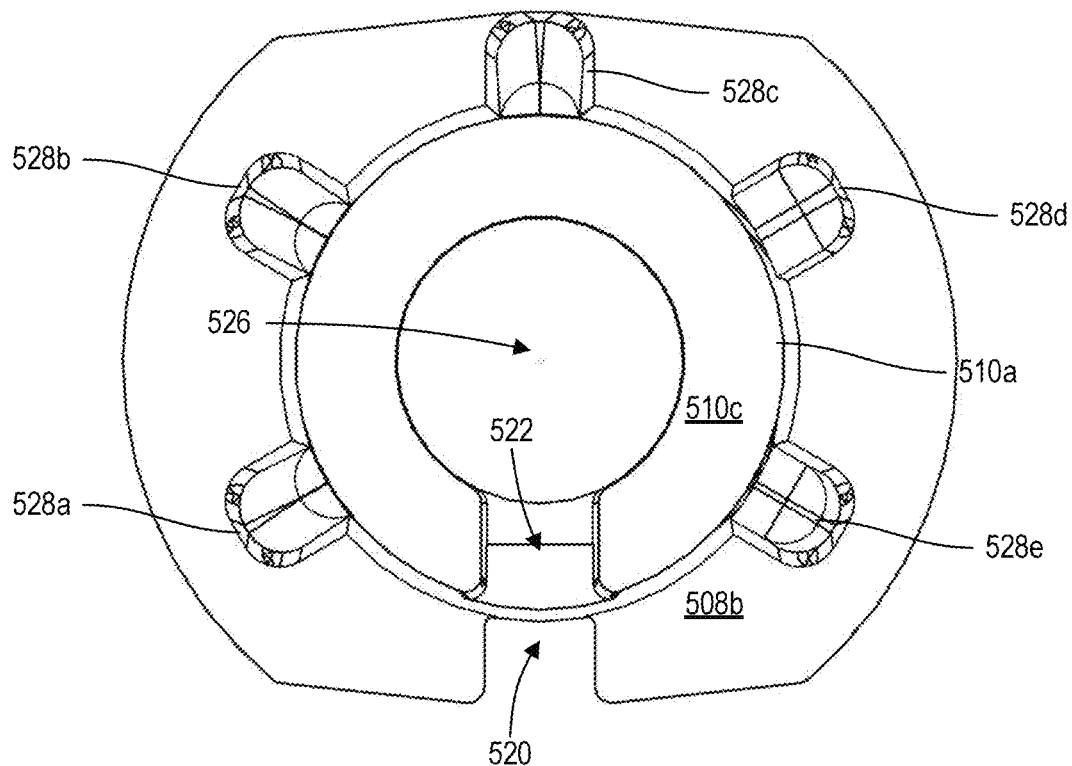

Referring now to FIGS. 34 and 35, the elastomeric ring 408 is shown in accordance with an exemplary embodiment. In this embodiment, the elastomeric ring 408 is generally cylindrical in shape and includes a first end surface 432, an opposed second end surface 434, and an outer wall 436. The outer wall 436 extends longitudinally between the first end surface 432 and the second end surface 434.

The elastomeric ring 408 also includes a bore 438 that extends from the second end surface 434 and into the elastomeric ring 408. The outer wall 436 includes an outer surface 436a and an inner surface 436b. The inner surface 436b defines a length of the bore 438 and further defines an inner volume 440 that is in open communication with the bore 438. The bore 438 and the inner volume 440 is shaped and dimensioned to accept the projection 430. That is, when the projection 430 is inserted into the elastomeric ring 408, the projection 430 is disposed within the bore 438 and the inner volume 440. The elastomeric ring 408 further includes a first and second band 442 that extend vertically from and perpendicular to the outer surface 436a. The bands 442 extend circumferentially around the outer wall 436. As will be discussed in further detail herein, when the plunger 400 is inserted into the vial assembly 500, the bands 442 provide an airtight seal within the vial assembly 500.

Referring now to FIGS. 36A and 36B-FIGS. 44A and 44B, the vial assembly 500 is shown in accordance with an exemplary embodiment. In this embodiment, the vial assembly 500 includes a vial 502, an elastomeric cap 504, and a stopping member 506. In some embodiments the vial 502 is formed of PDMS such that the vial 502 is transparent. Furthermore, in some embodiments, the elastomeric cap 504 is formed of a self-healing material.

With particular reference to FIGS. 44A and 44B-51A and 52B, the vial 502 includes a top wall 508 and a side wall 510 that extends vertically from and perpendicular to the top wall 508. The top wall 508 and the side wall 510 are generally cylindrical in shape and are concentric with one another.

The top wall 508 includes a top surface 508a, an opposed bottom surface 508b, and a side surface 508c that extends between the top surface 508a and the bottom surface 508b. The side surface 508c extends longitudinally from and perpendicular to the top surface 508a and the bottom surface 508b. Opposing sides of the top wall 508 extend beyond the side wall 510 such that the top wall 508 includes flanges 512. As will be discussed in further detail herein, the flanges 512 prevent the vial assembly 500 from moving from one position to another position until the vial assembly 500 is rotated. The top surface 508a of the top wall 508 defines an opening 514 that is shaped and dimensioned to accept a portion of the elastomeric cap 504.

The vial 502 also includes a first cap retention member 516 and a second cap retention member 518. The first cap retention member 516 and the second cap retention member 518 extend vertically from and perpendicular to the top surface 508a of the top wall 508. The first cap retention member 516 and the second cap retention member 518 are shaped and dimensioned to retain the elastomeric cap 504 on top of and within the vial 502. Furthermore, the first cap retention member 516 includes a notch 520 that extends through the top wall 508. The notch 520 is shaped and dimensioned to accept a proximal portion of the stopping member 506.

The side wall 510 includes an outer surface 510a, an opposed inner surface 510b, and the bottom surface 510c. The outer surface 510a and the inner surface 510b extend vertically from and perpendicular to the bottom surface 508b of the top wall 508 and the bottom surface 510c. The vial 502 further includes a notch 522 that extends vertically from the bottom surface 510c and extends between the outer surface 510a and the inner surface 510b. The notch 522 is shaped and dimensioned to accept a distal portion of the stopping member 506. The notch 520 and the notch 522 are aligned with one another such that the notches 520 and 522 retain the stopping member 506 when the stopping member 506 is coupled to the vial 502.

The bottom surface 510c of the side wall 510 defines an opening 524 that is shaped and dimensioned to accept the elastomeric ring 408 and a portion of the plunger 400. The inner surface 510b defines a bore 526 that extends between the opening 514 and the opening 524. When the plunger 400 is disposed within the bore 526 the bands 442 contact the inner surface 510b of the side wall 510.

The vial 502 further includes a plurality of ribs 528a-528e that extend from and along the outer surface 510a of the side wall 510. In this embodiment, the ribs 528a-528c have the same length. The ribs 528*d* and 528*e* have a shorter length than the ribs 528*a*-258*c*. As will be discussed in further detail herein, at least two of the ribs 528 prevent the vial assembly 500 from rotating beyond a given position.

Figure 53:
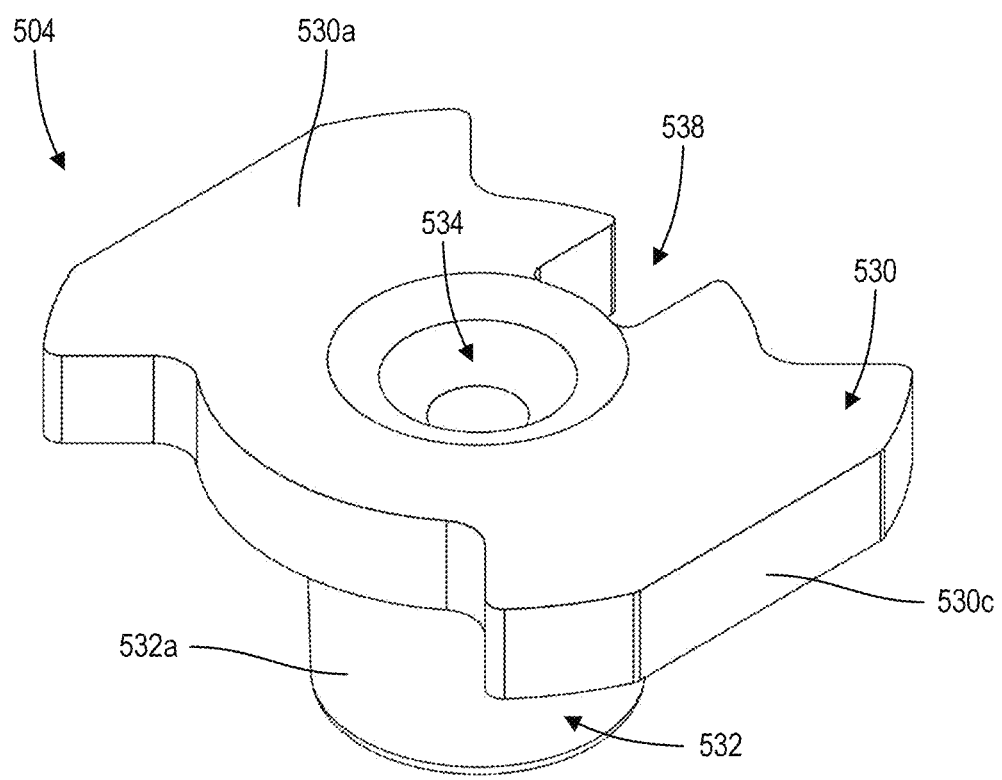

With particular reference to FIGS. 53 and 54, the elastomeric cap 504 includes a top wall 530 and a side wall 532 that extends vertically from the top wall 530. The top wall 530 includes a top surface 530*a*, an opposed bottom surface 530*b*, and a side surface 530*c* that extends between the top surface 530*a* and the bottom surface 530*b*. The side wall 532 includes an outer surface 532*a*, an opposed inner surface 532*b*, and a bottom surface 532*c* that extends longitudinally from and perpendicular to the outer surface 532*a* and the inner surface 532*b*. The outer surface 532*a* and the inner surface 532*b* extends vertically from the bottom surface 530*b* of the top wall 530 and the bottom surface 532*c*.

The top wall 530 is shaped and dimensioned to fit between the first cap retention member 516 and the second cap retention member 518 such that the first cap retention member 516 and the second cap retention member 518 couple the elastomeric cap 504 to the vial 502. When the elastomeric cap 504 is coupled to the vial 502, the side wall 532 extends into the bore 526 such that the outer surface 532*a* of the side wall 532 contacts the inner surface 510*b* of the side wall 510 of the vial 502. Furthermore, when both the elastomeric ring 408 of the plunger 400 and the elastomeric cap 504 are disposed within the bore 526, the elastomeric ring 408 and the elastomeric cap 504 provide an airtight seal. As such, the region of the bore 526 between the elastomeric ring 408 and the elastomeric cap 504 includes an airtight environment.

Furthermore, the top surface 530*a* of the top wall 530 defines a top recess 534 and the inner surface 532*b* of the side wall 532 defines a bottom recess 536 such that the elastomeric cap 504 includes a region of elastomeric material between the recesses 534 and 536. As will be discussed in further detail herein, when the syringe 16 is coupled to the needle 330, the needle 330 extends through the region of the elastomeric cap 504 between the recesses 534 and 536 and into the bore 526 of the vial 502. Since the elastomeric cap 504 can be formed of a self-healing material, in these embodiments, after the needle 330 pierces the elastomeric cap 504 and the needle has been removed from the elastomeric cap 504, the elastomeric cap 504 heals to seal the vial 502. The top wall 530 also includes a notch 538 that extends between the top surface 530*a* and the bottom surface 530*b*. The notch 538 is shaped and dimensioned to accept a proximal end of the stopping member 506 such that the notch 538 retains a portion of the stopping member 506 when the stopping member 506 is coupled to the vial 502.

With particular reference to FIGS. 55A and 55B, the stopping member 506 includes a plunger interface 540, a neck 542, and a hook 544. The plunger interface 540 defines a distal end and a proximal end of the stopping member 506 and the neck 542 extends between the plunger interface 540 and the hook 544.

The plunger interface 540 includes a distal end surface 546, a bottom surface 548, and a proximal end surface 550. The bottom surface 548 extends between the distal end surface 546 and the proximal end surface 550. The distal end surface 546 is positioned opposite to the proximal end surface 550. The bottom surface 548 has a similar shape and dimension as the top surface 418 of a projection member 414. When the vial assembly 500 is coupled to the plunger 400, the plunger interface 540 is disposed within the groove 416 such that at least a portion of the bottom surface 548 of the plunger interface 540 contacts a top surface 418 of a projection member 414. The plunger interface 540 and the neck 542 define a notch 552. When the stopping member 506 is coupled to the vial 502 the plunger interface 540 is disposed within the notch 522 of the 502. Furthermore, when the stopping member 506 is coupled to the vial 502, the notch 522 contacts a portion of the side wall 510 that defines an end of the notch 522. As such, in this position, the notch 522 retains the stopping member 506.

The neck 542 has a length that is similar to a distance between the notch 522 and the top surface 508*a* of the vial 502. As such, when the stopping member 506 is coupled to the vial 502, a portion of the neck 542 extends through the notch 520 of the first cap retention member 516 and the hook 544 extends over and contacts the top surface 508*a* to couple the stopping member 506 to the vial 502.

Figure 56:
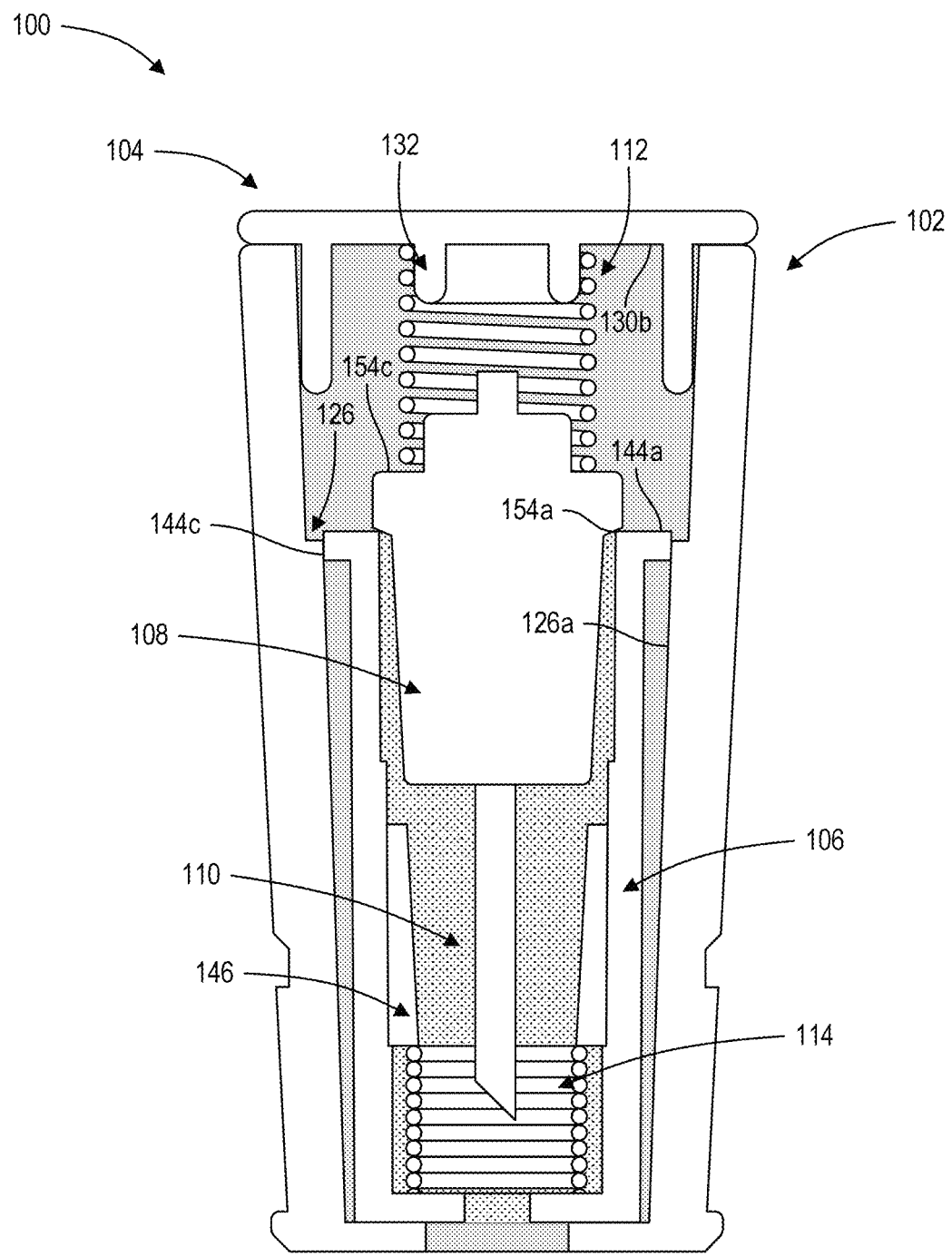
FIG. 56 depicts the lancet in an undeployed position in accordance with an exemplary embodiment of the present disclosure.
Figure 57:
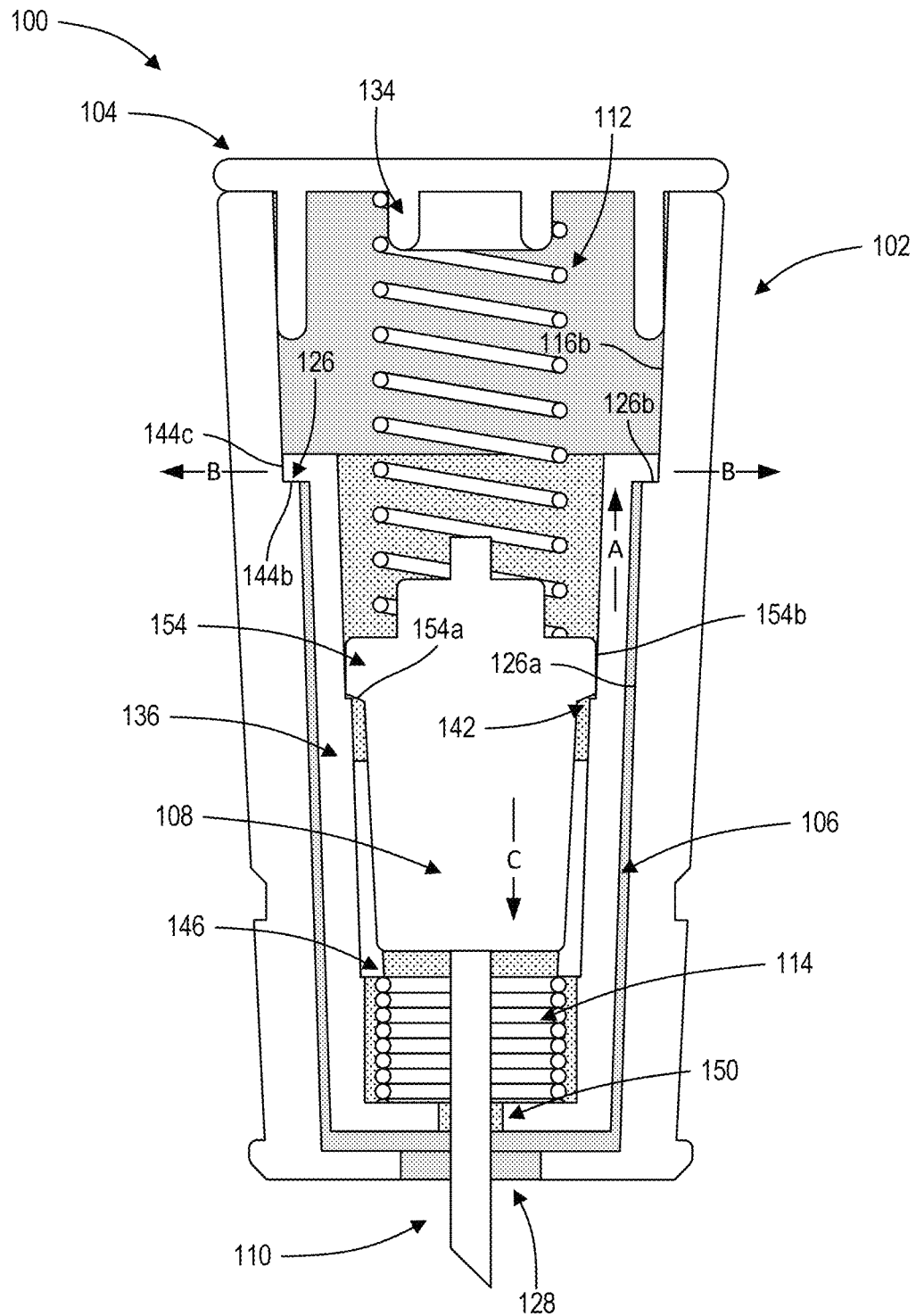
FIG. 57 depicts the lancet in a deployed position in accordance with an exemplary embodiment of the present disclosure.
Figure 58:
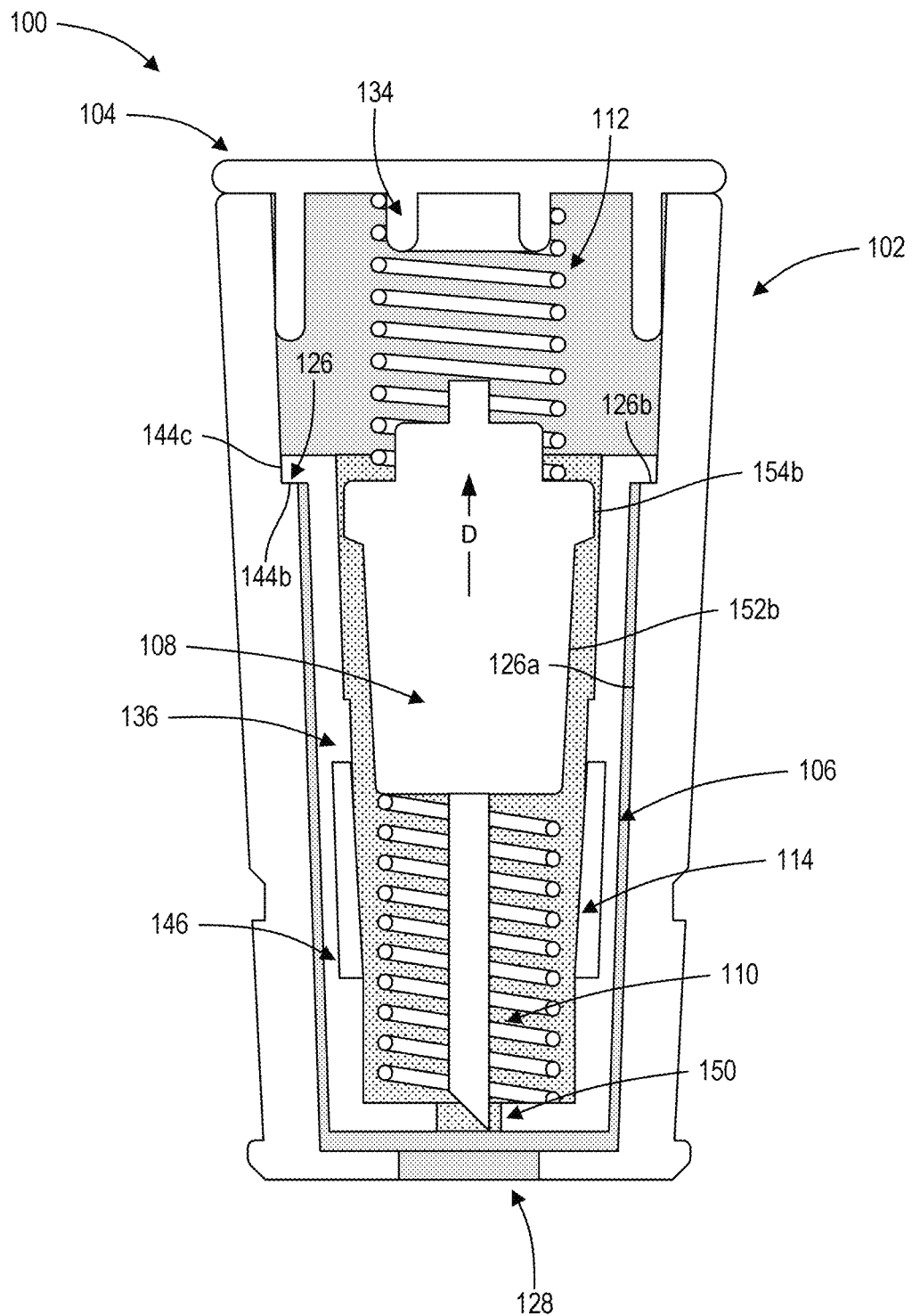
FIG. 58 depicts the lancet in a retracted position in accordance with an exemplary embodiment of the present disclosure.

As depicted in FIGS. 56-57, the lancet 100 is moveable between an undeployed position (FIG. 56), a deployed position (FIG. 57), and a retracted position (FIG. 58).

In the undeployed position (before the lancet 100 is inserted into the cartridge 12; FIG. 56) the injection spring 112 and the retraction spring 114 are in a compressed state. In the compressed state, the retraction spring 114 extends vertically between the bottom wall 138 (FIG. 56) and a proximal end of the locking members 146. More specifically, a distal end of the retraction spring 114 contacts a lower surface of the proximal end of the locking members 146 and a proximal end of the retraction spring 114 contacts the inner surface 138*b* (FIG. 56) of the bottom wall 138.

When in the undeployed position the outer surface 144*c* contacts the inner surface 126*a* of the columns 126 which compresses the side wall 136 inwardly. Furthermore, the bottom surface 154*a* of the second cylinder 154 contacts and rests upon the top surfaces 144*a* of the ledges 144 (FIG. 56) such that the ledges 144 support the needle frame 108 in the undeployed position. In this position, the injection spring 112 is prevented from decompressing (due to the second cylinder 154 (FIG. 56) resting upon the ledges 144) and the needle 110 is disposed completely within the inner volume 140 (FIG. 56) of the inner sleeve 106.

Figure 59:
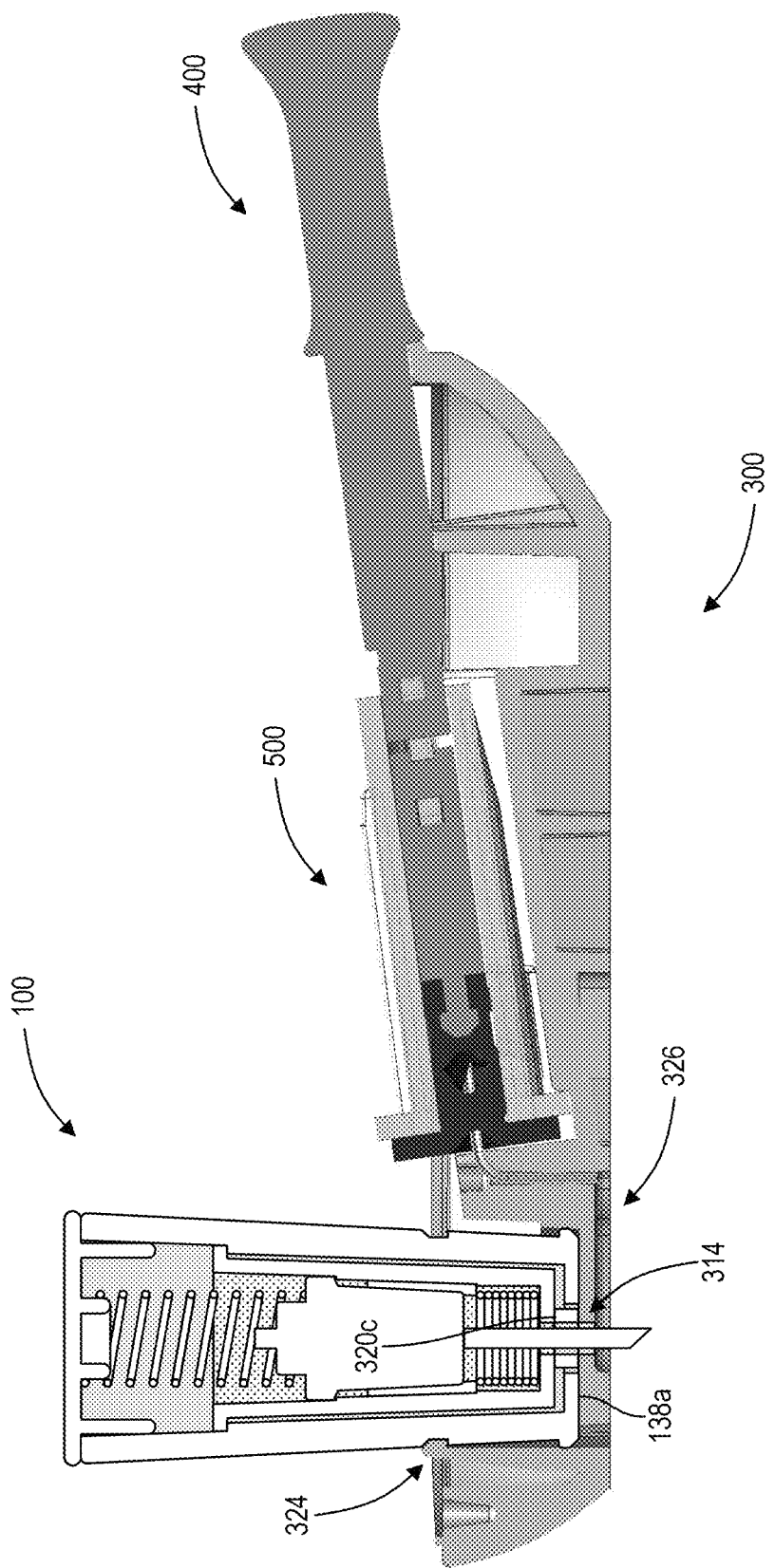
FIG. 59 depicts the lancet couped to the base wherein the lancet is in the deployed position in accordance with an exemplary embodiment of the present disclosure.

When the lancet 100 is inserted into the cartridge 12, the engagement of the lancet with the cartridge 12 causes the lancet 100 to automatically move from the undeployed position to the deployed position. Furthermore, when the lancet 100 is inserted into the cartridge 12, the hooks 324 of the locking members 322 are disposed within and coupled to the notch 122 via a snap fit (FIG. 59).

When the lancet 100 is coupled to the base 300 (FIGS. 59 and 60), the inner circular projection 320 (FIGS. 59 and 60) extends through the aperture 128 to contact the bottom wall 138. Specifically, the top surface 320*c* of the inner circular projection 329 (FIGS. 59 and 60) contacts the outer surface 138*a* of the bottom wall 138 (FIGS. 59 and 60) which forces the inner sleeve 106 to move vertically upward in the direction of arrow A (FIG. 57) within the housing 102. This vertical movement causes the ledges 144 to extend vertically above the top surfaces 126*b* of the columns 126. Moving beyond the top surfaces 126*b* of the columns 126 allows the side wall 136 to decompress and expand in the direction of arrow B (FIGS. 58 and 60) and extend toward the inner surface 116*b* of the side wall 116. In this position, the bottom surface 144*b* of the ledges 144 rest upon the top surfaces 126*b* of the columns 126 and the outer surfaces 144*c* of the ledges 144 contact the inner surface 116*b* of the side wall 116.

The expansion of the side wall 136 causes the inner volume 140 of the inner sleeve 106 to have a larger width relative to when the inner sleeve 106 is in the undeployed position such that at least a portion of the side wall 136 has a larger width than the second cylinder 154 (the widest portion of the needle frame 108 which allows the needle frame 108 to move vertically downward in the direction of arrow C).

Furthermore, the injection spring 112 also causes the needle frame 108 to move in the direction of arrow C as the ledges 144 no longer prevent the injection spring 112 from expanding. The force applied by the injection spring 112 causes the needle frame 108 (and therefore the needle 110) to travel with a force that is sufficient to cause the needle 110 to puncture the skin of a subject wearing the dermal patch system 10. Stated another way, the injection spring 112 causes the needle 110 to extend through the aperture 150 of the inner sleeve 106, through the aperture 128 of the housing 102, and through the needle aperture 314 of the base 300 to puncture the skin of a subject. In the deployed position, the bottom surface 154a of the second cylinder 154 rests upon the columns 142 and at least a portion of the outer surface 154b of the second cylinder 154 contacts the inner surface 136b of the side wall 136.

Figure 60:
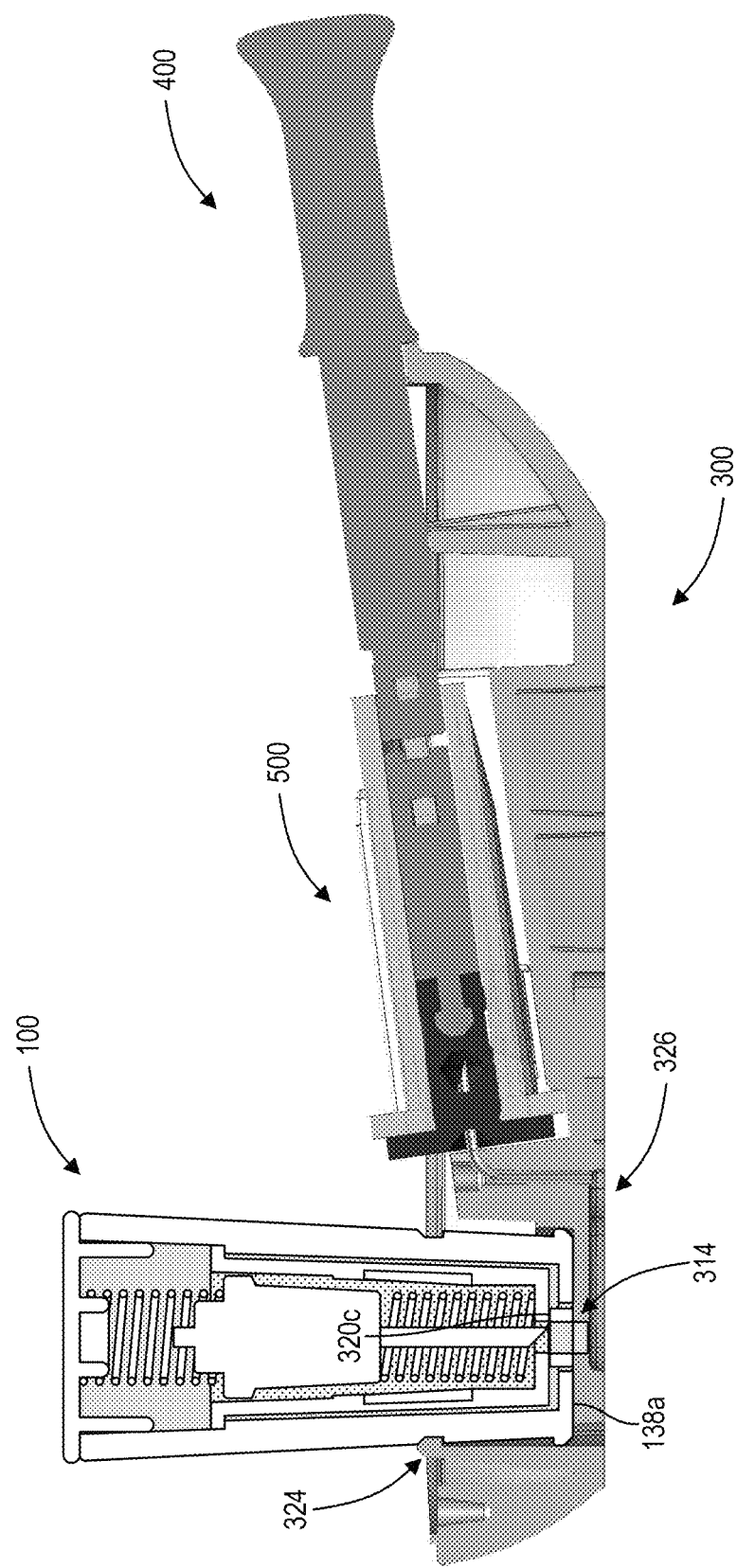
FIG. 60 depicts the lancet couped to the base wherein the lancet is in the retracted position in accordance with an exemplary embodiment of the present disclosure.

While moving in the direction of arrow C, the outer surface 152b contacts the locking members 146 which causes a proximal portion of locking members 146 that is aligned with an opening 148 to extend into the opening. In this position, the locking members 146 no longer contact the retraction spring 114 thereby allowing the retraction spring 114 to decompress and expand. When decompressed, the retraction spring 114 contacts the outer surface 152b of the first cylinder 152 which causes needle frame 108 to also move in the direction of arrow D. That is after moving to the deployed position, the retraction spring 114 causes the needle 110 to retract back into the inner volume 140 of the inner sleeve 106 via the needle aperture 314 of the base 300 and the apertures 128 and 150 of the lancet 100. After penetrating the skin of a subject, the refraction spring 114 causes the needle 110 to automatically retract back into the housing of the lancet 100 thereby placing the lancet 100 in the retraced position (FIGS. 58 and 60).

Figure 61:
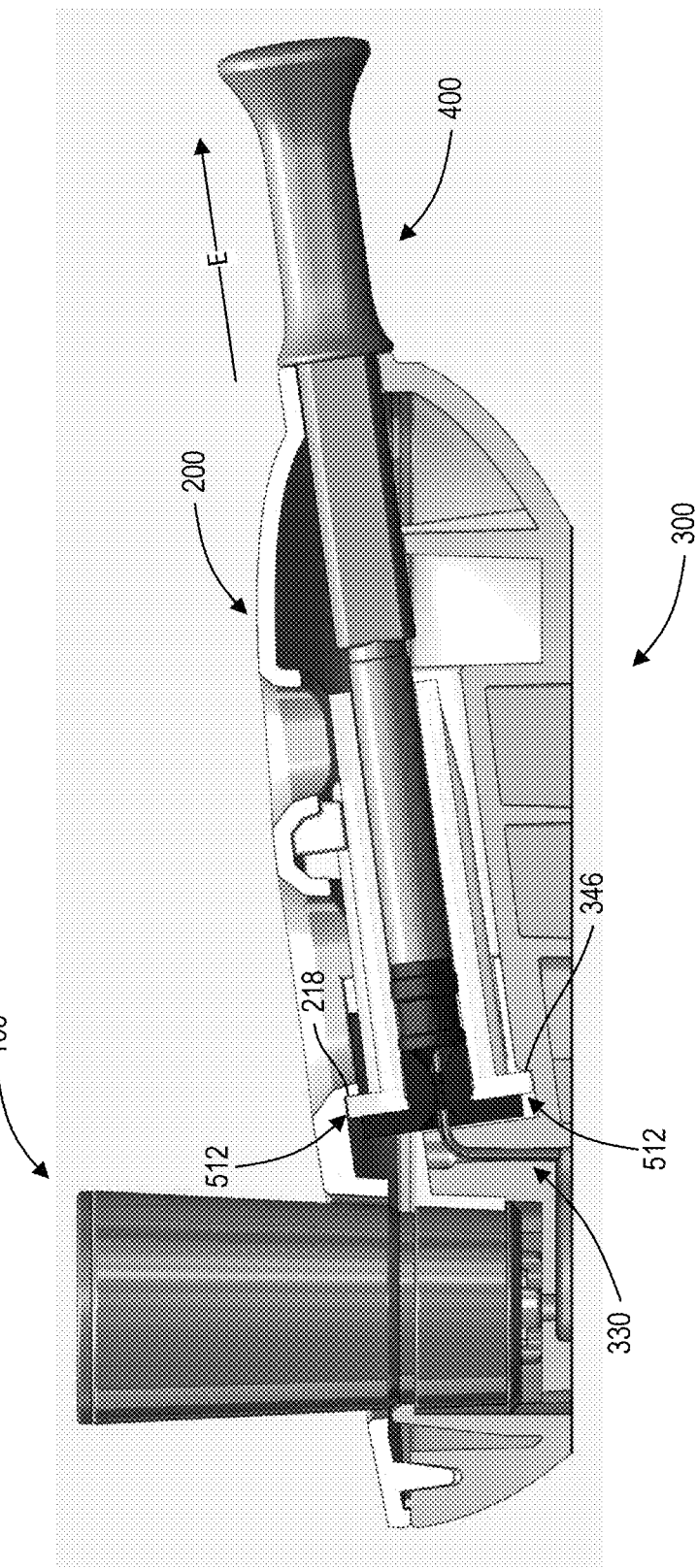
FIG. 61 depicts the dermal patch system wherein the plunger is in an undeployed position in accordance with an exemplary embodiment of the present disclosure.
Figure 62:
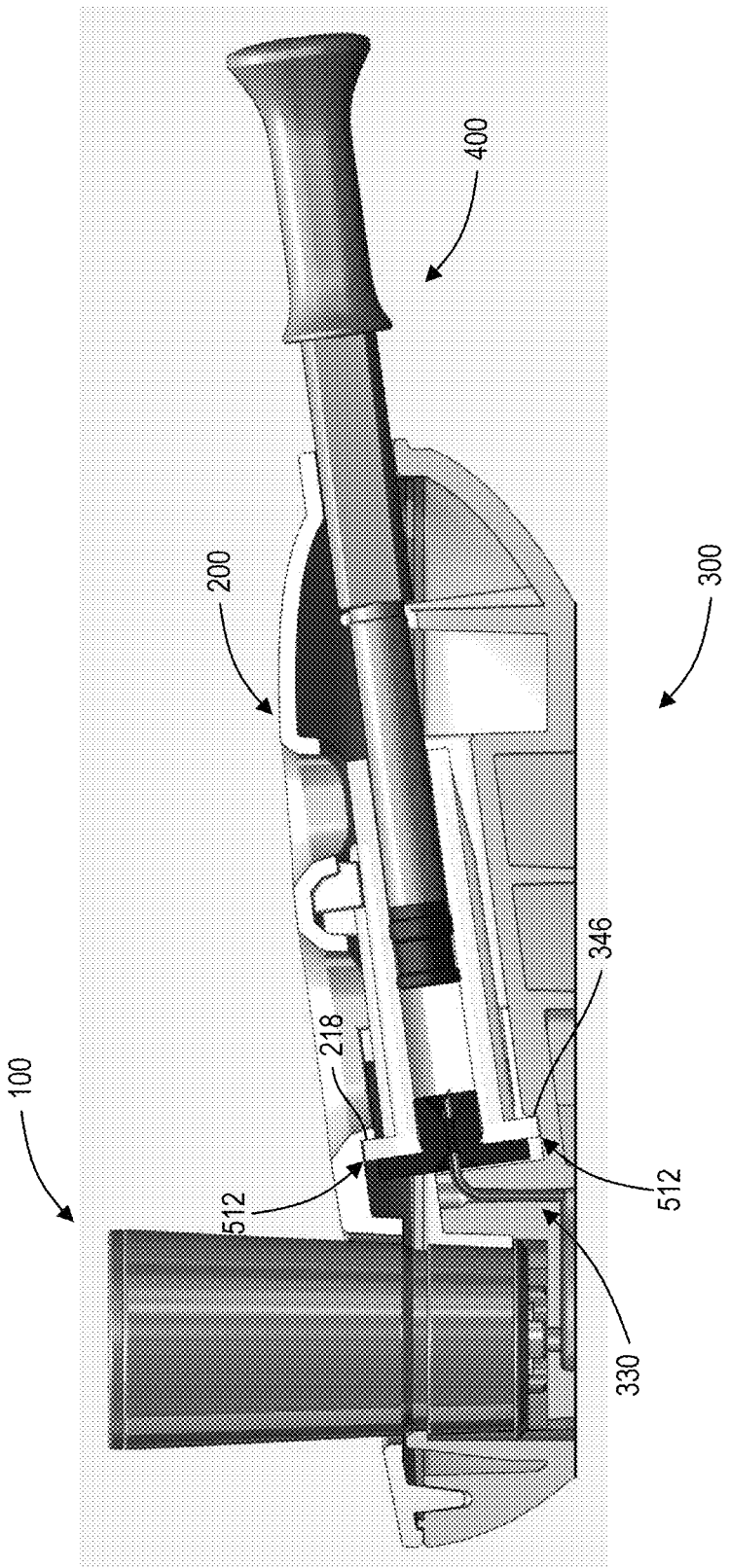
FIG. 62 depicts the dermal patch system wherein the plunger is in a deployed position in accordance with an exemplary embodiment of the present disclosure.

Subsequent to puncturing the skin, the needle 110 retracts into the lancet 100 and a physiological sample pools within the physiological sample well 326 of the base 300. When the physiological sample is within the physiological sample well 326, a user pulls the plunger 400 in the direction of arrow E to move the plunger from a first position (FIG. 61) to a second position (FIG. 62). Stated another way, when the physiological sample is within the physiological sample well 326, a user moves the plunger 400 from an undeployed position to a deployed position. Moving the plunger from the undeployed position to the deployed position creates a vacuum within the vial 502. This vacuum causes the physiological sample to travel to the vial 502 via the needle 330. Furthermore, as depicted in FIGS. 61 and 62, when the vial assembly is in a first position (also referred to as a "sample collection position") a flange 512 of the vial 502 contacts a proximal surface of the protrusion 346 of the base 300 and another flange 512 of the vial 502 contacts a proximal surface of the locking wall 218 of the cover 200. This contact prevents the vial assembly 500 from moving with the plunger 400 when a user pulls the plunger 400. Before or after pulling the plunger 400 to draw the physiological sample into the vial 502, the user may verify that the physiological sample has been drawn by viewing the physiological sample in the vial 502 via the vial viewing aperture 208.

Since the vial assembly 500 remains stationary as the plunger 400 is pulled, the plunger interface 540 of the stopping member 506 contacts various projection members 414 until the plunger interface 540 contacts the top surface 424 and the side surface 426 of the stopping wall 422. In this position, the plunger 400 cannot be pulled further as the flanges 512, the locking wall 218 of the cover 200, and the protrusion 346 of the base 300 prevent further movement of the plunger 400. The amount the plunger moves can determine the strength of the generated vacuum and an amount of physiological sample drawn into the vial 502. An amount of physiological sample drawn into the vial 502 may be controlled by a distance between an initial and a final position of the plunger 400 as allowing the plunger 400 to travel further allows more physiological sample to be drawn into the vial 502. Accordingly, the dermal patch system 10 can be configured to draw various amounts of physiological sample into the vial 502 (e.g., 50 µL, 100 µL, 200 µL, etc.). By way of example, in various embodiments, the volume of the physiological sample that is received by the vial can be, for example, in a range of about 10 µL to about 200 µL, e.g., in a range of about 50 µL to about 100 µL.

Also, the inner diameter of the needle 330 can be varied between approximately 0.159 mm to 0.603 mm to control an amount of physiological sample drawn into the vial 502. Furthermore, the shape of the projection members 414 of the plunger 400 and the shape of the plunger interface 540 of the stopping member 506 can prevent a user from pushing the plunger 400 into the vial 502 which may cause an inadvertent ejection of physiological sample.

As noted above, in various embodiments, an amount of the physiological sample drawn into the vial 502 is proportional to a distance travel by plunger 400 when using the plunger to generate a vacuum. That is, the greater the distance traveled by the plunger 400 the greater an amount of physiological sample drawn into the vial 502. The distance traveled by the plunger 400 can be determined by a position of the stopping member 506 and a position of the plunger interface 540. While the stopping member 506 and the plunger interface 540 are depicted in one position, in other embodiments, the stopping member 506 and the plunger interface 540 may have a different position which allows the plunger 400 to draw more or less physiological sample into the vial 502 than the embodiment depicted herein.

The vial assembly 500 can be placed in a vial storage position, which allows a user to store the vial assembly 500 within the cartridge 12. As will be discussed in further detail herein, the user can rotate the vial assembly 500 by rotating the plunger 400. However, it is undesirable to place the vial assembly 500 in the vial storage position before drawing the physiological sample into the vial 502. In this embodiment, the shape and dimension of the shaft 404 and the U-shaped locking feature 348 can prevent the user from rotating the plunger 400 until after the user has moved the plunger to the deployed position. That is, in the undeployed position, the flat surfaces 412 of the shaft 404 are vertically disposed within the U-shaped locking feature 348 which prevents a user from rotating the plunger 400. If a user attempts to rotate the plunger 400 while the plunger 400 is in the undeployed position, the flat surfaces contact the U-shaped locking feature 348 thereby preventing rotation. When the plunger 400 is moved to the deployed position, the rod 406 is disposed within the U-shaped locking feature 348. The rod 406 has a smaller diameter than the U-shaped locking feature 348 which allows a user to rotate the plunger 400 when the plunger 400 is in the deployed position. Stated another way, features of the base 300 and the plunger 400 prevent a user placing the vial assembly 500 in a vial storage position until after a physiological sample has been drawn into the vial 502.

Figure 63:
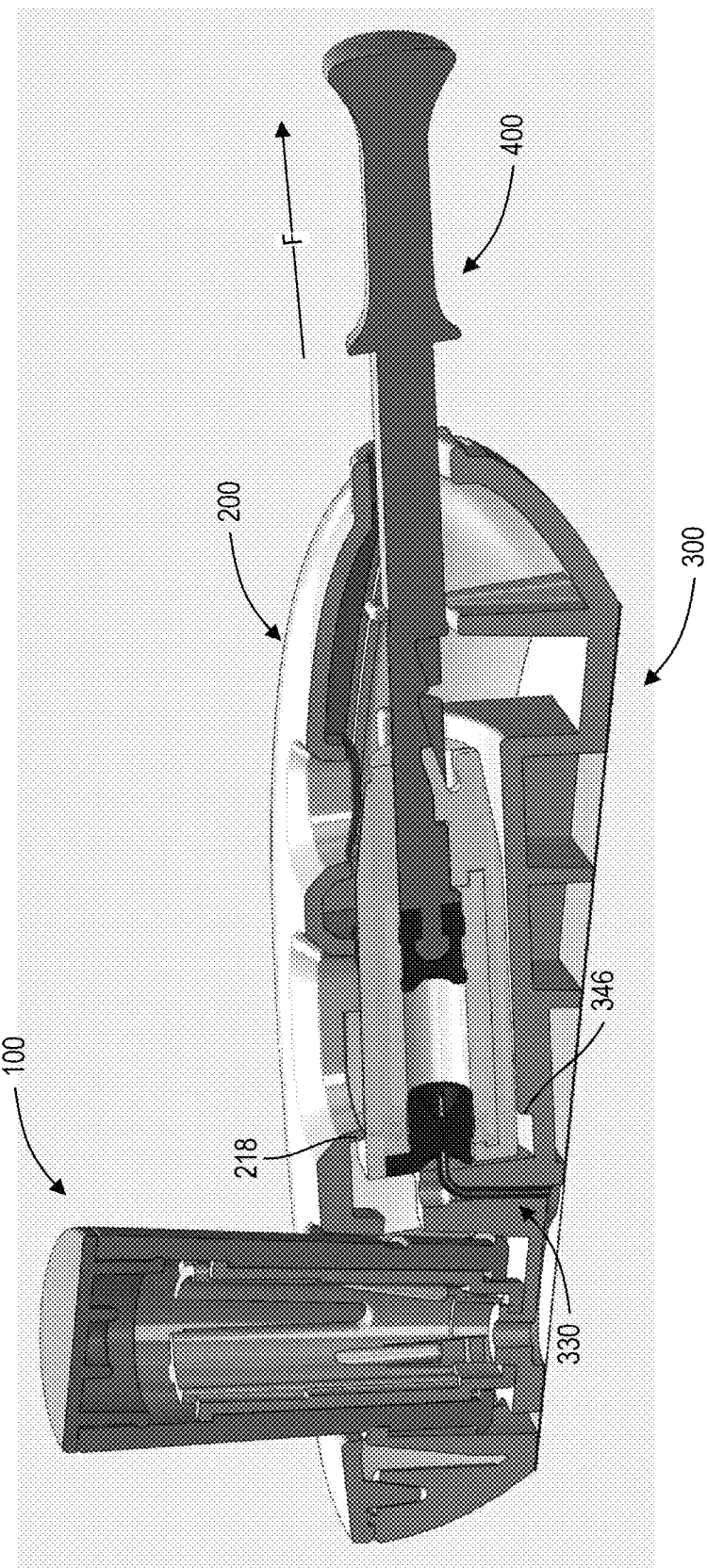
FIG. 63 depicts the dermal patch system wherein the vial assembly is in a vial removal position in accordance with an exemplary embodiment of the present disclosure.

After the user moves the plunger 400 to the deployed position, the user can rotate the vial assembly 500 by rotating plunger 400. Before rotation (i.e., when the vial assembly 500 is in the collection position), a side of the rib 528e contacts the rotational stop 222 which prevents a user from rotating the plunger 400 (and therefore the vial assembly 500) in a clockwise direction (when viewing the distal end of the plunger 400). After the user draws the physiological sample into the vial 502, the user can rotate the plunger 400 in a counterclockwise direction to place the vial assembly 500 in a second position (also referred to as a "vial removal position") (FIG. 63). During rotation the length of the rib 528d allows the rib 528d to rotate beyond the rotational stop 222. The vial assembly 500 is allowed to continue to rotate until the rotational stop 222 contacts the rib 526c which prevents the user from further rotating the vial assembly 500 thereby placing the vial assembly 500 in the vial removal position.

In the vial removal position, the flanges 512 rotate such that they do not contact the locking wall 218 or the protrusion 346. As such, the vial assembly 500 is free to move horizontally within the cartridge 12. The shape of the plunger interface 540 of the stopping member 506 and the shape of the projection members 414 of the plunger 400 allow a user to pull the vial assembly 500 when the vial assembly 500 is in the vial removal position. That is, the distal end surface 546 of the plunger interface 540 contacts the side surface 420 of a projection member 414 which causes the vial 502 to move with the plunger 400 when a user pulls the plunger 400.

Figure 64:
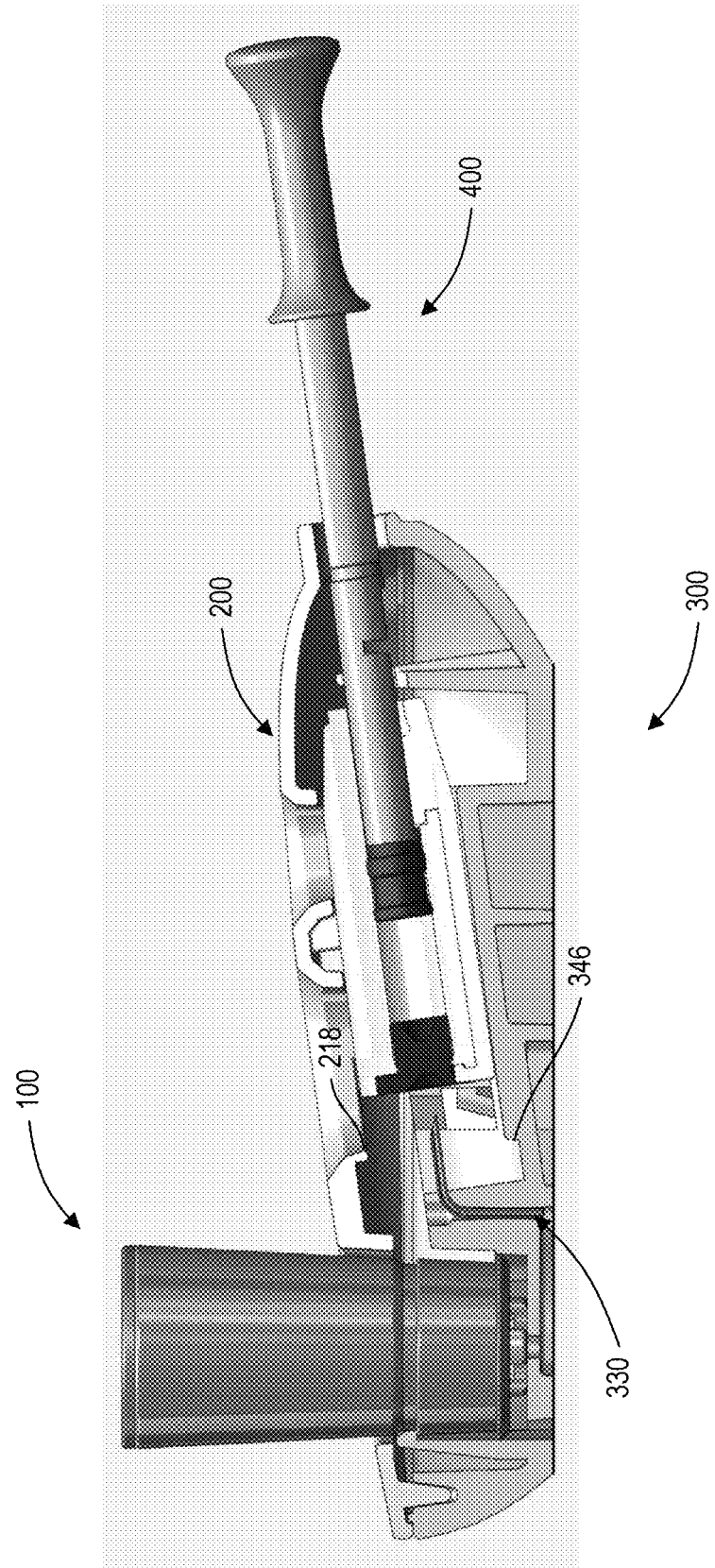
FIG. 64 depicts the dermal patch system wherein the vial assembly is in a vial storage position in accordance with an exemplary embodiment of the present disclosure.

When the vial assembly 500 is in the vial removal position, a user can continue pulling the plunger 400 in the direction of arrow F (FIG. 63) to place the vial assembly 500 in a third position (also referred to as a "vial storage position") (FIG. 64).

Figure 65:
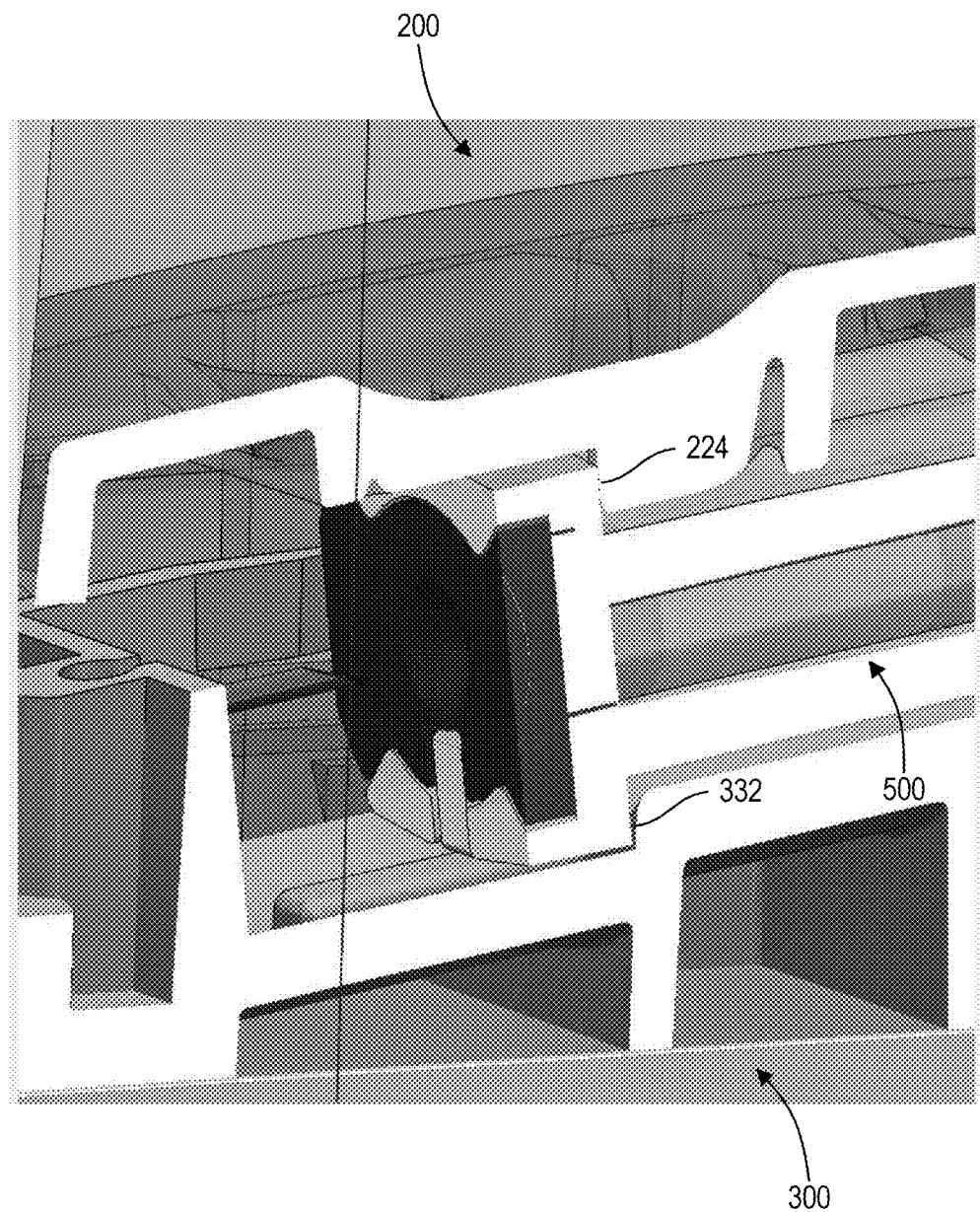
FIG. 65 depicts the vial assembly in the vial storage position in accordance with an exemplary embodiment of the present disclosure.
Figure 66:
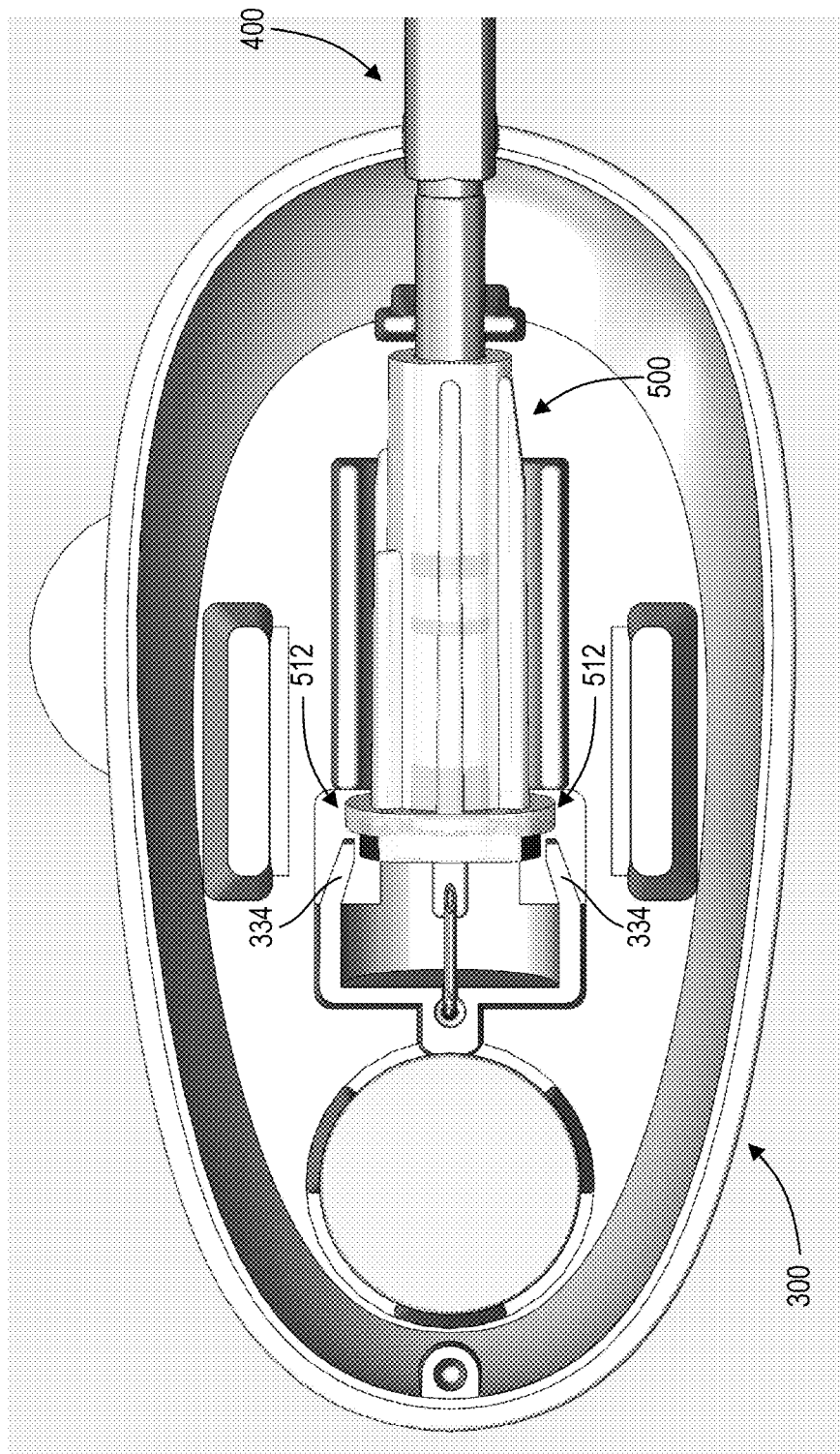
FIG. 66 depicts the vial assembly in the vial storage position in accordance with an exemplary embodiment of the present disclosure.

In the vial storage position, the vial assembly 500 contacts the stopping wall 224 and a proximal end surface of the first vial holder 332 from which the protrusion 346 extends which prevents further movement of the vial assembly 500 (FIG. 65). Furthermore, in this position, the vial assembly 500 no longer contacts the needle 330, thereby allowing the elastomeric cap 504 to heal and seal the vial 502. Also in this position, the latches 344 prevent a user from pushing the vial assembly 500 towards the needle 330 (FIG. 66). That is, when pushed from the vial storage position, the top surface 508a of the top wall 508 contacts the latches 344 which prevents the user from pushing the vial assembly 500 back onto the needle 330.

A user may remove the dermal patch system 10 from the skin of the subject immediately after drawing the physiological sample into the vial 502, or the user may remove the dermal patch system 10 after placing the vial assembly 500 in the vial storage position. After the vial assembly 500 has been placed in the vial storage position, the user may send the vial assembly system 10 to a laboratory for sample analysis.

In some embodiments, the vial 502 can be prefilled with a solution used for preserving the physiological sample (e.g., an anticoagulant), or another solution used for processing a physiological sample for further analysis by a medical device (e.g., a lysis buffer).

Figure 67:
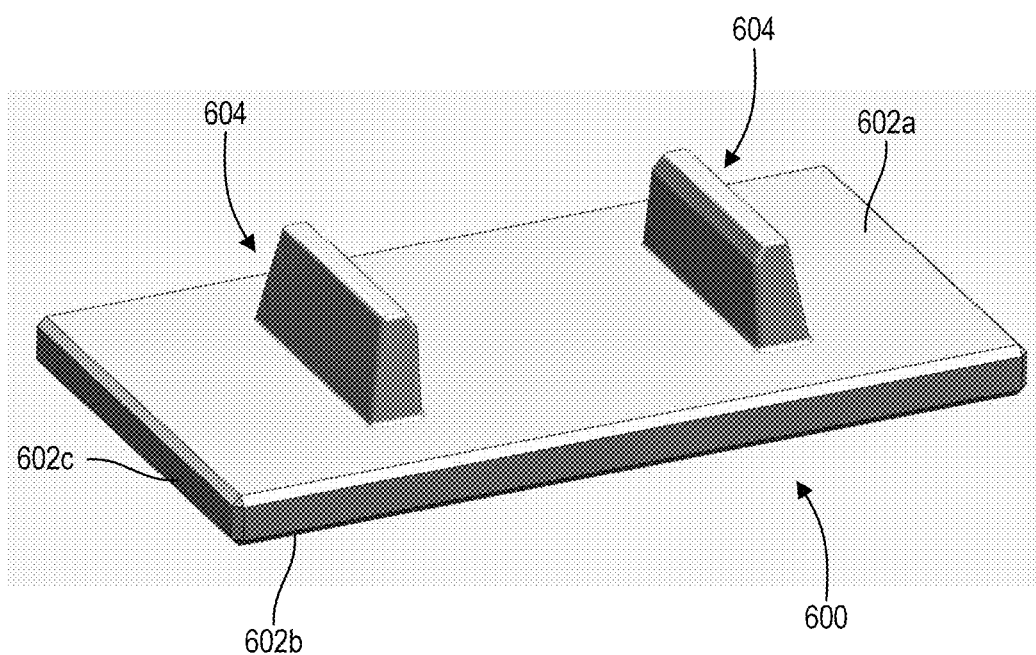
FIG. 67 depicts a lid removal tool in accordance with an exemplary embodiment of the present disclosure.

Referring now to FIG. 67, a lid removal tool 600 is shown in accordance with an exemplary embodiment.

The lid removal tool 600 includes a base 602 and extensions 604. The base 602 includes a top wall 602a, an opposed bottom wall 602b, and a side wall 602c that extends between the top wall 602a and the bottom wall 602b. The side wall 602c extends vertically between and perpendicular to the top wall 602a and the bottom wall 602b. The extensions 604 extend vertically from and perpendicular to the top wall 602a. The extensions 604 are shaped and dimensioned to fit into the openings 306 of the base 300.

Figure 68:
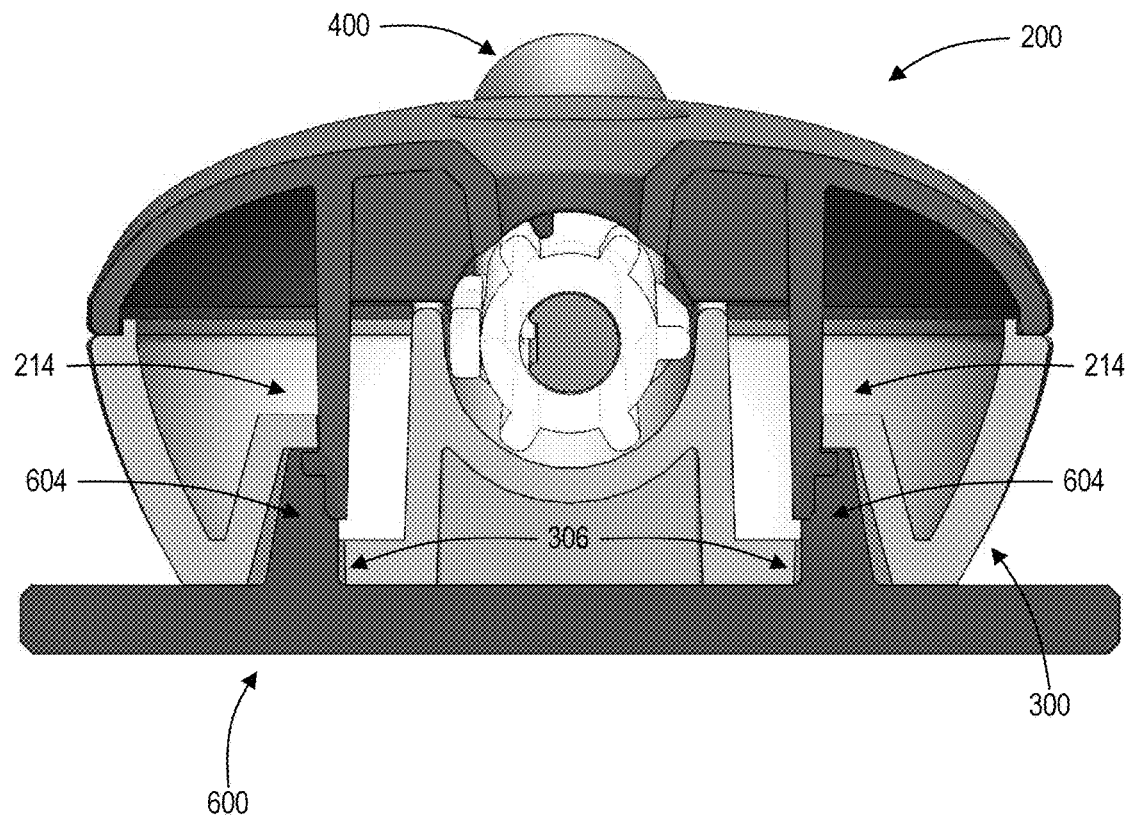
FIG. 68 depicts the lid removal tool decoupling the cover from the base in accordance with an exemplary embodiment of the present disclosure.

The lid removal tool 600 is configured to decouple the cover 200 from the base 300 which allows a medical professional to access the vial assembly 500 disposed therein. To decouple the cover 200 from the base 300, a medical professional inserts the extensions 604 of the lid removal tool 600 into the openings 306 of the base 300 (FIG. 68). When inserted, the extensions 604 contact the hooks 216 of the locking members 214 and push the locking members 214 towards the center of the cover 200 and away from the extensions 308 of the base 300. This movement separates the locking members 214 from the extensions 308 which allows the medical professional to lift cover 200 from the base 300. Once the cover 200 has been removed from the base 300, the medical professional can remove the plunger 400 and the vial assembly 500 from the base 300.

Figure 31A:
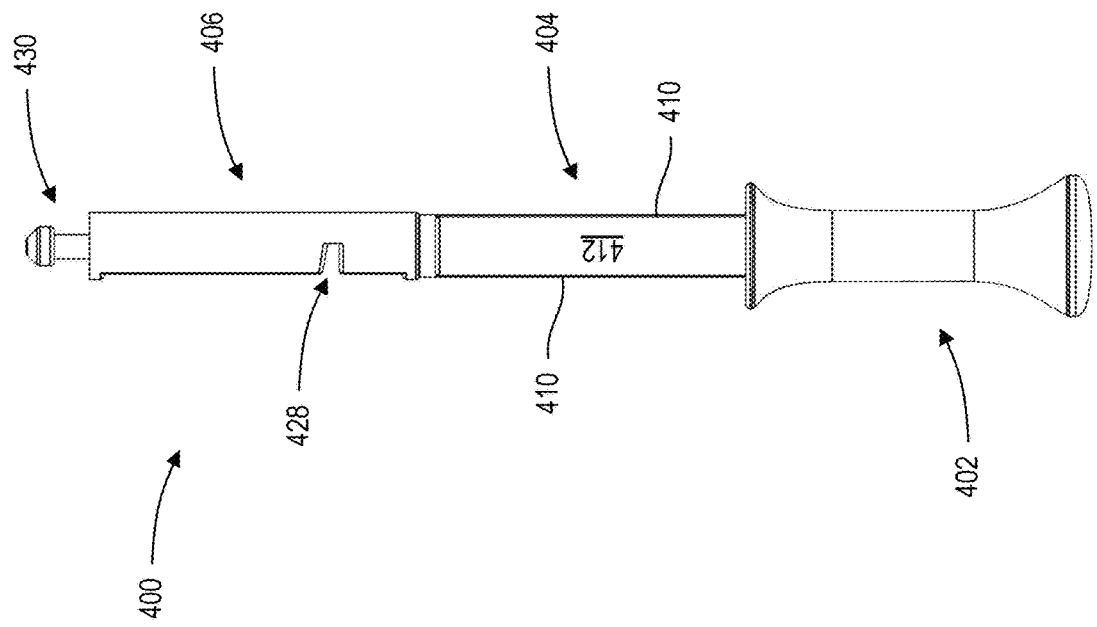
Figure 31B:
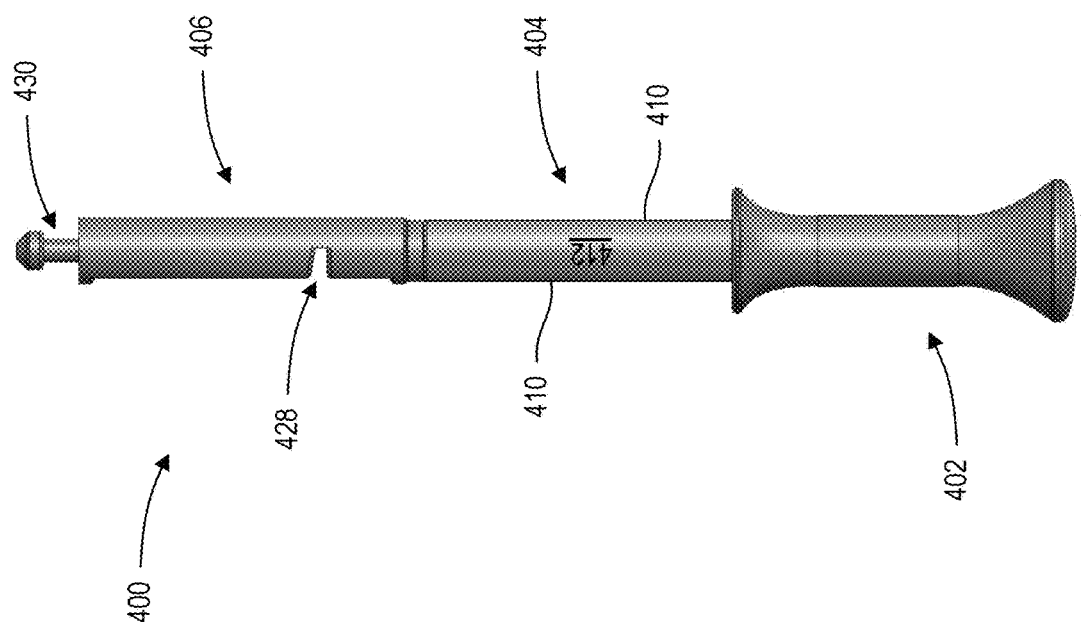
Figure 32:
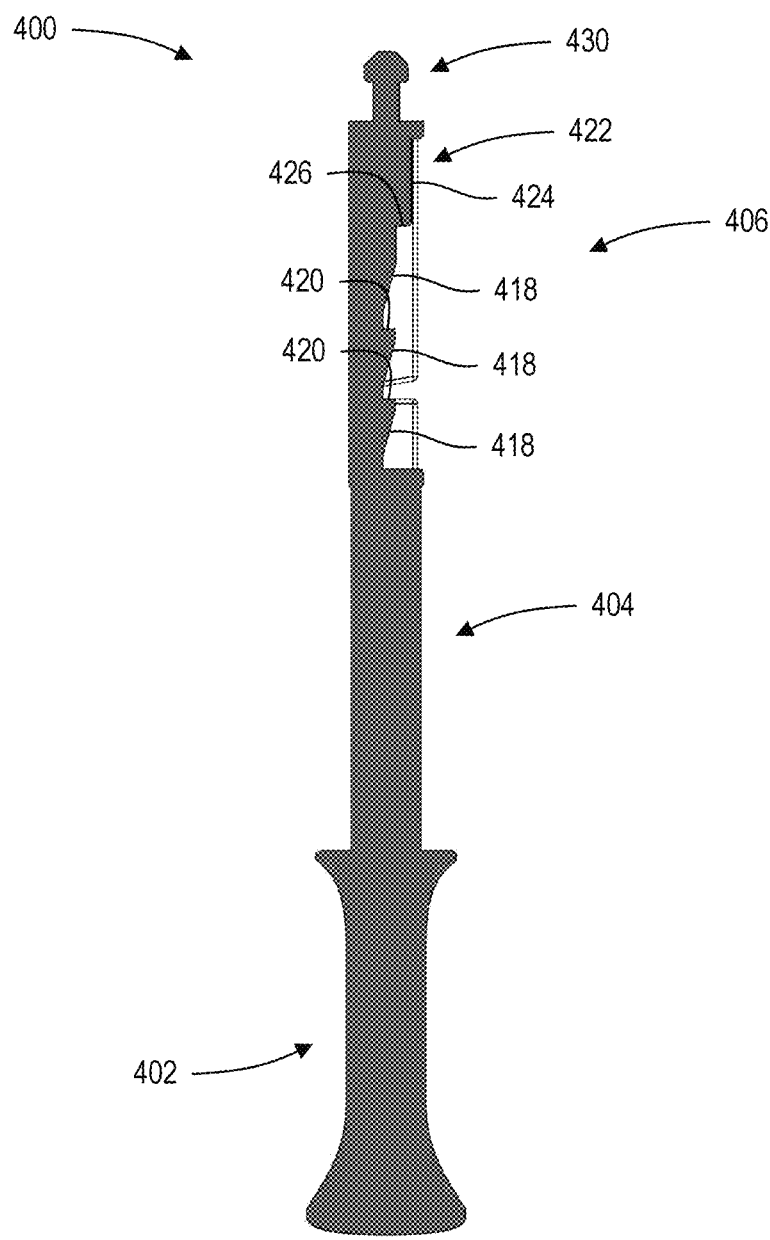
Figure 33:
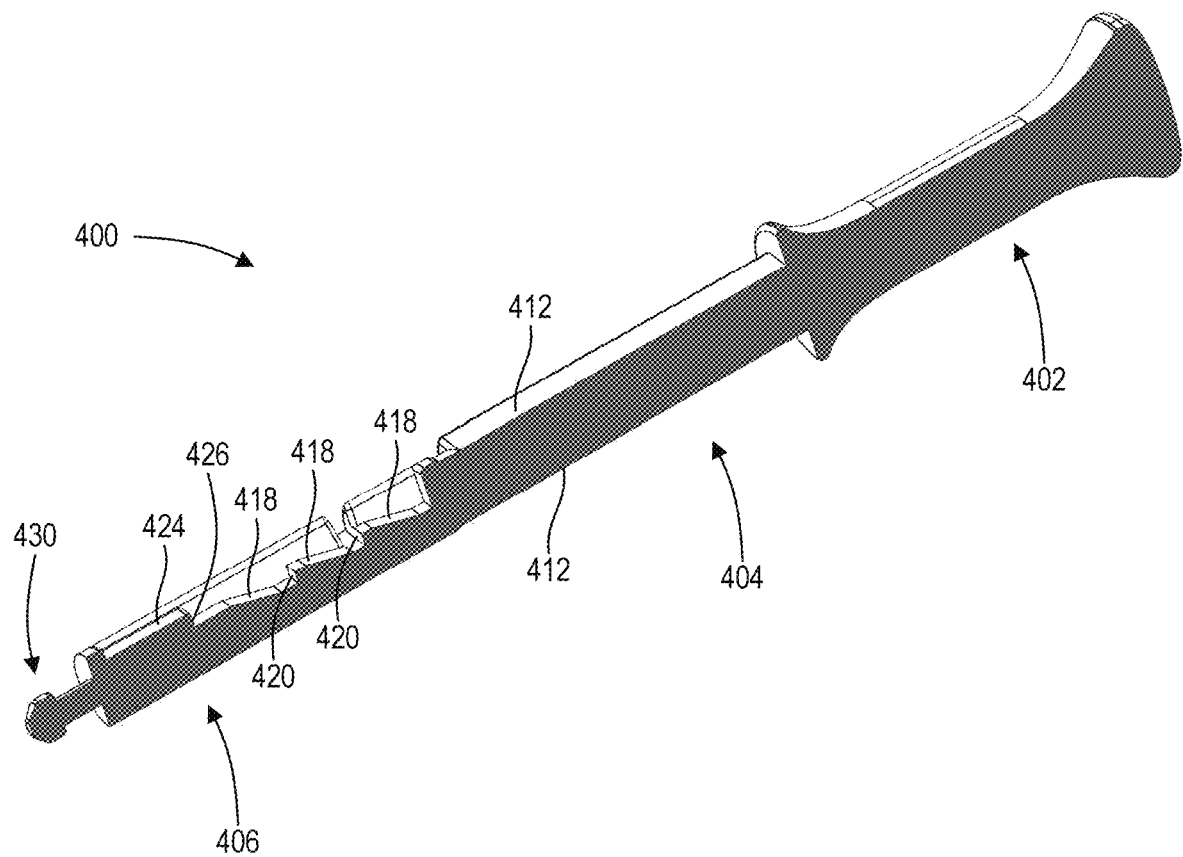
Figure 69:
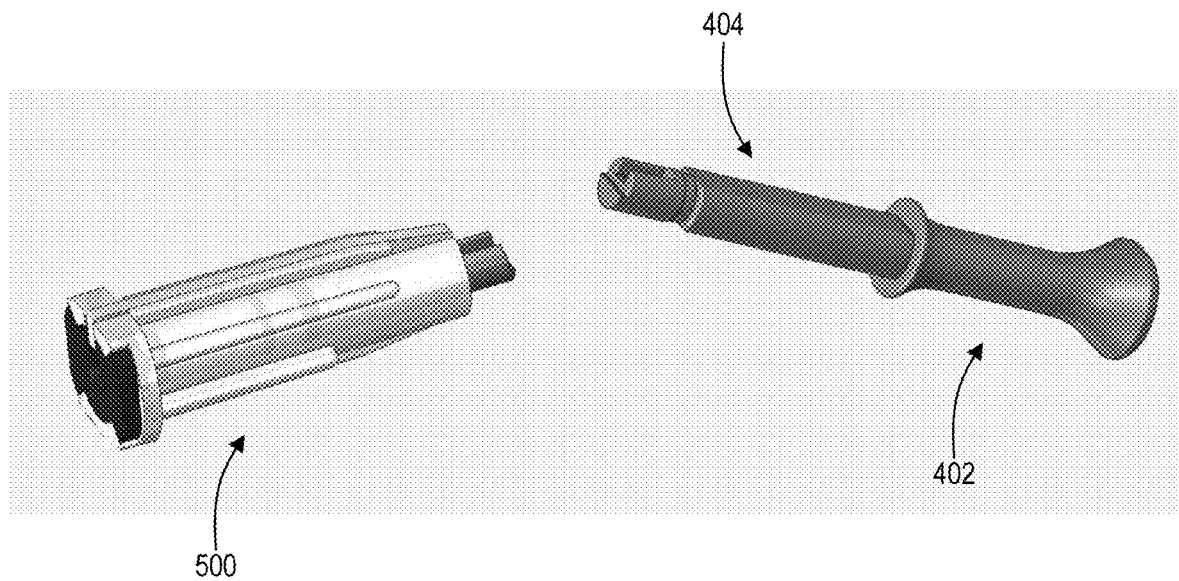
FIG. 69 depicts a broken plunger in accordance with an exemplary embodiment of the present disclosure.

As previously discussed herein, the plunger 400 includes a snap-off joint 428 that serves as a break point for the plunger 400 (FIG. 31). After removing the vial assembly 500 from the base 300, the medical professional can break the plunger 400 at the snap-off joint 428 to separate the handle 402 and the shaft 404 from a remainder of the plunger 400 (FIG. 69). Furthermore, the vial 502 can have a similar shape and dimension as a vial that can be placed into a centrifuge machine (e.g., a 1.5 mL Eppendorf tube) or another medical device. Accordingly, after breaking the plunger 400, a medical professional can place the sealed vial assembly into a medical device to analyze the stored physiological sample. The analysis can include, but is not limited to, DNA sequencing.

Figure 70:
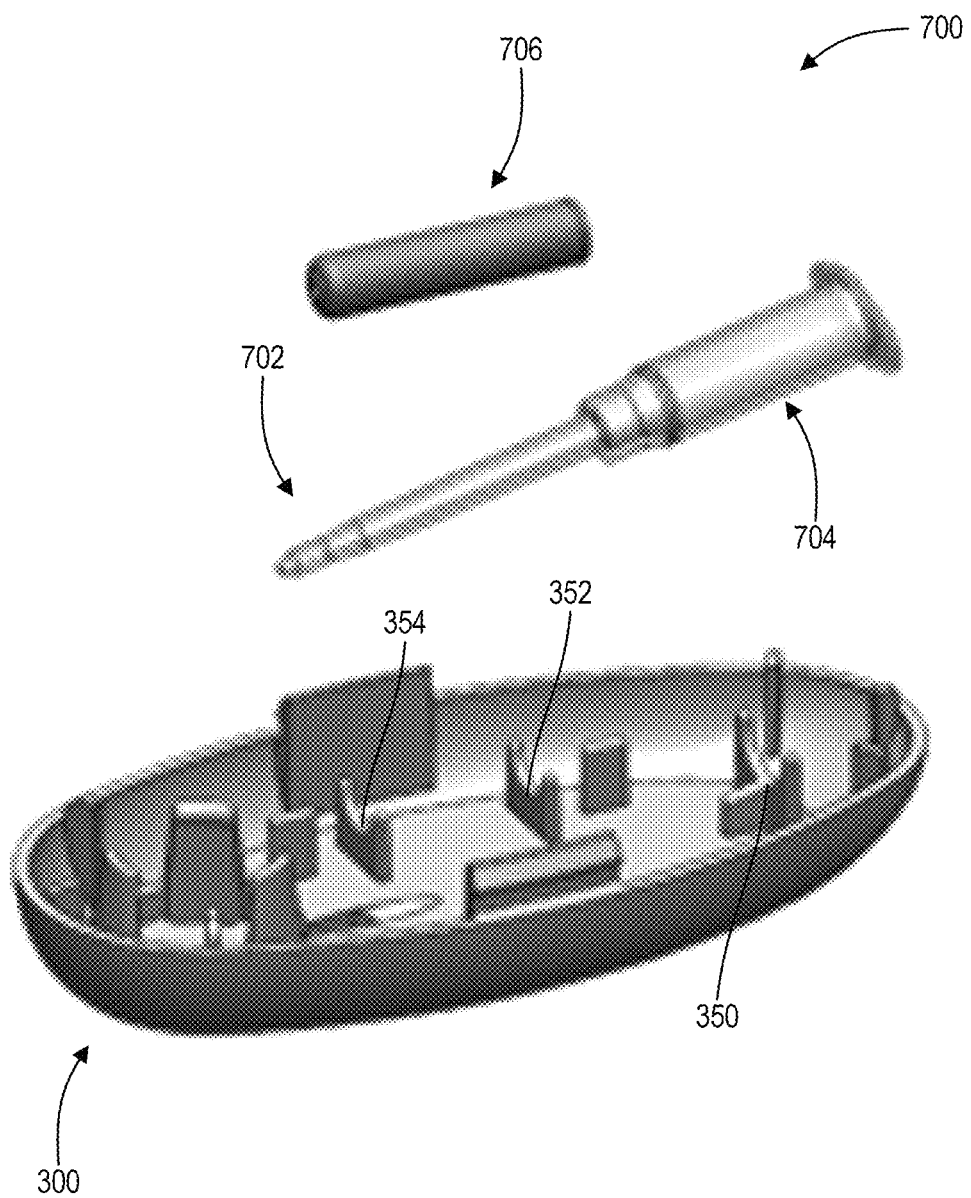
FIG. 70 depicts a base of a dermal patch system with a pipette in accordance with an exemplary embodiment of the present disclosure.
Figure 71:
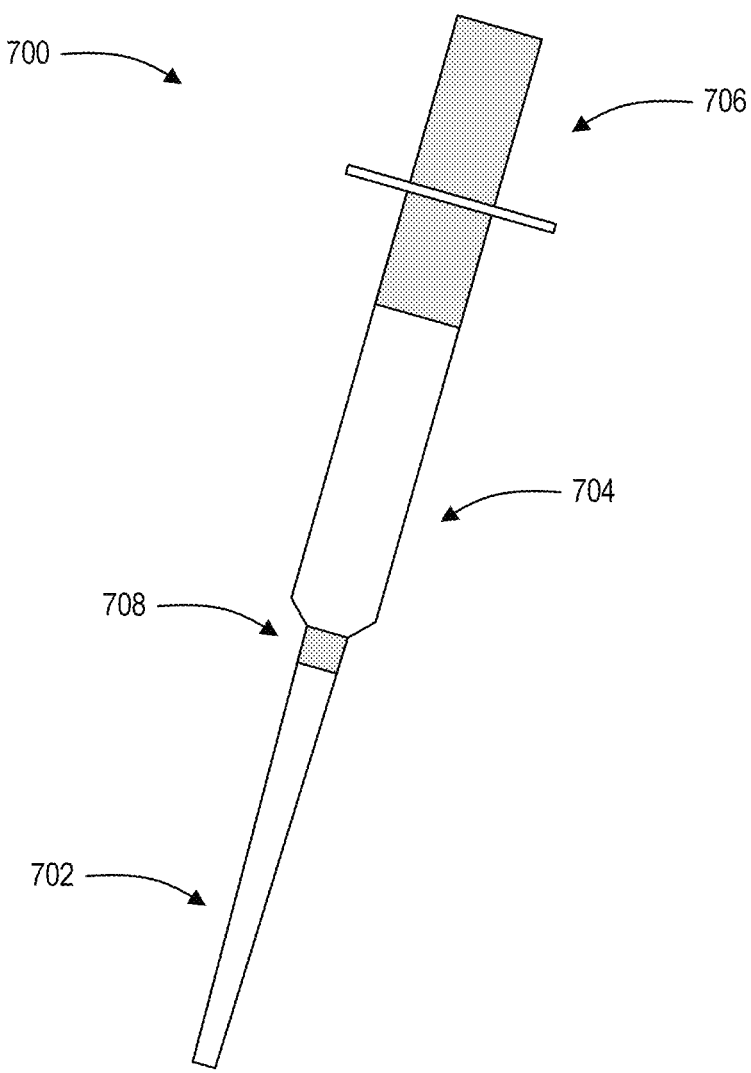
FIG. 71 depicts a pipette for use with the dermal patch system in accordance with an exemplary embodiment of the present disclosure.

With reference to FIGS. 70 and 71, the dermal patch system 10 can be modified to include a different system for blood collection. In some embodiments, the dermal patch system 10 can include a pipette 700. In these embodiments, the syringe 16 is omitted and the base 300 is modified to accommodate the pipette 700. Furthermore, in the embodiment depicted in FIGS. 70 and 71, the physiological sample is drawn into the pipette via capillary action.

The pipette 700 includes a tube 702 with an opening for accepting the drawn physiological sample and a barrel 704 in open communication with the tube 702. The pipette 700 further includes a piston 706 that aids in drawing the physiological sample into the barrel 704 partially disposed within the barrel 704. The pipette 700 further includes a filter 708 disposed within the tube 702. The filter 708 prevents the drawn physiological sample from traveling further into the barrel 704.

In this embodiment, the base 300 is modified to accommodate the pipette 700. In particular, the base 300 includes a first pipette support 350, a second pipette support 352, and a third pipette support 354. Each of the pipette supports 350-354 extends vertically from and perpendicular to the top surface 302a and each of the pipette supports 350-354 has a different height such that when the pipette 700 rests upon the pipette supports 350-354 the pipette 700 is angled downward towards the needle 330. Furthermore, in this embodiment, the needle 330 is omitted and the base 300 is further modified to include a channel (not shown) that allows at least a portion of the tube 702 to extend into the physiological sample well 326, which allows the 702 to carry the drawn physiological into the barrel 704 via capillary action.

Figure 72:
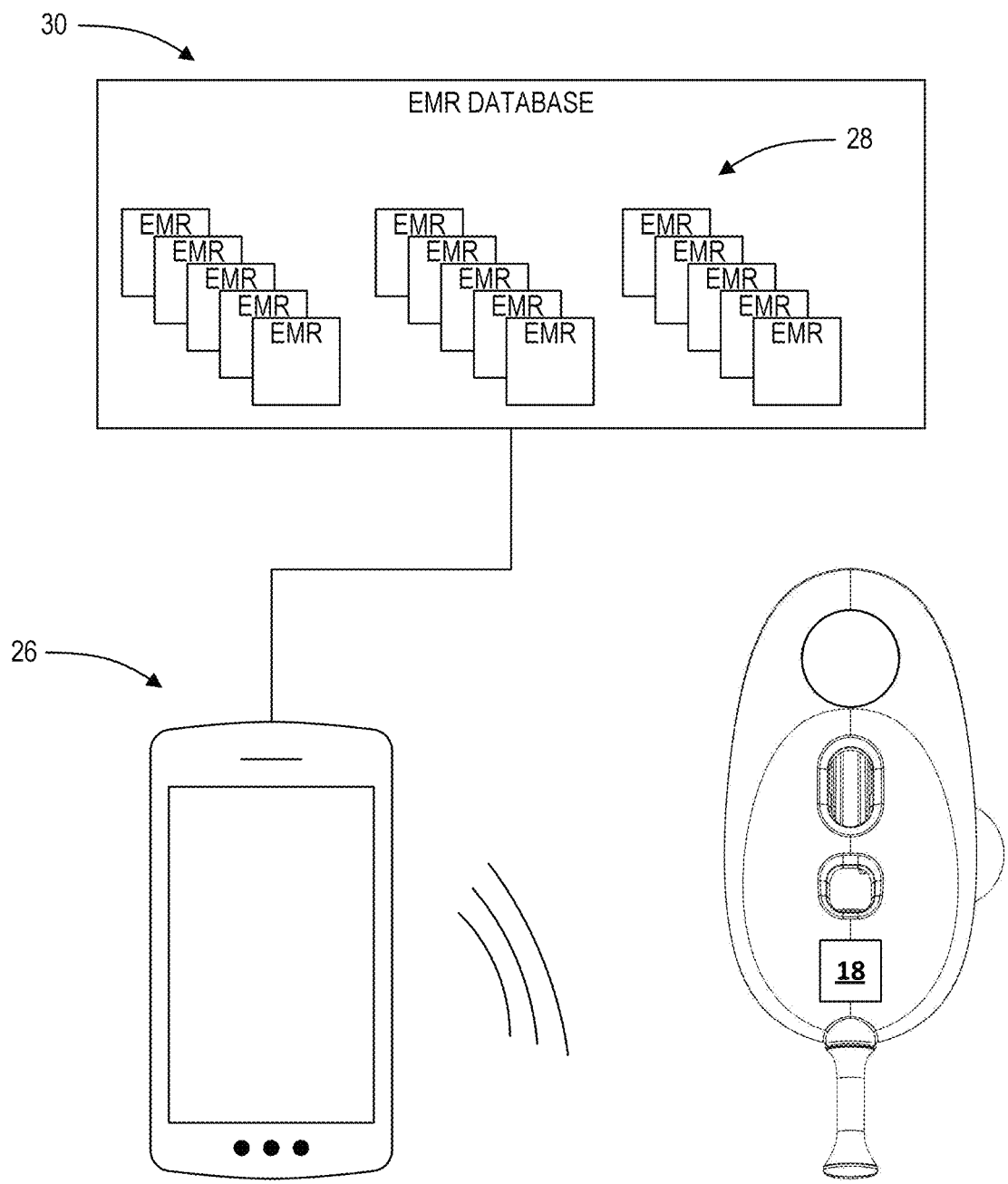
FIG. 72 diagrammatically depicts an electronic medical record database, a computer system, and a physiological sample collection pad with a quick response ("QR") code in accordance with an exemplary embodiment of the present disclosure.

With reference to FIG. 72, in some embodiments wherein the dermal patch system 10 includes the QR code 18, a user of a computer system 26 may scan the QR code 18 to determine a test to be perform on the stored physiological sample and/or to view and/or update an EMR 28 that is associated with the QR code 18. In these embodiments, the EMR 28 is stored in an EMR database 30 that is in communication with the computer system 26. Furthermore, the QR code 18 may be employed to preserve the chain of custody of the drawn physiological sample.

In these embodiments, the computer system 26 may include an application that provides access to the EMR database 28 via a network connection and allows a user to photograph or scan the QR code 18. As shown in FIG. 72, the EMR database 30 includes a plurality of EMRs 28 each of which is associated with an individual subject. The application causes the computer system 26 to scan or retrieve an image of the QR code 18, analyze the QR code 18 and associate the QR code 18 with an EMR 28. In some embodiments, the computer system 26 may then update the associated EMR 28 to indicate a physiological sample has been obtained. The computer system 26 may update the EMR 28 automatically or based on a user input. In some embodiments, after associating an EMR 28 with the QR code 18, the computer system 26 may analyze information within the EMR 28 to determine a test to be performed on the physiological sample stored in the vial 502 (e.g., DNA sequencing). After determining the test to be performed, the computer system 28 may instruct the medical professional to perform the test via the application.

Figure 73:
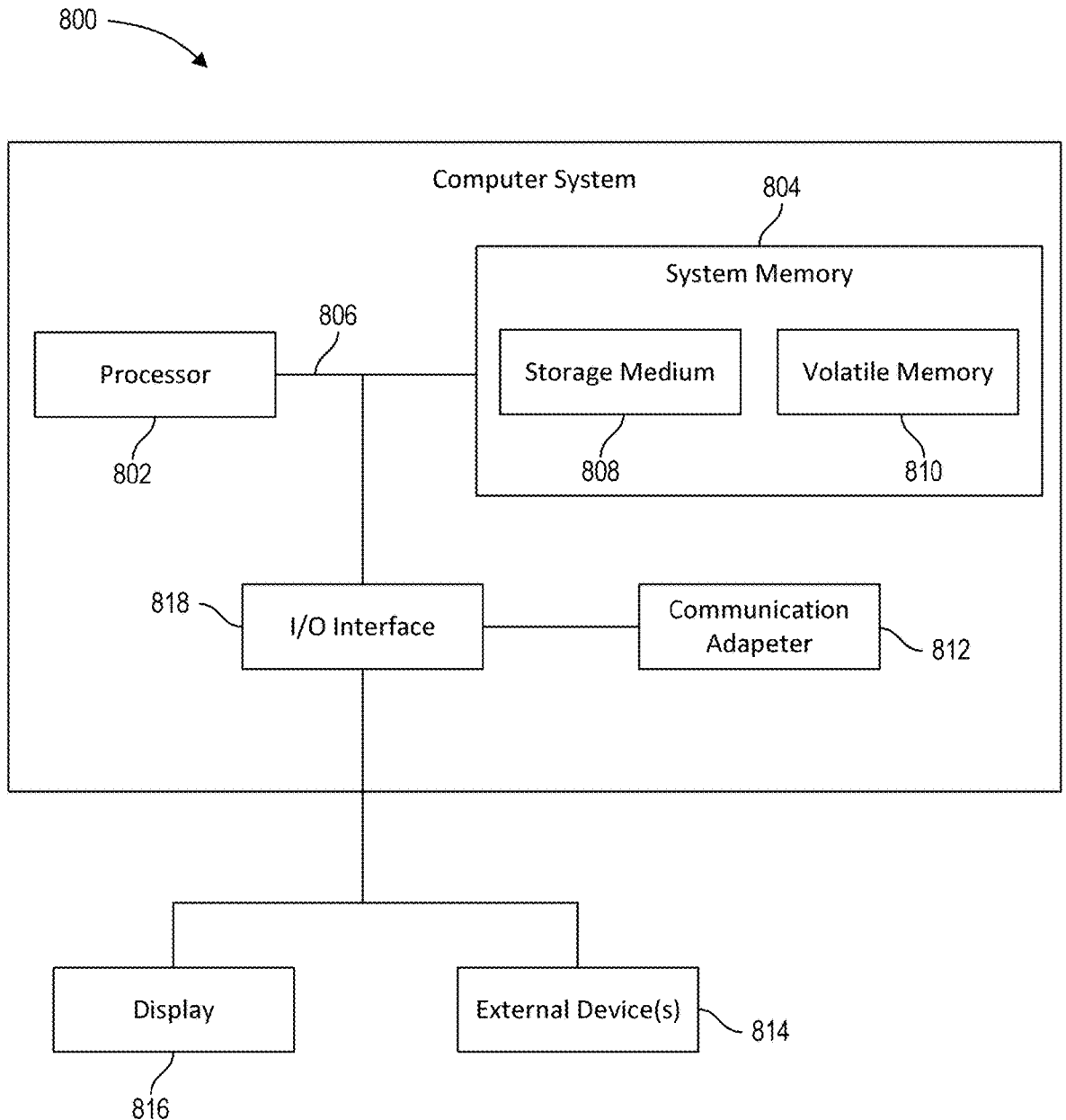
FIG. 73 diagrammatically depicts a computer system in accordance with an exemplary embodiment of the present disclosure.

Referring now to FIG. 73, a computer system 800 is shown in accordance with an exemplary embodiment. The computer system 800 may serve as any computer system disclosed herein (e.g., the computer system 20). As used herein a computer system (or device) is any system/device capable of receiving, processing, and/or sending data. Computer systems include, but are not limited to, microprocessor-based systems, personal computers, servers, hand-held computing devices, tablets, smartphones, multiprocessor-based systems, mainframe computer systems, virtual reality ("VR") headsets and the like.

As shown in FIG. 73, the computer system 800 includes one or more processors or processing units 802, a system memory 804, and a bus 806 that couples the various components of the computer system 800 including the system memory 804 to the processor 802. The system memory 804 includes a computer readable storage medium 808 and volatile memory 810 (e.g., Random Access Memory, cache, etc.). As used herein, a computer readable storage medium includes any media that is capable of storing computer readable; program instructions and is accessible by a processor. The computer readable storage medium 808 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

The bus 806 may be one or more of any type of bus structure capable of transmitting data between components of the computer system 800 (e.g., a memory bus, a memory controller, a peripheral bus, an accelerated graphics port, etc.).

The computer system 800 may further include a communication adapter 812 which allows the computer system 800 to communicate with one or more other computer systems/devices via one or more communication protocols (e.g., Wi-Fi, BTLE, etc.) and in some embodiments may allow the computer system 800 to communicate with one or more other computer systems/devices over one or more networks (e.g., a local area network (LAN), a wide area network (WAN), a public network (the Internet), etc.).

In some embodiments, the computer system 800 may be connected to one or more external devices 814 and a display 816. As used herein, an external device includes any device that allows a user to interact with a computer system (e.g., mouse, keyboard, touch screen, etc.). An external device 814 and the display 816 may be in communication with the processor 802 and the system memory 804 via an Input/Output (I/O) interface 818.

The display 816 may display a graphical user interface (GUI) that may include a plurality of selectable icons and/or editable fields. A user may use an external device 814 (e.g., a mouse) to select one or more icons and/or edit one or more editable fields. Selecting an icon and/or editing a field may cause the processor 802 to execute computer readable program instructions stored in the computer readable storage medium 808. In one example, a user may use an external device 814 to interact with the computer system 800 and cause the processor 802 to execute computer readable program instructions relating to at least a portion of the steps of the methods disclosed herein.

Figure 74:
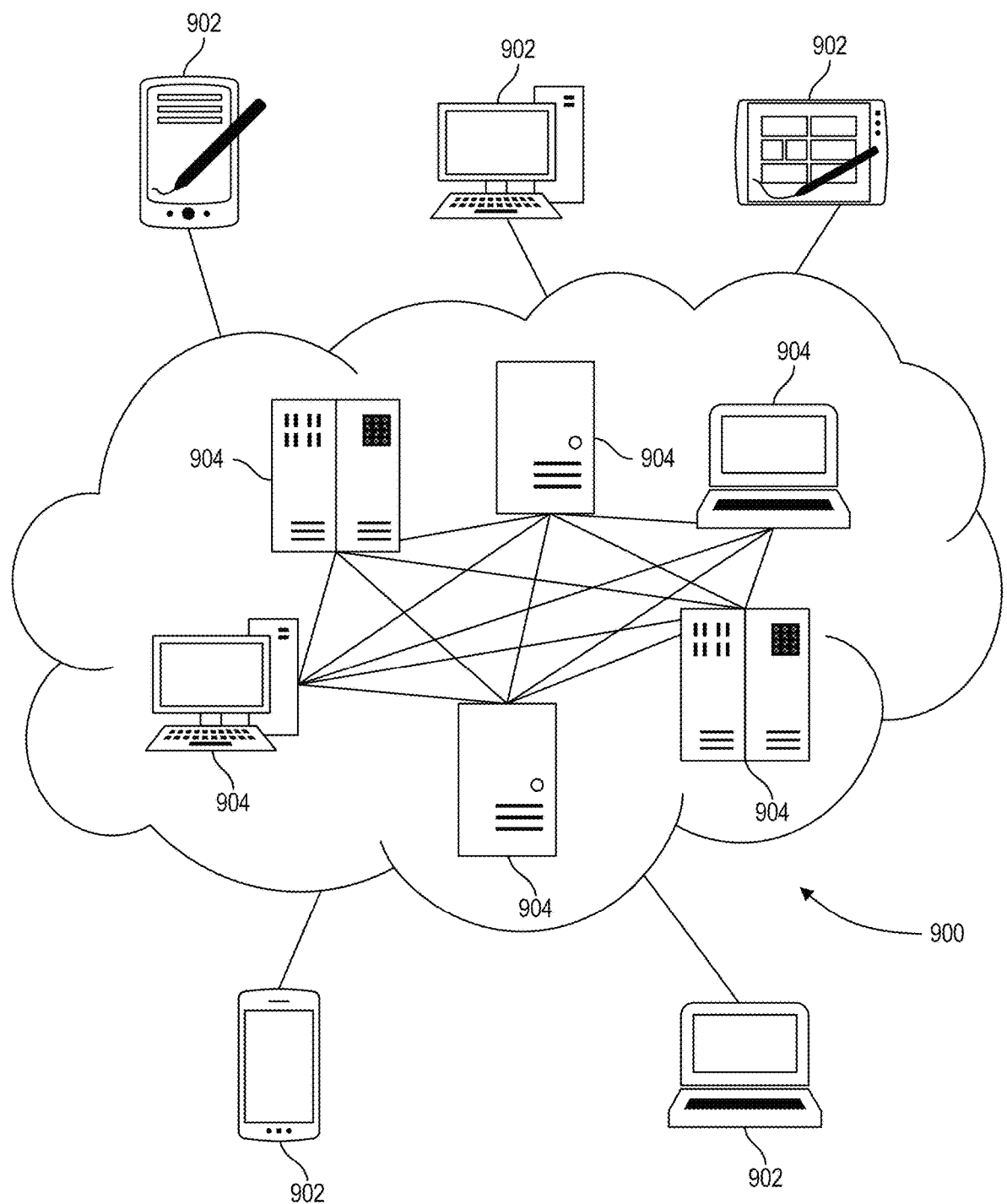
FIG. 74 diagrammatically depicts a cloud computing environment in accordance with an exemplary embodiment of the present disclosure.

Referring now to FIG. 74, a cloud computing environment 900 is depicted in accordance with an exemplary embodiment. The cloud computing environment 900 is connected to one or more user computer systems 902 and provides access to shared computer resources (e.g., storage, memory, applications, virtual machines, etc.) to the user computer systems 902. As depicted in FIG. 74, the cloud computing environment includes one or more interconnected nodes 904. Each node 904 may be a computer system or device local processing and storage capabilities. The nodes 904 may be grouped and in communication with one another via one or more networks. This allows the cloud computing environment 900 to offer software services to the one or more computer services to the one or more user computer systems 902 and as such, a user computer system 902 does not need to maintain resources locally.

In one embodiment, a node 904 includes computer readable program instructions for carrying out various steps of various methods disclosed herein. In these embodiments, a user of a user computer system 902 that is connected to the cloud computing environment may cause a node 904 to execute the computer readable program instructions to carry out various steps of various methods disclosed herein.

Figure 75:
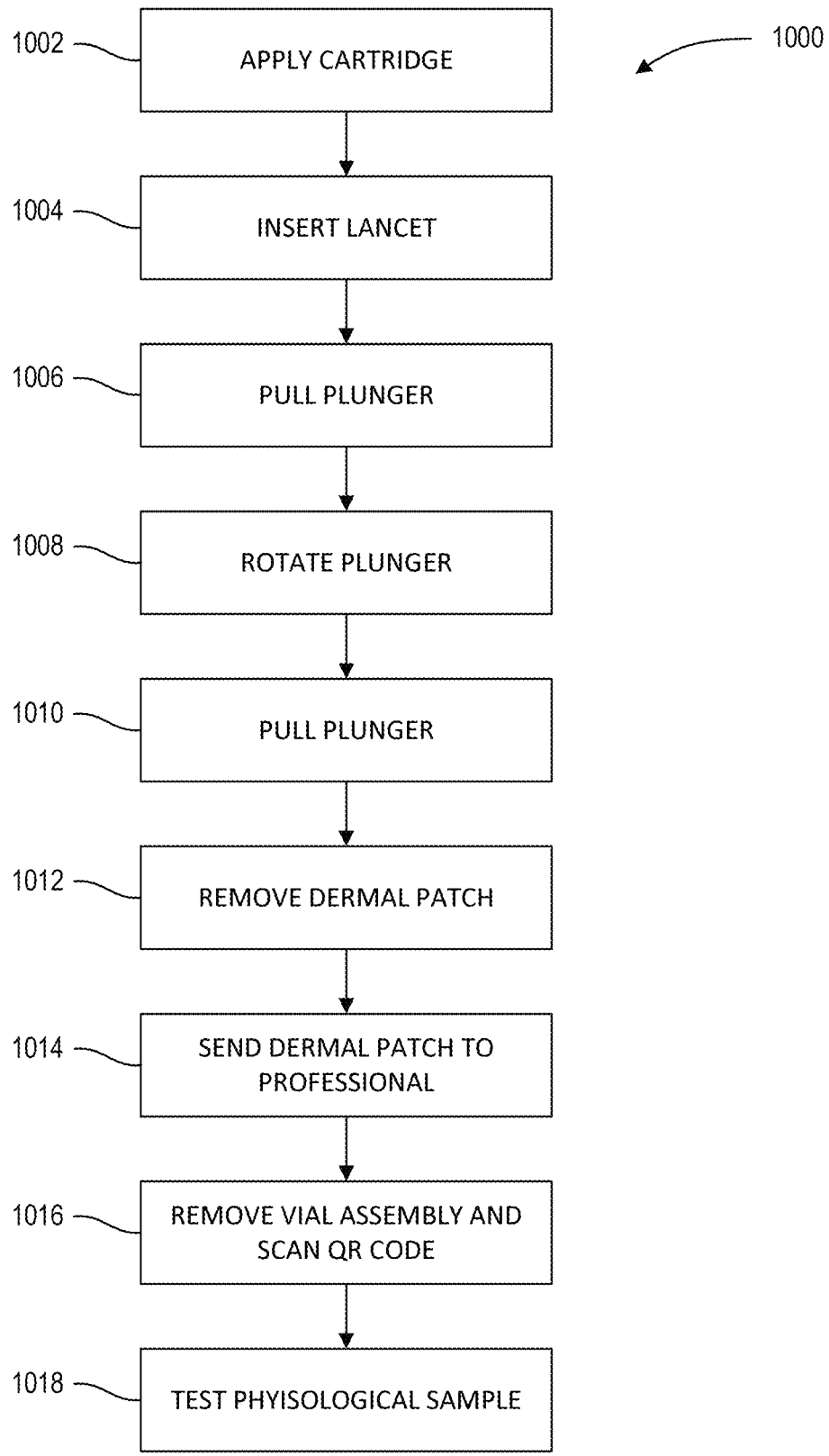
FIG. 75 is a flow chart of a method for obtaining a physiological sample from a subject in accordance with an exemplary embodiment of the present disclosure.

Referring now to FIG. 75, a method 1000 for obtaining a physiological sample is shown in accordance with an exemplary embodiment.

At 1002, a user e.g., a medical professional, a subject, etc.) applies the cartridge 12 to the skin of the subject via the adhesive layer 14 at a suitable location (e.g., on a leg, arm, etc.) as previously discussed herein.

At 1004, the user inserts the lancet 100 into the cartridge 12 thereby causing the needle 110 of the lancet 100 to draw a physiological sample (e.g., a blood sample, a sample of interstitial fluid, etc.) from the subject as previously discussed herein.

At 1006, the user pulls the plunger 400 to draw the physiological sample into the vial 502 as previously discussed herein.

At 1008, the user rotates the plunger 400 to place the vial assembly 500 in the vial removal position as previously discussed herein.

At 1010, the user pulls the plunger 400 to place the vial assembly in the vial storage position as previously discussed herein.

At 1012, the user removes the dermal patch system 10 from the skin of the subject as previously discussed herein.

At 1014, the user sends the dermal patch system 10 to a medical professional as previously discussed herein.

At 1016, a medical professional uses the lid removal tool 600 to remove the vial assembly 500 from the cartridge 12 and scans the QR code 18 to update an EMR as previously discussed herein.

At 1018, the medical professional breaks the plunger and performs a test on the physiological sample as previously discussed herein.

As previously discussed, some of the steps of the various methods disclosed herein may be implemented by way of computer readable instructions, encoded or embedded on computer readable storage medium (which excludes transitory medium), which, when executed by a processor(s), cause the processor(s) to carry out various steps of the methods of the present disclosure.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A device for collecting a physiological sample from a subject, comprising:
   a lancet with a first needle configured to puncture the subject's skin, a cartridge configured to couple to the lancet, wherein the lancet is configured to automatically deploy the first needle when the lancet is coupled to the cartridge so as to allow the first needle to puncture the subject's skin and draw the physiological sample from the subject,
   a vial assembly disposed within the cartridge and configured to receive the drawn physiological sample, the vial assembly having a vial is disposed therein; and
   a plunger at least partially disposed within the vial assembly and configured to create a vacuum within the vial, wherein the vacuum draws the physiological sample to the vial, wherein the vial assembly is coupled to the plunger such that removal of the plunger from the cartridge causes the vial assembly to be removed from the cartridge.

2. The device of claim 1, wherein the vial is configured to be placed into a centrifuge machine.

3. The device of claim 1, wherein the vial includes a preservative or a lysis buffer.

4. The device of claim 1, wherein the vial includes an anticoagulant.

5. The device of claim 1, wherein the cartridge further comprises:
   a physiological sample well, and a second needle in open communication with the physiological sample well and configured to carry the physiological sample from the physiological sample well to the vial.

6. The device of claim 1, wherein the plunger includes a notch that allows a user to break the plunger, thereby separating the plunger from the vial assembly.

7. The device of claim 5, further comprising:
   a self-healing cap coupled to the vial, wherein the self-healing cap is configured to seal the vial after being punctured.

8. The device of claim 7, wherein the second needle is configured to puncture the self-healing cap to carry the physiological sample to the vial.

9. The device of claim 1, wherein the cartridge comprises:
   a cover, and
   a base removably coupled to the base.

10. The device of claim 9, wherein the cover includes a vial viewing aperture configured to provide visual access to the vial disposed within the cartridge.

11. The device of claim 9, further comprising:
    a quick response code disposed on an outer surface of the vial.

12. The device of claim 11, wherein the cover includes a quick response code viewing aperture configured to provide visual access to the quick response code.

13. The device of claim 1, wherein the plunger is rotationally coupled to the vial assembly such that rotation of the plunger causes the vial assembly to rotate to a vial removal position.

14. The device of claim 13, wherein the vial includes a plurality of ribs that extend along an outer surface a side wall, wherein at least two of the ribs prevent the vial assembly from rotating beyond a given position.

* * * * *